US009358281B2

(12) United States Patent
Littman et al.

(10) Patent No.: US 9,358,281 B2
(45) Date of Patent: Jun. 7, 2016

(54) METHODS, AGENTS AND PEPTIDES FOR INDUCING AN INNATE IMMUNE RESPONSE IN HIV VACCINATION

(75) Inventors: Dan Littman, New York, NY (US); Nicolas Manel, Paris (FR)

(73) Assignee: New York University, New York, NY (US)

( * ) Notice: Subject to any disclaimer, the term of this patent is extended or adjusted under 35 U.S.C. 154(b) by 661 days.

(21) Appl. No.: 12/925,068

(22) Filed: Oct. 12, 2010

(65) Prior Publication Data

US 2011/0159025 A1 Jun. 30, 2011

Related U.S. Application Data

(60) Provisional application No. 61/278,759, filed on Oct. 9, 2009, provisional application No. 61/402,336, filed on Aug. 27, 2010.

(51) Int. Cl.
*A61K 39/21* (2006.01)
*A61P 37/00* (2006.01)
*C12Q 1/70* (2006.01)
*G01N 33/569* (2006.01)
*C07K 14/005* (2006.01)
*A61K 39/12* (2006.01)
*A61K 39/00* (2006.01)

(52) U.S. Cl.
CPC ............... *A61K 39/21* (2013.01); *A61K 39/12* (2013.01); *C07K 14/005* (2013.01); *G01N 33/56988* (2013.01); *A61K 2039/5258* (2013.01); *A61K 2039/53* (2013.01); *A61K 2039/57* (2013.01); *A61K 2039/6031* (2013.01); *C12N 2740/16011* (2013.01); *C12N 2740/16034* (2013.01); *C12N 2740/16222* (2013.01); *C12Q 1/70* (2013.01); *G01N 2333/16* (2013.01); *G01N 2500/10* (2013.01)

(58) Field of Classification Search
CPC ............ C12N 15/86; C12N 7/00; C12N 2740/16043; C12N 15/62; A61K 48/00; A61K 38/00; A61K 47/48269; C07K 14/005; C07K 2319/00; C07K 14/765
USPC ........................................................ 424/188
See application file for complete search history.

(56) References Cited

U.S. PATENT DOCUMENTS

| | | | |
|---|---|---|---|
| 5,773,225 A | 6/1998 | Luban et al. | |
| 5,840,305 A | 11/1998 | Bukrinsky et al. | |
| 2006/0257974 A1 | 11/2006 | Howley et al. | |
| 2007/0104690 A1 | 5/2007 | Kingsman et al. | |
| 2007/0248679 A1 * | 10/2007 | Ertl | 424/489 |
| 2008/0045454 A1 | 2/2008 | Luban et al. | |
| 2008/0226675 A1 * | 9/2008 | Xu | 424/208.1 |

FOREIGN PATENT DOCUMENTS

| | | | |
|---|---|---|---|
| WO | 03025003 | | 3/2003 |
| WO | WO2004073641 | * | 9/2004 |
| WO | 2009026183 | | 2/2009 |

OTHER PUBLICATIONS

Arnold et al., At least five HIV-1 Sequence Subtypes (A, B, C, D, A/E) occur in England, 1995, AIDS Research and Human Retroviruses, 11(3):427-429.*
Sadjadpour et al., Induction of disease by a molecularly cloned highly pathogenic Simian Immunodeficiency Virus/Human Immunodeficiency Virus Chimera is multigenic, 2004, Journal of Virology, 78(10):5513-5519.*
VerPlank et al., Tsg101, a homologue of ubiquitin-conjugating (E2) enzymes, binds the L domain in HIV type 1 Pr55gag, 2001, PNAS, 98(14):7724-7729.*
Hahn et al., Relation of HTLV-4 to simian and human immunodeficiency-associated viruses, Nature, 1987, 330:184-186).*
Piller et al. "Vpr protein of human immunodeficiency virus type 1 forms cation-selective channels in planar lipid bilayers", 1996, Proc. Natl. Acad. Sci., 93:111-115.*
Yan et al., "The cytosolic exonuclease TREX1 inhibits the innate immune respnse to human immunodeficiency virus type 1", Nature Immunology, 2010, vol. 11, pp. 1005-1013.
Stetson et al., "TREX1 prevents cell-intrinsic initiation of autoimmunity", Cell, 2008, vol. 134, pp. 587-598.
Wu et al., "Targeting foreign proteins to human immunodeficiency virus particles via fusion with Vpr and Vpx", Journal of Virology, 1995, 69, 3389-3398.
Manel et al., "A cryptic sensor for HIV-1 activates antiviral innate immunity in dendritic cells", Nature, 2010, 467, 214-217.
Gataanga et al., "Altered HIV-1 gag protein interactions with cyclophilin a (CypA) on the acquisition of H219Q and H219P substitutions in the CypA binding loop", J Biol Chem, 2006, vol. 281, No. 2, pp. 1241-1250.
Colgan et al., "Binding of the human immunodeficiency virus type 1 gag polyprotein to cyclophilin A is mediated by the central region of capsid and requires gag dimerization", J Virol, 1996, vol. 70, No. 7, pp. 4299-4310.
Mangeot et al., "High levels of transduction of human dendritic cells with optimized SIV vectors", Molecular Therapy, 2002, vol. 5, pp. 283-290.

(Continued)

*Primary Examiner* — Joanne Hama
*Assistant Examiner* — Barry A Chestnut
(74) *Attorney, Agent, or Firm* — Klauber & Jackson LLC

(57) ABSTRACT

The present invention relates to enhancing, modulating or stimulating the innate immune response to HIV-1 and other viral pathogens and to the modulation and application of immune modulators and peptides for HIV-1 or other pathogen vaccines. The invention provides methods and means to activate an innate response to HIV-1 utilizing or via the HIV capsid protein or peptide, including modulating the binding of cyclophilin A to HIV capsid protein and modulating the ability of HIV to activate the major innate transcription factor IRF3 and interferon. Methods and assays are provided for screening for compounds, agents, or peptides capable of enhancing or activating innate immune response, particularly to HIV-1.

12 Claims, 20 Drawing Sheets

(56) References Cited

OTHER PUBLICATIONS

Negre et al., "Characterization of novel safe lentiviral vectors derived from simian immunodeficiency virus (SIVmac251) that efficiently transduce mature human dendritic cells", Gene Therapy, 2000, vol. 7, pp. 1613-1623.

Sawant et al., "Enhanced cytotoxicity of TATp-bearing paclitaxel-loaded micelles in vitro and in vivo", Int J Pharm, 2009, vol. 374, pp. 114-118.

Torchilin et al., "Tat peptide-mediated intracellular delivery of pharmaceutical nanocarriers", Advanced Drug Delivery Reviews, 2008, vol. 60, pp. 548-558.

Goujon et al., "With a little help from a friend: Increasing HIV transduction of monocyte-derived dendritic cells with virion-like particles of SIVmac", Gene Therapy, 2006, vol. 13, pp. 991-994.

Takeuchi et al., "Innate immunity to virus infection", Immunological Reviews, 2009, vol. 227, pp. 75-86.

Reimer et al., "Conformational state of a 25-mer peptide from the cyclophilin-binding loop of the HIV type 1 capsid protein", Biochem J., 1997, vol. 326, pp. 181-185.

Cheong et al., Improved cellular and humoral immune responses in vivo following targeting of HIV gag to dendritic cells within human anti-human DEC205 monoclonal antibody, Blood, 2010, vol. 116, pp. 3828-3838.

Goujon et al., "Characterization of simian immunodeficiency virus SIVSM/human immunodeficiency virus type 2 Vpx function in human myeloid cells", Journal of Virology, 2008, vol. 82, pp. 12335-12345.

Accola et al., "A conserved dileucine-containing motif in p6gag governs the particle association of Vpx and Vpr of simian immunodeficiency viruses SIVmac and SIVagm", Journal of Virology, 1999, 73:9992-9999.

Horton et al., "HIV-2 viral protein X association with the Gag p27 capsid protein", Virology, 1994, 199:453-457.

Paxton et al., "Incorporation of Vpr into human immunodeficiency virus Type 1 Virions: Requirement for the p6 Region of gag and Mutational Analysis", Journal of Virology, 1993, 67:7229-7237.

Shibata et al., "Infection and pathogenicity of chimeric simian-human immunodeficiency viruses in macaques: Determinants of high virus loads and CD4 cell killing", The Journal of Infectious Diseases, 1997, 176:362-373.

Manel et al., "A cryptic sensor for HIV-1 activates antiviral innate immunity in dendritic cells", Nature, 2010, 467:214-217.

Manel et al., "Censoring the sensors: How HIV flies under the radar of innate immunity", Cell, 2011, 147:271-274.

Iwasaki, "Innate immune recognition of HIV-1", Immunity, 2012, 37:389-398.

Yan et al., "Intrinsic antiviral immunity", Nature Immunology, 2012, 13:214-222.

Cox et al., "Making sense of HIV innate sensing", Immunity, 2013, 39:998-1000.

Maelfait et al., "Keeping your armour intact: How HIV-1 evades detection by the innate immune system", Bioessays, 2014, 36:649-657.

Editor's Summary, "HIV-1 in dendritic cells", Nature, 2010, 467.

\* cited by examiner

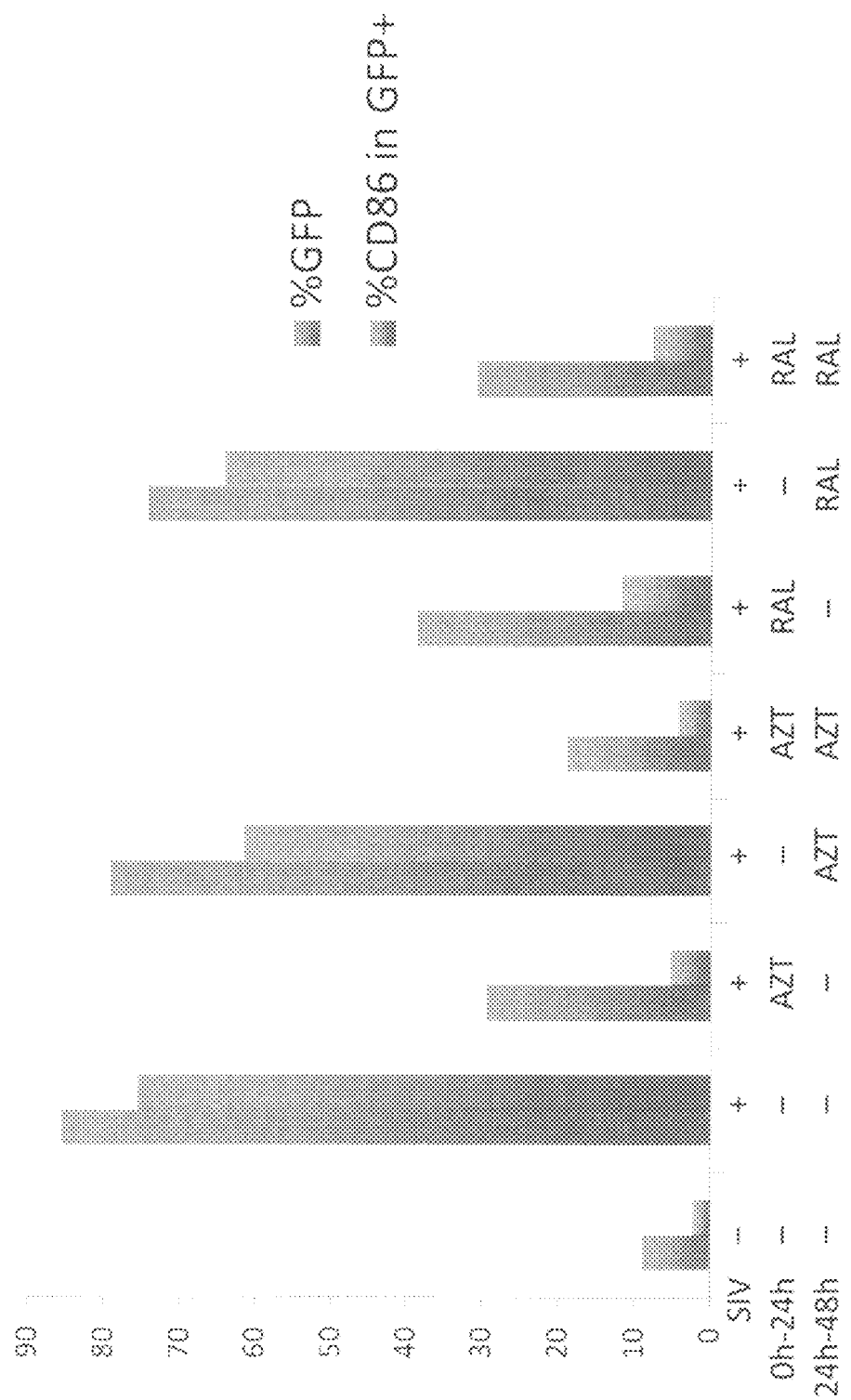

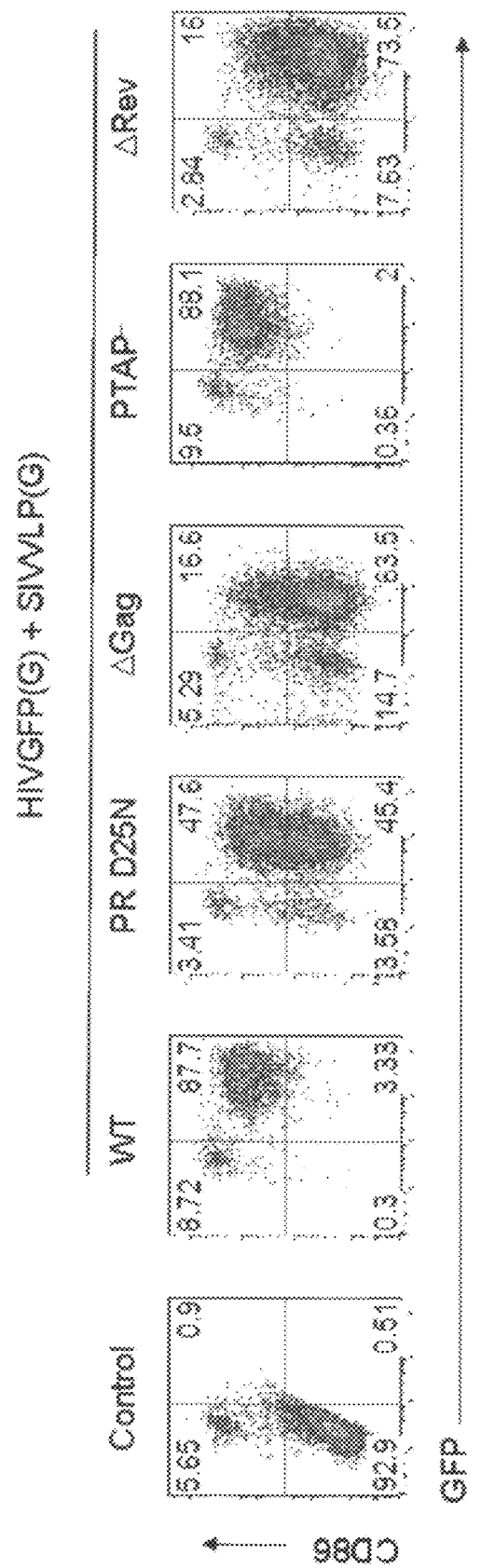

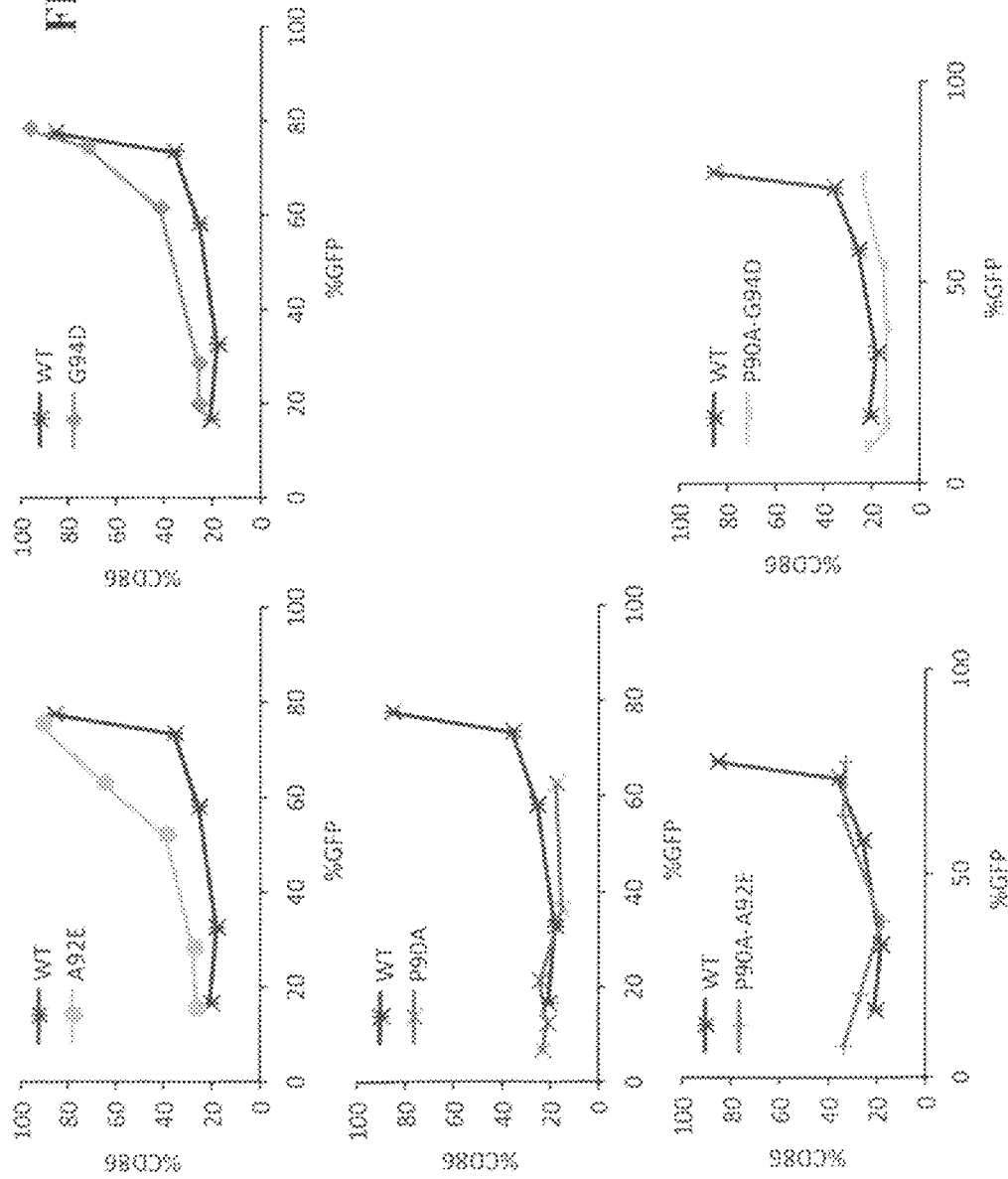

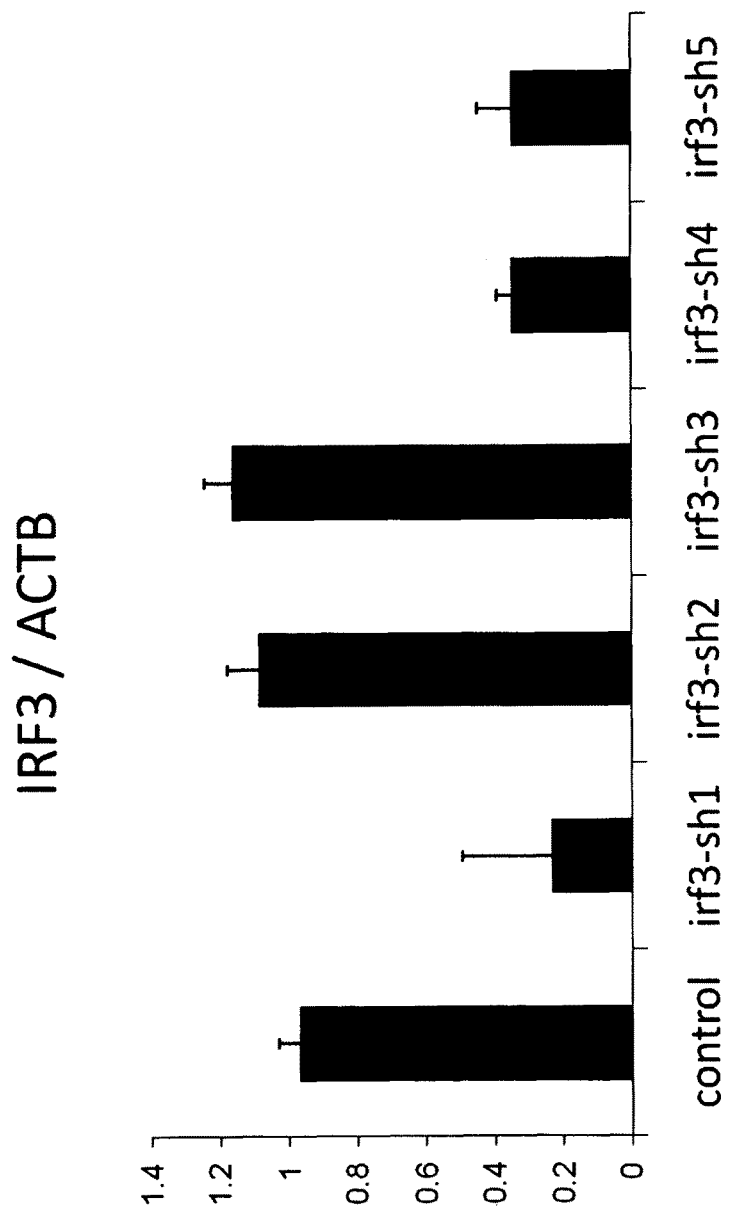

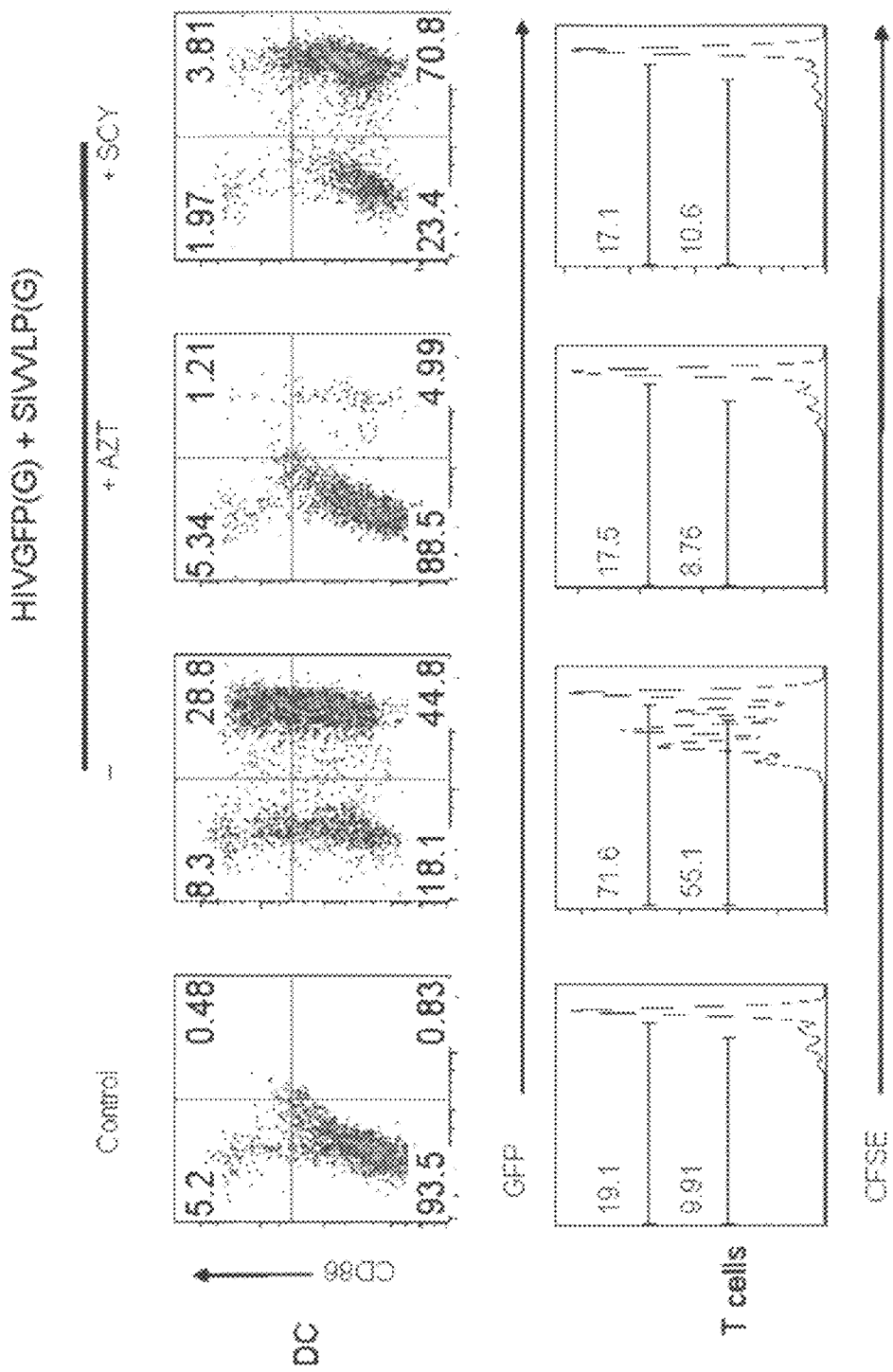

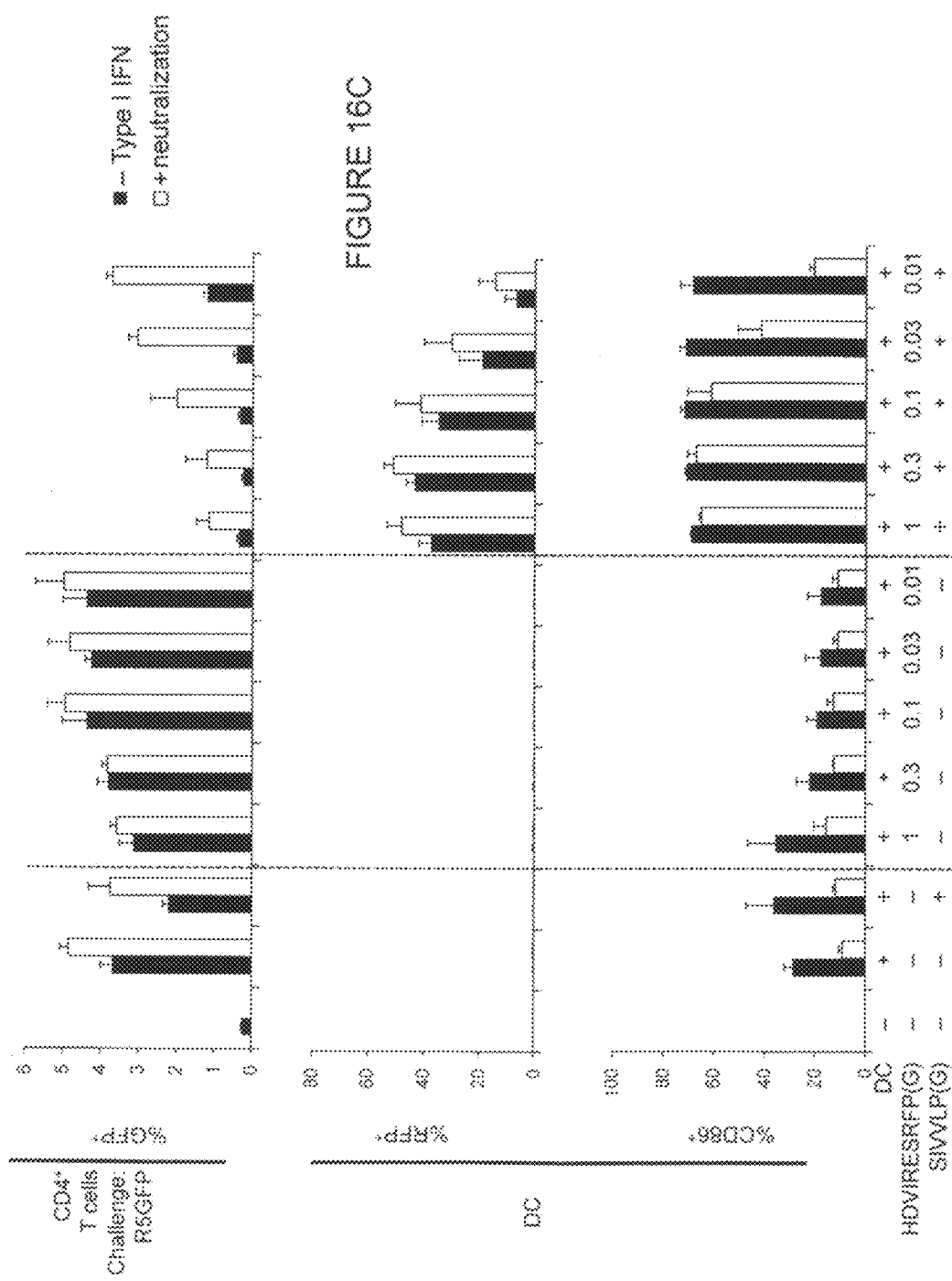

US 9,358,281 B2

METHODS, AGENTS AND PEPTIDES FOR INDUCING AN INNATE IMMUNE RESPONSE IN HIV VACCINATION

CROSS REFERENCE TO RELATED APPLICATION

This application claims priority under 35 USC §119(e) from U.S. Provisional Application Ser. No. 61/278,759, filed Oct. 9, 2009 and U.S. Provisional Application Ser. No. 61/402,336, filed Aug. 27, 2010, and which applications are herein specifically incorporated by reference in their entirety.

GOVERNMENTAL SUPPORT

The research leading to the present invention was supported, at least in part, by National Institutes of Health Grant No. AI33856. Accordingly, the Government has certain rights in the invention.

FIELD OF THE INVENTION

The present invention relates to enhancing, modulating or stimulating the innate immune response to HIV and other viral pathogens and to the modulation and application of immune modulators and peptides for HIV or other pathogen vaccines. The invention relates to methods and means to activate an innate response to HIV utilizing or via the HIV capsid protein or peptide, including modulating the binding of cyclophilin A to HIV capsid protein and modulating the ability of HIV to activate the major innate transcription factor IRF3 and interferon. Methods and assays for screening for compounds, agents, or peptides capable of enhancing or activating innate immune response, particularly to HIV, are included.

BACKGROUND OF THE INVENTION

Our understanding of how HIV interacts with the immune system in humans remains limited, and this has impeded development of strategies to elicit effective protective immunity and to reduce pathogenic effects of the virus. While the T cell response to HIV has been studied extensively in humans, the role of cells involved in the innate response to HIV and other retroviruses has received relatively little attention. Dendritic cells (DC) play a major role in detecting and initiating the response to pathogens, thus linking the innate immune response to adaptive immunity. They serve as early response sensors of microbial infection and also as specialized antigen presenting cells in the induction of T cell responses (Steinman and Hemmi, 2006) (Takeuchi and Akira, 2007a). They are also likely to play a major role in the innate response to HIV: there is a dense network of DC at mucosal surfaces where HIV enters the organism and replicates extensively early after transmission (Niess et al., 2005; Veazey and Lackner, 2003), and the function of these cells in immune responses to pathogenic and commensal microorganisms has only recently begun to be explored.

In recent years, it has been recognized that there are multiple types of DC, including myeloid DC and plasmacytoid DC, which differ in both pathogen recognition mechanisms and in effector functions (Colonna et al., 2004; Cao and Liu, 2007). At mucosal surfaces, particularly in the intestinal lamina propria and in gut-draining lymph nodes, there are myeloid DC with distinct phenotypes that can elicit either inflammatory or tolerogenic responses in T cells. These distinct DC subsets have been studied most extensively in the mouse, in which they can be subdivided into $CX_3CR1^{hi}CD103^-$ cells that produce abundant IL-6 and IL-23 and $CX3CR1^{lo}CD103^+$ cells that produce retinoic acid and induce the differentiation of $Foxp3^+$ regulatory T cells (Coombes et al., 2007; Sun et al., 2007; Mucida et al., 2007). The inflammatory DC have recently also been described in human mesenteric lymph nodes (Jaensson et al., 2008; Moris et al., 2006). The balance of the different types of DC is likely to have a key role in host protection and also in immune system homeostasis, preventing excessive inflammation, particularly in response to normally harmless commensal microorganisms. It should be noted, however that the functions proposed for the diverse subsets of DC are based largely on in vitro studies, and have not been confirmed in mice or humans.

Dendritic Cells and HIV Infection

Several aspects of HIV interactions with DC have been studied. It was noted early by Steinman and colleagues that DC potentiate infection of co-cultured T cells with HIV-1 without themselves being infected (Cameron et al., 1992b). DC have been shown to mediate HIV capture in endocytic-like compartments, which can lead either to infectious transfer to T cells or to degradation and possibly antigen presentation on MHC molecules (Wu and KewalRamani, 2006). DC express HIV receptors (CD4 and CCR5), which allows HIV entry into the cytoplasm to be detected (using assays such as Vpr-Blam) (Cavrois et al., 2006). However, dendritic cells are strikingly resistant to productive HIV infection. In vivo, while macrophages are clearly infected, there is no clear indication that mucosal dendritic cells are infected with HIV (Cameron et al., 1992a). In vitro, monocyte-derived dendritic cells (MDDC, the most extensively characterized model of dendritic cells) are also extremely resistant to HIV infection. In fact, using standard MOI's, infection cannot be detected with single-round HIV-1-based vectors encoding GFP or luciferase (Boggiano et al., 2007). Several publications have reported p24 accumulation in MDDC culture supernatants after 2 weeks of infection, but it is unclear whether p24 originated from MDDC or other cells or whether it was derived from true infection events (i.e. integrative) (Turville et al., 2004). It has been reported that low levels of HIV-1 transduction of MDDC can be achieved when high MOIs, i.e. at least 10, are used (Goujon et al., 2003; Negre et al., 2000). The resistance, which thus appears saturable by high amounts of virus, is reminiscent of classical Fv1 restriction of MLV (Duran-Troise et al., 1977; Goff, 1996). Using a GFP reporter virus, we have indeed confirmed that extremely high MOI of virus obtained by ultracentrifugation can lead to detectable events of infection by flow cytometry (Manel and Littman, unpublished). It is thus likely that MDDC possess strong native restriction to HIV-1 infection.

Recent progress has contributed to a better understanding of DC restriction to HIV-1 replication. It was found that while HIV-1 vectors were unable to infect DC, SIVmac vectors were fully capable of doing so (Mangeot et al., 2000). SIVmac and HIV-2 encode Vpx, a protein that is absent in HIV-1 and that is essential for effective infection of DC, but not T cells, by Sly. Remarkably, infection of MDDC with Vpx-harboring SIVmac virus-like particles (SIVmac VLP) rendered the cells susceptible to HIV infection (Goujon et al., 2006). Recently, Vpx-containing VLPs were also found to enhance production of full-length cDNA with feline and murine retroviruses (Goujon et al., 2007). Thus, Vpx appears to inactivate one or more host cell factors that restrict replication of HIV-1 and other retroviruses in MDDC (and, to a lesser extent, in macrophages). Using cell-fusion assays, it has further been shown that the Vpx-sensitive factor is dominant in endowing cells with resistance to infection with HIV-1

(Sharova et al., 2008). Replication of HIV-1 in dendritic cells is abrogated early after viral entry, before reverse transcription is completed (and thus resembles restriction by TRIM5a). Vpx has been shown to interact with DCAF1, which, in turn, binds to the DDB1/CUL4 E3 ligase complex. A functional role for this interaction is suggested by the finding that siRNA-mediated knockdown of DCAF1 in primary macrophages resulted in substantially reduced transduction efficiency by SIVmac239 (Srivastava et al., 2008). However, another recent study has questioned the requirement for DCAF1 association with Vpx in Vpx-dependent infection of differentiated THP-1 cells and, to a lesser extent, MDDC (Goujon et al., 2008). Moreover, the DCAF1 complex is broadly expressed and is not restricted to monocyte lineage cells. It is therefore highly likely that one or more factors whose expression is restricted to DC, and not T cells, is responsible for the early block of HIV replication in DC.

Although DCs are largely resistant to productive infection with HIV-1, they have the remarkable ability to enhance in trans infection of activated CD4$^+$ T cells. In vitro studies have shown that, when HIV is incubated at low MOI with T cells, inclusion of MDDC results in much more efficient infection of the T cells (Cameron et al., 1992b; Geijtenbeek et al., 2000). The mechanism for trans-infection has been a subject of some controversy. Initial studies indicated that the C-type lectin DC-SIGN was required for DC-mediated enhancement (Geijtenbeek et al., 2000; Kwon et al., 2002), but recently we and others have shown that this is not an essential requirement and there are likely multiple DC surface molecules that interact with the HIV envelope to mediate viral internalization and enhanced infection of T cells (Boggiano et al., 2007; Gummuluru et al., 2003). We had shown that HIV that is transmitted from DC to T cells is taken up by DC into a protease-resistant non-lysosomal compartment (Kwon et al., 2002). Another recent report argued that only surface-bound protease-sensitive and soluble CD4-sensitive virus is transmitted from DC to T cells (Cavrois et al., 2007). In that report, however, high virus titers were employed, and the phenomenon resembled that observed when RAJI cells transfected with DC-SIGN were used in place of the DC. It has been suggested that virus is taken up into compartments that remain contiguous with the plasma membrane, allowing access to inhibitory molecules such as soluble CD4. This interpretation is consistent with the more recent finding that HIV is taken up into a novel compartment adjacent to the plasma membrane (Yu et al., 2008). It has been proposed that virus may be carried by lipid rafts on the plasma membrane towards a synapse with T cells (Cavrois et al., 2008). What is clear at this point is that DCs are endowed with a specialized means to enhance the infectivity of T cells with HIV, but the mechanism for this process remains obscure. Moreover, the significance of this DC function in vivo has yet to be explored. Thus, the contribution of mucosal DC to the explosive rapid replication of HIV-1 and SIV in intestinal lamina propria T cells shortly after infection of humans and non-human primates, respectively, has yet to be examined.

Innate Anti-Viral Response Mechanisms

During the past decade, there has been renewed appreciation of the importance of innate immunity in protection from microbial infections. Innate immune responses, which are evolutionarily much more ancient than adaptive responses found in vertebrates (Hoffmann and Reichhart, 2002), can directly limit the replication of infectious agents and also act indirectly by activating B and T cell responses (Medzhitov, 2007). Mechanisms of innate immunity include recognition of pathogen-associated molecular patterns by Toll-like receptors (TLRs), lectin family receptors, cytoplasmic NOD/NALP-like receptors (NLRs), and cytoplasmic helicase domain proteins such as RIG-I and MDA5 (RLHs) (Takeuchi and Akira, 2007b) (Takeda and Akira, 2005) (Stetson and Medzhitov, 2006). Despite substantial progress in understanding innate responses to bacteria, fungi, and many viruses, there is little known of vertebrate innate immune responses that limit replication of retroviruses. It has been proposed that the single-strand RNA-detecting TLR7 is involved in responses to HIV, but evidence is limited to the ability of viral RNA to elicit a TLR7-mediated response, and there is little evidence that HIV particles can trigger such a response on their own (Beignon et al., 2005). Cytoplasmic helicase domain proteins RIG-I and MDA5 have essential roles in antiviral innate responses in a variety of cells other than plasmacytoid DC. These molecules have been shown to be important in responses against several RNA viruses. RIG-I is activated by non-capped RNAs that have a 5' terminal triphosphate and polyuridine or polyriboadenine motifs in the 3' UTRs (Hornung et al., 2006; Saito et al., 2008). The role of the RLHs in anti-retroviral innate immunity has not been reported, and the genomic retroviral messenger RNA is 5' capped. Recognition of cytoplasmic DNA may also be expected to constitute a mechanism of innate immunity against retroviruses. A sensor for cytoplasmic DNA, DAI, was described recently, but it is likely that there are multiple such recognition molecules (Takaoka et al., 2007). The potential importance of this and other cytoplasmic DNA sensors is highlighted by recent studies on the cytoplasmic 3'-5' ssDNA exonuclease Trex1. Defects in the gene encoding Trex1 have been shown to be linked to Aicardi-Goutieres Syndrome, an inflammatory disease of the nervous system, and mice with deficiency of Trex1 have autoimmune myocarditis. It has now been shown that, in the absence of Trex1, there is an increase in DNA retroelements in the cytoplasm, activation of IRF3, and increased production of type I interferon (Stetson et al., 2008). The autoimmune myocarditis is mediated by the adaptive immune response, since Trex1-deficient mice that also lack RAG2 have no disease. The retroelements likely activate innate immune recognition machinery, including DAI. These recent results suggest that Trex1, and related members in the family of cytoplasmic exonucleases, degrade cytoplasmic DNA that is generated by reverse transcription of endogenous retroelements and thus prevent abnormal activation of innate immune responses and production of interferons and other effector cytokines. In addition to preventing inflammation, Trex1 may also protect cells from reverse transcribed DNA generated from infections with retroviruses. Thus, a better understanding of how b-interferon is induced in the absence of Trex1 (or related exonucleases expressed in tissues other than myocardium) may provide insight into the mechanism by which host cells sense retrovirus components in the cytoplasm and transmit the information to the adaptive immune system.

Some insight into innate immune system requirements for activation of an adaptive anti-retroviral immune response has come from studies in mice of infection with the Friend virus (FV), a complex retrovirus that is widely used as a model for understanding anti-retroviral immune responses and mechanisms of persistent infection (Hasenkrug and Chesebro, 1997; Miyazawa et al., 2008). FV consists of a mixture of a helper virus and a defective virus that encodes gp55, which interacts with erythropoietin receptor and drives proliferation of erythroblasts. In C57BL/6 mice, infection is followed by peak viral titers in the spleen at 7 dpi and resolution to a low level persistent viremia. During the acute phase of infection, the virus is controlled by both T cell and B cell responses that follow an early peak in type I interferon production (Gerlach et al., 2006). We have investigated the roles played by dendritic cells and by the TLR signaling pathway in control of FV infection in mice. Both DC and the Myd88 signaling pathway, employed by all TLRs except for TLR3, were required for generation of an antiviral antibody response (Browne and Littman, 2009). It remains unclear whether the Myd88 signal is required in DC and whether a known TLR interacts with a feature of the retroviral infection that serves as a PAMP (pathogen-associated molecular pattern) to set the innate response into motion. It is also not known whether TLR signaling is important in activation of an adaptive immune response following infection with HIV.

Relationship Between Infection of Dc with HIV-1 and Activation of an Innate Immune Response Although it has not yet been feasible to perform studies in humans to investigate the in vivo role for DCs following HIV infection, it is highly likely that these cells perform key functions in mounting an innate immune response to limit viral replication. A better understanding of how innate responses are initiated and how they function after HIV infection is critical for achieving better vaccine strategies. Because DCs are the most potent cell type for initiation of innate immune responses, particularly for activating antigen-specific T cells, the means by which HIV interacts with DCs is likely to be crucial for setting the quality and quantity of innate immunity. A key question that arises is whether exposure of DCs to HIV-1 under conditions of productive infection versus nonproductive enhancement of T cell infection results in different outcomes in terms of activation of DC innate functions. A few attempts have been made to address related questions in various systems (Boasso et al., 2008; Fantuzzi et al., 2004; Goujon et al., 2006; Granelli-Piperno et al., 2004; Smed-Sorensen et al., 2005; Smed-Sorensen et al., 2004). However, in the absence of Vpx, the rare infection events observed with HIV-1 did not appear to activate DC, but the efficiency of infection was so low (1%) that it is risky to interpret this result conclusively (Granelli-Piperno et al., 2004). In the presence of Vpx, transduction of minimal lentiviral vector devoid of the expression of viral proteins did not seem to induce MDDC activation (Goujon et al., 2006). It would be useful to determine whether resistance of DCs to infection with HIV-1 is beneficial to the host, potentially limiting spread of the virus, or detrimental, due to limitation in the level of innate immune system activation that can result in stronger anti-viral B and T cell responses.

The interactions of HIV and SIV with the host innate immune system may explain, at least in part, the puzzling differences between individuals (and different non-human primate species) in their ability to contain the infection and avoid immune deficiency. Characterization of host genes and proteins involved in regulating myeloid cell infection and the host innate anti-viral immune response may provide clues that can be applied to the future investigation of how individual variation can explain host susceptibility to HIV disease.

Thus, while the innate response to several viruses is known, the response to HIV-1 has remained elusive. A better understanding of innate immune response to HIV-1 and a knowledge of the molecules or markers involved would be useful, particularly in designing, generating, and developing HIV vaccines or in stimulating responses to HIV in infected or at risk individuals. Accordingly, it would be desirable to identify molecules or targets involved in innate response to HIV and HIV-like pathogens and to provide novel molecules and methods for improving HIV vaccine strategies and it is toward the achievement of these objectives that the present invention is directed.

The citation of references herein shall not be construed as an admission that such is prior art to the present invention.

SUMMARY OF THE INVENTION

The invention relates generally to methods and agents for inducing and evaluating the innate immune response to HIV-1. Current HIV-1 vaccines strategies have failed at eliciting protective immunity and ignore the innate aspect of the immune response, relying on classical adjuvant and/or on unrelated viral vectors to drive the initial innate response. The present invention now provides indicators of innate immune response to HIV, methods for stimulating or facilitating immune response to HIV, and assays for screening and identifying agents, compounds or peptides to modulate immune response to HIV. The method of the invention leads to methods of upregulating activation markers, including co-stimulatory molecules for effective activation of T cells, and secretion of type-I interferon by dendritic cells. The assays of the invention are based on the up-regulation of activation markers, including co-stimulatory molecules for effective activation of T cells, and to the secretion of type-I interferon by dendritic cells. The methods, agents and assays of the invention can be implemented in vaccine strategies and the stimulation of immune response to HIV.

Thus, a purpose of the present method is to induce the innate response to HIV-1 along with, or in the absence of, other adaptive responses. Triggering the innate response to HIV-1 should then shape adaptive immune responses so that T and B cells are polarized appropriately for HIV-1. This method thus provides a means to overcome earlier failures to develop vaccines.

The present method demonstrates that Cyclophilin A binding plays a critical role in the activation of DCs (monocyte-derived dendritic cells) on HIV infection. Cyclosporin A treatment prevents activation. Cyclophilin A binds HIV GAG protein, particularly p24 capsid protein, particularly via a cyclophilin binding peptide corresponding to position 213 to 237 of Gag polyprotein. In a particular embodiment, a cyclophilin binding peptide comprises or consists of the sequence of DRLHPVHAGPIAPGQMREPRGSDIA (SEQ ID NO: 15) or DRVHPVHAGPIAPGQMREPRGSDIA (SEQ ID NO: 16). The method demonstrates that mutant Gag proteins which disrupt Cyclophilin binding do not induce activation. Other mutant Gag proteins are herein identified that enhance activation. Therefore, in an aspect of the invention, Gag proteins or peptides which facilitate or promote activation may be utilized in modulating and enhancing activation and immune response to HIV antigens of HIV infection. Gag or capsid protein, polypeptide or cyclophilin binding regions or peptides thereof may be utilized to enhance innate immunity. The Gag proteins or peptides of the invention may be provided as naked DNA, in any of various vectors, as monomers, multimers, dendrimers, or peptide fusions. One or more Gag proteins or peptides from HIV subtypes, variants, or mutants may be combined to enhance immune response. The peptides may be combined with, associated with, covalently attached to or fused to other immune modulators, including interferons, interleukins, T or B cell antigens or stimulators, other activators, or adjuvant molecules.

The method provides proteins and peptides, particularly HIV gag peptides or proteins which have application and use, alone or in combination with other immune system modulators, T cell modulators, antibodies, vaccines, antigens, or chemotherapeutics for stimulating, facilitating or enhancing desired innate immune system or immune cell actions or activities, particularly to HIV, including antigen response, vaccine response, anti-HIV response.

Accordingly, also encompassed herein is a composition comprising these peptides, particularly HIV gag peptides or proteins which have application and use, alone or in combination with other immune system modulators, T cell modulators, antibodies, vaccines, antigens, or chemotherapeutics and a pharmaceutically acceptable buffer, for use in treating a patient with HIV-1, wherein said composition alleviates symptoms of HIV infection in the patient with HIV when administered to the patient in a therapeutically effective amount. Such compositions also have utility for use in prophylaxis for a patient at risk for exposure to HIV or suspected of being exposed to HIV wherein said composition prevents or alleviates symptoms of a potential subsequent HIV infection in the patient when administered to the patient in a therapeutically effective amount. Also encompassed herein is the use of a therapeutically effective amount of a composition comprising proteins and peptides, particularly HIV gag peptides or proteins which have application and use, alone or in combination with other immune system modulators, T cell modulators, antibodies, vaccines, antigens, or chemotherapeutics and a pharmaceutically acceptable buffer in the manufacture of a medicament for treating a patient with HIV or prophylaxis for a patient suspected of being exposed to HIV or at risk for exposure to HIV, wherein the medicament alleviates or prevents symptoms of the HIV-related disorder when administered to the patient.

The present invention includes assay methods and assay systems for screening and identifying modulators, including enhancers of innate immune response, particularly to HIV. Thus, in one aspect, cyclophilin binding domains, peptides, Gag or capsid may be utilized in assay to identify compounds, agents, peptides which bind or otherwise interact therewith. Alternatively or additionally, activation markers, such as but not limited to one or more of CD86, CD80, CD38, CD83 may be utilized as indicators for screening to identify or characterize compounds, agents, peptides which facilitate activation. In a further aspect, interferon production or induction of Type-I interferon response signature genes may be utilized in an assay to identify or characterize compounds, agents, peptides which facilitate activation and/or innate response to HIV infection. Activation of adaptive immunity, as reflected in an increase in at least one of HIV-specific CD4+ T cells, HIV-specific CD8+ T cells, or naive CD4+ T cells (e.g., numbers and/or activity), may also be utilized in an assay to identify or characterize compounds, agents, peptides which facilitate activation and/or innate response to HIV infection. Assays designed to assess inhibition of trans-infection of CD4+ T cells also offer useful methods for identifying or characterizing such compounds, agents, or peptides. In one aspect, assays may be performed using dendritic cells, including MDCCs. In other aspects immune cells may be utilized, or cell cultures comprising immune cells, including dendritic cells.

The diagnostic utility extends to the use of the activation markers, including CD86, CD80, CD38, CD83, interferon production, or induction of Type-I interferon response signature genes in assays to characterize immune response or immune cell activation response to HIV. The diagnostic utility further extends to the use of methods for detection/measurement of HIV-specific CD4+ T cells, HIV-specific CD8+ T cells, or naive CD4+ T cells (e.g., numbers and/or activity), and inhibition of trans-infection of CD4+ T cells in assays to characterize immune response or immune cell activation response to HIV. The expression or activity of the markers, and/or cell number/activity may be examined by known techniques, including FACS analysis, immunoassay, RT-PCR, etc which may vary with the nature of the marker, cell type, and/or activity to be measured and are known to the artisan. Such analyses may be conducted in cell systems, in vitro, or in animal model systems, in vivo, or in patient or clinical or vaccine trials or evaluation studies.

In a further embodiment, therapeutic methods are described herein which would be based upon the activity of the cyclophilin binding or immune activator peptides, or upon agents or other drugs determined to possess the same activity. A therapeutic method is associated with the modulation of the immune response, particularly stimulation or enhancement of innate immunity and response to viral antigens and/or infection, particularly of HIV. A further therapeutic method is associated with methods for stimulating immune response to HIV comprising administering the cyclophilin binding or immune activator peptides, or agents or other drugs determined to possess the same activity, alone or in combination with HIV antigens or immunogens, or other immune modulators, including adjuvants, for generating an immunogenic and/or protective response to HIV. In one aspect of this method, the cyclophilin binding or immune activator peptides, or agents or other drugs determined to possess the same activity, are administered to individuals exposed to or at risk of exposure to HIV. In a further aspect, the cyclophilin binding or immune activator peptides, or agents or other drugs determined to possess the same activity are administered to an HIV-infected individual to stimulate immune response and clearance of the virus.

Accordingly, also encompassed herein is a composition comprising cyclophilin binding or immune activator peptides, or upon agents or other drugs determined to possess the same activity, and a pharmaceutically acceptable buffer, for use in treating a patient with HIV, wherein said composition alleviates symptoms of HIV infection in the patient with HIV when administered to the patient in a therapeutically effective amount. Such compositions also have utility for use in prophylaxis for a patient at risk for exposure to HIV or suspected of being exposed to HIV wherein said composition prevents or alleviates symptoms of a potential subsequent HIV infection in the patient when administered to the patient in a therapeutically effective amount. Also encompassed herein is the use of a therapeutically effective amount of a composition comprising cyclophilin binding or immune activator peptides, or upon agents or other drugs determined to possess the same activity, and a pharmaceutically acceptable buffer in the manufacture of a medicament for treating a patient with HIV or prophylaxis for a patient suspected of being exposed to HIV or at risk for exposure to HIV, wherein the medicament alleviates or prevents symptoms of the HIV-related disorder when administered to the patient.

In an aspect, methods are provided for stimulating immune response to HIV wherein a protein or peptide comprising the cyclophilin binding domain of HIV Gag protein is administered or provided in a vaccine or immunogenic composition, in combination with a vaccine or immunogenic composition, or prior or subsequent to a vaccine or immunogenic composition. In one such aspect the protein or peptide comprising the cyclophilin binding domain of HIV Gag protein comprises a cyclophilin binding peptide sequence corresponding to position 213 to 237 of Gag polyprotein. In a particular embodiment the cyclophilin binding peptide comprises or consists of the sequence of DRLHPVHAGPIAPGQM-REPRGSDIA SE ID NO: 15) or DRVHPVHAGPIAPGQM-REPRGSDIA (SEQ ID NO: 16). In an additional aspect, the cyclophilin binding peptide, Gag protein, or Capsid protein may be combined with or administered in conjunction with (including before, after, or simultaneously) an agent, compound or peptide capable of binding the cyclophilin binding peptide and/or capable of increasing or activating the expression of one or more of CD86, CD80, CD38, CD83, interferon, and a Type-I interferon response signature gene, increasing numbers and/or activity of HIV-specific CD4+ T cells, HIV-specific CD8+ T cells, or naive CD4+ T cells, and inhibition of trans-infection of CD4+ T cells.

Also encompassed herein is a composition comprising a protein or peptide comprising the cyclophilin binding domain of HIV Gag protein and a pharmaceutically acceptable buffer, for use in treating a patient with HIV, wherein said composition alleviates symptoms of HIV infection in the patient with HIV when administered to the patient in a therapeutically effective amount. Such compositions also have utility for use in prophylaxis for a patient at risk for exposure to HIV or suspected of being exposed to HIV wherein said composition prevents or alleviates symptoms of a potential subsequent HIV infection in the patient when administered to the patient in a therapeutically effective amount. Also encompassed herein is the use of a therapeutically effective amount of a composition comprising a protein or peptide comprising the cyclophilin binding domain of HIV Gag protein and a pharmaceutically acceptable buffer in the manufacture of a medicament for treating a patient with HIV or prophylaxis for a patient suspected of being exposed to HIV or at risk for exposure to HIV, wherein the medicament alleviates or prevents symptoms of the HIV-related disorder when administered to the patient.

Also encompassed herein is a composition comprising a cyclophilin binding peptide, Gag protein, or Capsid protein in combination with or administered in conjunction with (including before, after, or simultaneously) an agent, compound or peptide capable of binding the cyclophophilin binding peptide and/or capable of increasing or activating the expression of one or more of CD86, CD80, CD38, CD83, interferon, and a Type-I interferon response signature gene, and a pharmaceutically acceptable buffer, for use in treating a patient with HIV, wherein said composition alleviates symptoms of HIV infection in the patient with HIV when administered to the patient in a therapeutically effective amount. Such compositions also have utility for use in prophylaxis for a patient at risk for exposure to HIV or suspected of being exposed to HIV wherein said composition prevents or alleviates symptoms of a potential subsequent HIV infection in the patient when administered to the patient in a therapeutically effective amount. Also encompassed herein is the use of a therapeutically effective amount of a composition comprising the cyclophilin binding peptide, Gag protein, or Capsid protein in combination with or administered in conjunction with (including before, after, or simultaneously) an agent, compound or peptide capable of binding the cyclophophilin binding peptide and/or capable of increasing or activating the expression of one or more of CD86, CD80, CD38, CD83, interferon, and a Type-I interferon response signature gene, and a pharmaceutically acceptable buffer in the manufacture of a medicament for treating a patient with HIV or prophylaxis for a patient suspected of being exposed to HIV or at risk for exposure to HIV, wherein the medicament alleviates or prevents symptoms of the HIV-related disorder when administered to the patient.

In a further aspect, methods are presented for stimulating or enhancing innate immune response to HIV-1 comprising administering in a vaccine or immunogenic composition a protein or peptide comprising the cyclophilin binding domain of HIV Gag protein alone or in combination with at least one viral protein or peptide encoded by HIVGFP (SEQ ID NO: 1); HIVGFP viral particles and derivatives thereof; or a nucleic acid sequence comprising part or all of HIVGFP (SEQ ID NO: 1). In a particular embodiment, the protein or peptide comprises or consists of the sequence of DRLHPVHAGPIAPGQMREPRGSDIA (SEQ ID NO: 15) or DRVHPVHAGPIAPGQMREPRGSDIA (SEQ ID NO: 16). In certain embodiments, the protein or peptide may be associated with or covalently attached to a polycationic or cell penetrating peptide to promote cellular uptake or delivery. A Tat peptide comprising the sequence RKKRRQRRR is set forth as an exemplary agent for promoting cellular uptake or delivery. In a particular embodiment, dendritic cells are targeted for cellular uptake or delivery. Assessment of dendritic cell activation may be accomplished, as described herein, by evaluating expression of one or more of CD86, CD80, CD38, CD83, interferon, and a Type-I interferon response signature gene. The instant methods may further comprise assessing adaptive immunity, wherein adaptive immunity activation is detected as an increase in at least one of HIV-specific CD4+ T cells, HIV-specific CD8+ T cells, or naive CD4+ T cells. Inhibition of CD4+ T cell trans-infection may also be utilized as an indicator or read-out of the instant methods. In an embodiment of the instant methods, the at least one viral protein or peptide encoded by HIVGFP is HIV tat (SEQ ID NO: 2), HIV rev (SEQ ID NO: 3), HIV gag (SEQ ID NO: 4), or HIV gagpol (SEQ ID NO: 5). The instant methods also encompass embodiments wherein the nucleic acid sequence comprising part or all of HIVGFP (SEQ ID NO: 1) is a deoxyribonucleic acid sequence or a ribonucleic acid transcribed therefrom. In particular embodiments, the deoxyribonucleic acid sequence encodes at least one of HIV tat (SEQ ID NO: 2), HIV rev (SEQ ID NO: 3), HIV gag (SEQ ID NO: 4), or HIV gagpol (SEQ ID NO: 5), or is HIVGFP (SEQ ID NO: 1). Ribonucleic acid sequences encoding at least one of HIV tat (SEQ ID NO: 2), HIV rev (SEQ ID NO: 3), HIV gag (SEQ ID NO: 4), or HIV gagpol (SEQ ID NO: 5) are also envisioned, as is the ribonucleic acid sequence transcribed from HIVGFP (SEQ ID NO: 1) or SEQ ID NO: 10.

Also encompassed herein is a composition comprising a protein or peptide comprising the cyclophilin binding domain of HIV Gag protein alone or in combination with at least one viral protein or peptide encoded by HIVGFP (SEQ ID NO: 1); HIVGFP viral particles and derivatives thereof; or a nucleic acid sequence comprising part or all of HIVGFP (SEQ ID NO: 1) and a pharmaceutically acceptable buffer, for use in treating a patient with HV-1, wherein said composition alleviates symptoms of HIV infection in the patient with HIV-1 when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising a protein or peptide comprising the cyclophilin binding domain of HIV Gag protein alone or in combination with at least one viral protein or peptide encoded by HIVGFP (SEQ ID NO: 1); HIVGFP viral particles and derivatives thereof; or a nucleic acid sequence comprising part or all of HIVGFP (SEQ ID NO: 1) and a pharmaceutically acceptable buffer in the manufacture of a medicament for treating a patient with HIV-1 or prophylaxis for a patient suspected of being exposed to HIV-1 or at risk for exposure to HIV-1, wherein the medicament alleviates or prevents symptoms of the HIV-related disorder when administered to the patient.

In a further aspect, methods are presented for stimulating or enhancing innate immune response to HIV-1 comprising administering in a vaccine or immunogenic composition a first vector comprising a nucleic acid encoding a protein or peptide comprising the cyclophilin binding domain of HIV Gag protein alone or in combination with a second vector comprising a second nucleic acid encoding at least one viral protein or peptide of HIVGFP (SEQ ID NO: 1). In alternate embodiment, a single vector comprises the nucleic acid encoding a protein or peptide comprising the cyclophilin binding domain of HIV Gag protein and the second nucleic acid encoding at least one viral protein or peptide of HIVGFP (SEQ ID NO: 1). In a particular embodiment, the protein or peptide comprises or consists of the sequence of DRLH-PVHAGPIAPGQMREPRGSDIA (SEQ ID NO: 15) or DRVHPVHAGPIAPGQMREPRGSDIA (SEQ ID NO: 16). In a further embodiment, the protein or peptide comprising the cyclophilin binding domain of HIV Gag protein is HIV gag (SEQ ID NO: 4). In certain embodiments, the at least one viral protein or peptide of HIVGFP (SEQ ID NO: 1) is HIV tat (SEQ ID NO: 2), HIV rev (SEQ ID NO: 3), HIV gag (SEQ ID NO: 4), or HIV gagpol (SEQ ID NO: 5). In a particular embodiment, the second vector is HIVGFP (SEQ ID NO: 1).

Also encompassed herein is a composition comprising a first vector comprising a nucleic acid encoding a protein or peptide comprising the cyclophilin binding domain of HIV Gag protein alone or in combination with a second vector comprising a second nucleic acid encoding at least one viral protein or peptide of HIVGFP (SEQ ID NO: 1) or a single vector comprising the nucleic acid encoding a protein or peptide comprising the cyclophilin binding domain of HIV Gag protein and the second nucleic acid encoding at least one viral protein or peptide of HIVGFP (SEQ ID NO: 1), and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV infection in the patient when administered to the patient in a therapeutically effective amount. Also encompassed herein is the use of a therapeutically effective amount of a composition comprising a first vector comprising a nucleic acid encoding a protein or peptide comprising the cyclophilin binding domain of HIV Gag protein alone or in combination with a second vector comprising a second nucleic acid encoding at least one viral protein or peptide of HIVGFP (SEQ ID NO: 1) or a single vector comprising the nucleic acid encoding a protein or peptide comprising the cyclophilin binding domain of HIV Gag protein and the second nucleic acid encoding at least one viral protein or peptide of HIVGFP (SEQ ID NO: 1), and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

Also encompassed herein are methods for stimulating or enhancing innate immune response to HIV-1 comprising administering in a vaccine or immunogenic composition a replication defective HIV vector encoding at least one HIV-1 Gag polypeptide or one HIV-2 Gag polypeptide comprising the cyclophilin binding domain, wherein the replication defective vector is missing at least one gene or activity essential for HIV-1 or HIV-2 replication and/or budding. Such a replication defective vector is not capable of encoding live, infectious HIV-1 or HIV-2. Exemplary replication defective HIV vectors include an envelope-deficient HIV vector or PTAP-mutant, wherein a mutation inactivates the PTAP motif in p6, such as mutating to LIRL. Exemplary replication defective HIV vectors include: envelope-deficient HIV-2 vectors; and replication defective HIV-1 vectors, including vif-deficient, vpr-deficient, vpu-deficient, and nef-deficient HIV-1 vectors. Such replication defective HIV vectors are known to those skilled in the art.

Also encompassed herein is a composition comprising a replication defective HIV vector encoding at least one HIV-1 Gag polypeptide or one HIV-2 Gag polypeptide comprising the cyclophilin binding domain, wherein the replication defective vector is missing at least one gene or activity essential for HIV-1 or HIV-2 replication and/or budding, and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising a replication defective HIV vector encoding at least one HIV-1 Gag polypeptide or one HIV-2 Gag polypeptide comprising the cyclophilin binding domain, wherein the replication defective vector is missing at least one gene or activity essential for HIV-1 or HIV-2 replication and/or budding, and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

In a further aspect, methods are presented for stimulating or enhancing innate immune response to HIV-1 comprising administering in a vaccine or immunogenic composition a Vpx-Vpr fusion protein alone or in combination with at least one viral protein or peptide encoded by HIVGFP (SEQ ID NO: 1), and detecting at least one of dendritic cell activation or suppression of viral replication in T cells, wherein the dendritic cell activation or suppression of viral replication in T cells is positively correlated with stimulation or enhancement of the innate immune response to HIV-1. The at least one viral protein or peptide encoded by HIVGFP may be HIV tat (SEQ ID NO: 2), HIV rev (SEQ ID NO: 3), HIV gag (SEQ ID NO: 4), or HIV gagpol (SEQ ID NO: 5).

Also encompassed herein is a composition comprising a Vpx-Vpr fusion protein alone or in combination with at least one viral protein or peptide encoded by HIVGFP (SEQ ID NO: 1) and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV infection in the patient when administered to the patient in a therapeutically effective amount. Also encompassed herein is the use of a therapeutically effective amount of a composition comprising a Vpx-Vpr fusion protein alone or in combination with at least one viral protein or peptide encoded by HIVGFP (SEQ ID NO: 1), and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

Methods for stimulating or enhancing innate immune response to HIV-1 in a subject infected with HIV-1 are also encompassed herein, such methods comprising administering in a vaccine or immunogenic composition a Vpx-Vpr fusion protein, a Vpx protein, or SIVVLP(G), and detecting at least one of dendritic cell activation or suppression of viral replication in T cells, wherein the dendritic cell activation or suppression of viral replication in T cells is positively correlated with stimulation or enhancement of the innate immune response to HIV-1.

Also encompassed herein is a composition comprising a Vpx-Vpr fusion protein, a Vpx protein, or SIVVLP(G) and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV infection in the patient when administered to the patient in a therapeutically effective amount. Also encompassed herein is the use of a therapeutically effective amount of a composition comprising a Vpx-Vpr fusion protein, a Vpx protein, or SIVVLP(G) and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

Also encompassed is a method for stimulating or enhancing innate immune response to HIV-1 comprising administering in a vaccine or immunogenic composition a vector comprising a nucleic acid sequence encoding Vpx or Vpx-Vpr fusion protein, and detecting at least one of dendritic cell activation or suppression of viral replication in T cells, wherein the dendritic cell activation or suppression of viral replication in T cells is positively correlated with stimulation or enhancement of the innate immune response to HIV-1. In a particular embodiment, the vector is an HIV-2 derived vector.

Also encompassed herein is a composition comprising a vector comprising a nucleic acid sequence encoding Vpx or Vpx-Vpr fusion protein and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV infection in the patient when administered to the patient in a therapeutically effective amount. Also encompassed herein is the use of a therapeutically effective amount of a composition comprising a vector comprising a nucleic acid sequence encoding Vpx or Vpx-Vpr fusion protein and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

The present invention also includes the cyclophilin binding or immune activator peptides, or agents or other drugs determined to possess the same activity, which are covalently attached to or otherwise associated with other molecules or agents. These other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents.

Also encompassed herein is a composition comprising the cyclophilin binding or immune activator peptides, or agents or other drugs determined to possess the same activity, which are covalently attached to or otherwise associated with other molecules or agents and a pharmaceutically acceptable buffer, for use in treating a patient with HIV, wherein said composition alleviates symptoms of HIV infection in the patient with HIV-1 when administered to the patient in a therapeutically effective amount. As described herein, other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising the cyclophilin binding or immune activator peptides, or agents or other drugs determined to possess the same activity, which are covalently attached to or otherwise associated with other molecules or agents and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

In a further aspect, a method for diagnosing a subject infected with HIV-1 as a controller of HIV-1 infection is presented, the method comprising measuring activity of the innate immune response in the subject, wherein detection of the innate immune response activity is positively correlated with a diagnosis of the subject as the controller of HIV-1 infection. In an embodiment thereof, measuring the activity of the innate immune response may be achieved by measuring the expression or activity of an innate HIV immune response marker, wherein the expression or activity of the innate HIV immune response marker is increased or enhanced. In a particular embodiment, dendritic cell activation may be assessed to determine innate immune response activity, wherein expression of one of more of CD86, CD80, CD38, CD83, interferon, and a Type-I interferon response gene is positively correlated with dendritic cell activation. Exemplary Type-I interferon response signature genes include mx1, cxc10, ifit1 and/or ifit2. Diagnostic methods may further comprise assessing adaptive immunity, wherein activated adaptive immunity is detected as an increase in at least one of HIV-specific CD4+ T cells, HIV-specific CD8+ T cells, or naive CD4+ T cells. Inhibition of trans-infection of CD4+ T cells may also be utilized as an indicator or read-out of the instant methods.

Other objects and advantages will become apparent to those skilled in the art from a review of the ensuing detailed description, which proceeds with reference to the following illustrative drawings, and the attendant claims.

BRIEF DESCRIPTION OF THE DRAWINGS

FIG. 8 shows that activation requires early steps of infection. Addition of AZT or RAL within the first 24 hours of infection blocks activation.

FIG. 11 depicts knock down of IRF3 by shRNA constructs.

FIGS. 16A, 16B, and 16C shows activation of T cells and inhibition of trans-enhancement by MDDC productively infected with HIV-1. (A) GFP and CD86 expression in control and HIV-1-infected DC (top) and CFSE dilution (bottom) in CFSE-labeled naive CD4+ T cells cultured with the DC for four days in the presence of anti-CD3 antibody. (B) GFP and CD86 expression in DC (top) and CFSE dilution (bottom) in naive CD4+ T cells cultured for four days with untreated DC or DC treated with 25 μM AZT or 1 μM SCY after infection. (C) Induction of a type I IFN-dependent antiviral state inhibits MDDC-dependent trans-enhancement. MDDC were infected with dilutions of HDVIRESRFP(G) and SIVVLP (G) in the presence or the absence of type I IFN neutralizing reagents. Activated CD4+ T cells and a CCR5-tropic HIV-1-GFP(R5-GFP) were added 2 days later. RFP and CD86 expression and GFP expression were measured in DC and CD4+ T cells, respectively. Trans-enhancement is indicated by the increase in GFP+ T cells in the presence or absence of MDDC in the top panel.

DETAILED DESCRIPTION

Figure 1:
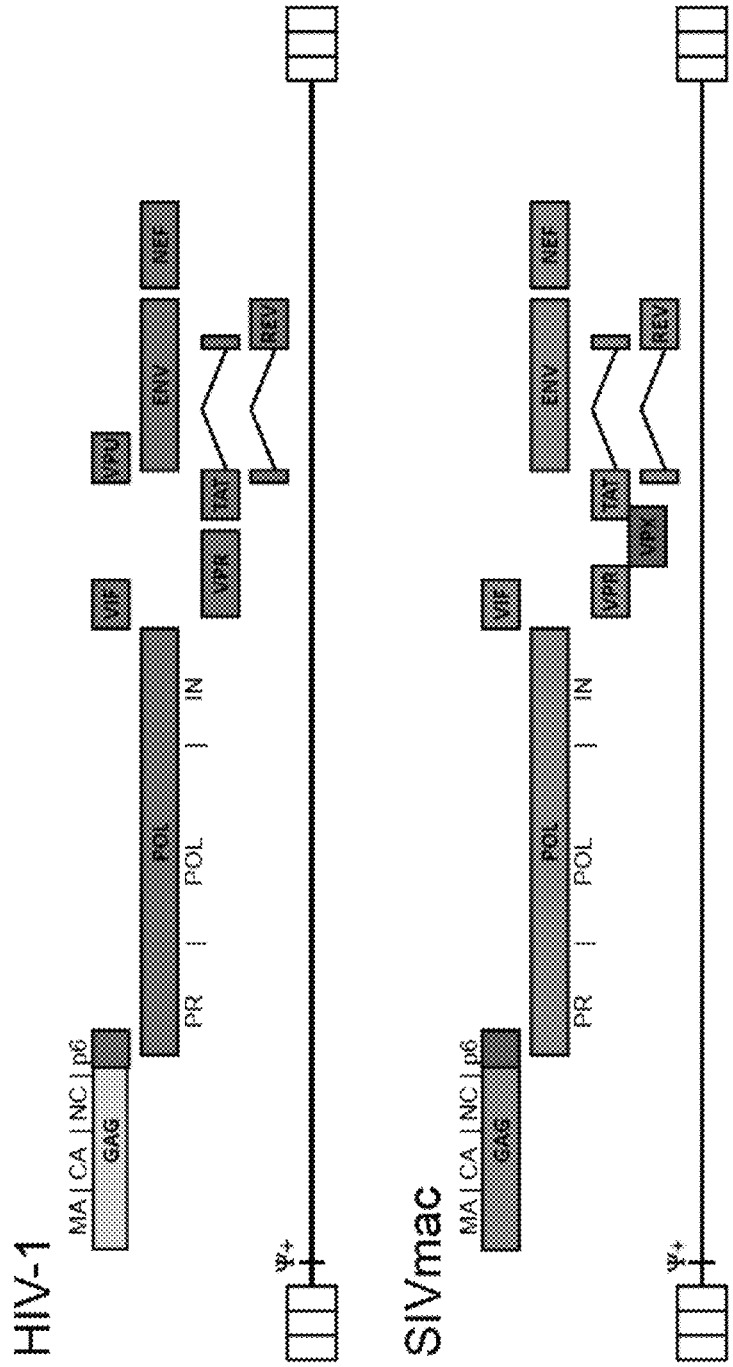
FIG. 1 is a schematic of the HIV and SIV vectors used in the present studies. HIVGFP(G) is a VSV-G-pseudotyped HIV vector derived from NL4-3, encoding GFP in nef, with the genotype env–nef–vif–vpr–vpu–. SIVVLP(G) is VSV-G-pseudotyped SIV vector derived from SIVmac251, with the genotype psi–env–nef–.

Dendritic cells (DC) serve a key function in host defense, linking innate detection of microbes to the activation of pathogen-specific adaptive immune responses (Steinman et al., 2006; Takeuchi et al., 2009). Whether there is cell-intrinsic recognition of HIV-1 by host innate pattern-recognition receptors and subsequent coupling to antiviral T cell responses is not yet known (Stetson et al., 2008). DC are largely resistant to infection with HIV-1 (Negre et al., 2000), but facilitate infection of co-cultured T-helper cells through a process of trans-enhancement (Cameron et al., 1992; Kwon et al., 2002). We show here that, when DC resistance to infection is circumvented (Mangeot et al., 2002; Goujon et al., 2006), HIV-1 induces DC maturation, an antiviral type I interferon response and activation of T cells. This innate response is dependent on the interaction of newly-synthesized HIV-1 capsid (CA) with cellular cyclophilin A (CypA) and the subsequent activation of the transcription factor IRF3. Because the peptidyl-prolyl isomerase CypA also interacts with CA to promote HIV-1 infectivity, our results suggest that CA conformation has evolved under opposing selective pressures for infectivity versus furtiveness. Thus, a cell intrinsic sensor for HIV-1 exists in DC and mediates an antiviral immune response, but it is not typically engaged due to absence of DC infection. The virulence of HIV-1 may be related to evasion of this response, whose manipulation may be necessary to generate an effective HIV-1 vaccine.

Pathogens induce an innate response through pattern-recognition receptors (Steinman et al., 2006). This shapes the subsequent adaptive immune response appropriately. While the innate response to several viruses is known (Takeuchi et al., 2009), the response to HIV-1 has remained elusive. Herein, we describe a method for inducing the innate response to HIV-1. This method leads to the up-regulation of activation markers, including co-stimulatory molecules for effective activation of T cells, and to the secretion of type-I interferon by dendritic cells. This approach can potentially be implemented in vaccine strategies.

Current HIV-1 vaccines strategies have failed at eliciting protective immunity. The reasons for such failures are not clear. Strikingly, these strategies have been based upon induction of T-cell and B-cell adaptive responses specific for HIV-1. However, these vaccines ignore the innate aspect of the immune response, and rely on classical adjuvant and/or on unrelated viral vectors to drive the initial innate response. This means that while B and T cells specific for HIV-1 are generated, these cells are not necessarily polarized or "shaped" to provide effector functions needed to clear HIV-1. This means, for instance that T and B cells might not secrete the appropriate cytokines, home to the appropriate peripheral tissues, or interact correctly with infected cells.

The purpose of the present invention and method is to induce the innate response to HIV-1 along with, or in the absence of, other adaptive responses. Triggering the innate response to HIV-1 should then shape adaptive immune responses so that T and B cells are polarized appropriately for HIV-1. This may overcome earlier failures to develop vaccines.

In accordance with the present invention there may be employed conventional molecular biology, microbiology, and recombinant DNA techniques within the skill of the art. Such techniques are explained fully in the literature. See, e.g., Sambrook et al, "Molecular Cloning: A Laboratory Manual" (1989); "Current Protocols in Molecular Biology" Volumes I-III [Ausubel, R. M., ed. (1994)]; "Cell Biology: A Laboratory Handbook" Volumes I-III [J. E. Celis, ed. (1994))]; "Current Protocols in Immunology" Volumes I-III [Coligan, J. E., ed. (1994)]; "Oligonucleotide Synthesis" (M. J. Gait ed. 1984); "Nucleic Acid Hybridization" [B. D. Hames & S. J. Higgins eds. (1985)]; "Transcription And Translation" [B. D. Hames & S. J. Higgins, eds. (1984)]; "Animal Cell Culture" [R. I. Freshney, ed. (1986)]; "Immobilized Cells And Enzymes" [IRL Press, (1986)]; B. Perbal, "A Practical Guide To Molecular Cloning" (1984).

Therefore, if appearing herein, the following terms shall have the definitions set out below.

A. TERMINOLOGY

The term "specific binding member" describes a member of a pair of molecules which have binding specificity for one another. The members of a specific binding pair may be naturally derived or wholly or partially synthetically produced. One member of the pair of molecules has an area on its surface, or a cavity, which specifically binds to and is therefore complementary to a particular spatial and polar organisation of the other member of the pair of molecules. Thus the members of the pair have the property of binding specifically to each other. Examples of types of specific binding pairs are antigen-antibody, biotin-avidin, hormone-hormone receptor, receptor-ligand, enzyme-substrate. This application is concerned with antigen-antibody type reactions.

The term "antibody" describes an immunoglobulin whether natural or partly or wholly synthetically produced. The term also covers any polypeptide or protein having a binding domain which is, or is homologous to, an antibody binding domain. CDR grafted antibodies are also contemplated by this term. An "antibody" is any immunoglobulin, including antibodies and fragments thereof, that binds a specific epitope. The term encompasses polyclonal, monoclonal, and chimeric antibodies, the last mentioned described in further detail in U.S. Pat. Nos. 4,816,397 and 4,816,567. The term "antibody(ies)" includes a wild type immunoglobulin (Ig) molecule, generally comprising four full length polypeptide chains, two heavy (H) chains and two light (L) chains, or an equivalent Ig homologue thereof (e.g., a camelid nanobody, which comprises only a heavy chain); including full length functional mutants, variants, or derivatives thereof, which retain the essential epitope binding features of an Ig molecule, and including dual specific, bispecific, multispecific, and dual variable domain antibodies; Immunoglobulin molecules can be of any class (e.g., IgG, IgE, IgM, IgD, IgA, and IgY), or subclass (e.g., IgG1, IgG2, IgG3, IgG4, IgA1, and IgA2). Also included within the meaning of the term "antibody" is any "antibody fragment".

An "antibody fragment" means a molecule comprising at least one polypeptide chain that is not full length, including (i) a Fab fragment, which is a monovalent fragment consisting of the variable light (VL), variable heavy (VH), constant light (CL) and constant heavy 1 (CH1) domains; (ii) a F(ab')2 fragment, which is a bivalent fragment comprising two Fab fragments linked by a disulfide bridge at the hinge region; (iii)

a heavy chain portion of an Fab (Fd) fragment, which consists of the VH and CH1 domains; (iv) a variable fragment (Fv) fragment, which consists of the VL and VH domains of a single arm of an antibody, (v) a domain antibody (dAb) fragment, which comprises a single variable domain (Ward, E. S. et al., Nature 341, 544-546 (1989)); (vi) a camelid antibody; (vii) an isolated complementarity determining region (CDR); (viii) a Single Chain Fv Fragment wherein a VH domain and a VL domain are linked by a peptide linker which allows the two domains to associate to form an antigen binding site (Bird et al, Science, 242, 423-426, 1988; Huston et al, PNAS USA, 85, 5879-5883, 1988); (ix) a diabody, which is a bivalent, bispecific antibody in which VH and VL domains are expressed on a single polypeptide chain, but using a linker that is too short to allow for pairing between the two domains on the same chain, thereby forcing the domains to pair with the complementarity domains of another chain and creating two antigen binding sites (WO94/13804; P. Holliger et al Proc. Natl. Acad. Sci. USA 90 6444-6448, (1993)); and (x) a linear antibody, which comprises a pair of tandem Fv segments (VH-CH1-VH-CH1) which, together with complementarity light chain polypeptides, form a pair of antigen binding regions; (xi) multivalent antibody fragments (scFv dimers, trimers and/or tetramers (Power and Hudson, J. Immunol. Methods 242: 193-204 9 (2000)); and (xii) other non-full length portions of heavy and/or light chains, or mutants, variants, or derivatives thereof, alone or in any combination.

As antibodies can be modified in a number of ways, the term "antibody" should be construed as covering any specific binding member or substance having a binding domain with the required specificity. Thus, this term covers antibody fragments, derivatives, functional equivalents and homologues of antibodies, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP-A-0120694 and EP-A-0125023 and U.S. Pat. Nos. 4,816,397 and 4,816,567.

An "antibody combining site" is that structural portion of an antibody molecule comprised of light chain or heavy and light chain variable and hypervariable regions that specifically binds antigen.

The phrase "antibody molecule" in its various grammatical forms as used herein contemplates both an intact immunoglobulin molecule and an immunologically active portion of an immunoglobulin molecule.

Exemplary antibody molecules are intact immunoglobulin molecules, substantially intact immunoglobulin molecules and those portions of an immunoglobulin molecule that contains the paratope, including those portions known in the art as Fab, Fab', F(ab')$_2$ and F(v), which portions are preferred for use in the therapeutic methods described herein.

Antibodies may also be bispecific, wherein one binding domain of the antibody is a specific binding member of the invention, and the other binding domain has a different specificity, e.g. to recruit an effector function or the like. Bispecific antibodies of the present invention include wherein one binding domain of the antibody is a specific binding member of the present invention, including a fragment thereof, and the other binding domain is a distinct antibody or fragment thereof, including that of a distinct anti-cancer or anti-tumor specific antibody. The other binding domain may be an antibody that recognizes or targets a particular cell type, as in a neural or glial cell-specific antibody. In the bispecific antibodies of the present invention the one binding domain of the antibody of the invention may be combined with other binding domains or molecules which recognize particular cell receptors and/or modulate cells in a particular fashion, as for instance an immune modulator (e.g., interleukin(s)), a growth modulator or cytokine (e.g. tumor necrosis factor (TNF), and particularly, the TNF bispecific modality demonstrated in U.S. Ser. No. 60/355,838 filed Feb. 13, 2002 incorporated herein in its entirety) or a toxin (e.g., ricin) or anti-mitotic or apoptotic agent or factor.

The phrase "monoclonal antibody" in its various grammatical forms refers to an antibody having only one species of antibody combining site capable of immunoreacting with a particular antigen. A monoclonal antibody thus typically displays a single binding affinity for any antigen with which it immunoreacts. A monoclonal antibody may also contain an antibody molecule having a plurality of antibody combining sites, each immunospecific for a different antigen; e.g., a bispecific (chimeric) monoclonal antibody.

The term "antigen binding domain" describes the part of an antibody which comprises the area which specifically binds to and is complementary to part or all of an antigen. Where an antigen is large, an antibody may bind to a particular part of the antigen only, which part is termed an epitope. An antigen binding domain may be provided by one or more antibody variable domains. Preferably, an antigen binding domain comprises an antibody light chain variable region (VL) and an antibody heavy chain variable region (VH).

The term "specific" may be used to refer to the situation in which one member of a specific binding pair will not show any significant binding to molecules other than its specific binding partner(s). The term is also applicable where e.g. an antigen binding domain is specific for a particular epitope which is carried by a number of antigens, in which case the specific binding member carrying the antigen binding domain will be able to bind to the various antigens carrying the epitope.

The term "adjuvant" refers to a compound or mixture that enhances the immune response, particularly to an antigen. An adjuvant can serve as a tissue depot that slowly releases the antigen and also as a lymphoid system activator that nonspecifically enhances the immune response (Hood et al., *Immunology, Second Ed.,* 1984, Benjamin/Cummings: Menlo Park, Calif., p. 384). Often, a primary challenge with an antigen alone, in the absence of an adjuvant, will fail to elicit a humoral or cellular immune response. Previously known and utilized adjuvants include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebacterium parvum*. Mineral salt adjuvants include but are not limited to: aluminum hydroxide, aluminum phosphate, calcium phosphate, zinc hydroxide and calcium hydroxide. Preferably, the adjuvant composition further comprises a lipid of fat emulsion comprising about 10% (by weight) vegetable oil and about 1-2% (by weight) phospholipids. Preferably, the adjuvant composition further optionally comprises an emulsion form having oily particles dispersed in a continuous aqueous phase, having an emulsion forming polyol in an amount of from about 0.2% (by weight) to about 49% (by weight), optionally a metabolizable oil in an emulsion-forming amount of up to 15% (by weight), and optionally a glycol ether-based surfactant in an emulsion-stabilizing amount of up to about 5% (by weight).

As used herein, the term "immunomodulator" refers to an agent which is able to modulate an immune response. An example of such modulation is an enhancement of cell activation or of antibody production.

The term "effective amount" of an immunomodulator refers to an amount of an immunomodulator sufficient to enhance a vaccine-induced immune response, be it cell-mediated, humoral or antibody-mediated. An effective amount of an immunomodulator, if injected, can be in the range of about 0.1-1,000 µg, preferably 1-900 µg, more preferably 5-500 µg, for a human subject, or in the range of about 0.01-10.0 µg/Kg body weight of the subject animal. This amount may vary to some degree depending on the mode of administration, but will be in the same general range. If more than one immunomodulator is used, each one may be present in these amounts or the total amount may fall within this range. An effective amount of an antigen may be an amount capable of eliciting a demonstrable immune response in the absence of an immunomodulator. For many antigens, this is in the range of about 5-100 µg for a human subject. The appropriate amount of antigen to be used is dependent on the specific antigen and is well known in the art.

The exact effective amount necessary will vary from subject to subject, depending on the species, age and general condition of the subject, the severity of the condition being treated, the mode of administration, etc. Thus, it is not possible to specify an exact effective amount. However, the appropriate effective amount may be determined by one of ordinary skill in the art using only routine experimentation or prior knowledge in the vaccine art.

An "immunological response" to a composition or vaccine comprised of an antigen is the development in the host of a cellular- and/or antibody-mediated immune response to the composition or vaccine of interest. Usually, such a response consists of the subject producing antibodies, B cells, helper T cells, suppressor T cells, and/or cytotoxic T cells directed specifically to an antigen or antigens included in the composition or vaccine of interest.

The term "comprise" generally used in the sense of include, that is to say permitting the presence of one or more features or components.

The term "consisting essentially of" refers to a product, particularly a peptide sequence, of a defined number of residues which is not covalently attached to a larger product. In the case of the peptide of the invention referred to above, those of skill in the art will appreciate that minor modifications to the N- or C-terminal of the peptide may however be contemplated, such as the chemical modification of the terminal to add a protecting group or the like, e.g. the amidation of the C-terminus.

The term "isolated" refers to the state in which specific binding members of the invention, or nucleic acid encoding such binding members will be, in accordance with the present invention. Members and nucleic acid will be free or substantially free of material with which they are naturally associated such as other polypeptides or nucleic acids with which they are found in their natural environment, or the environment in which they are prepared (e.g. cell culture) when such preparation is by recombinant DNA technology practised in vitro or in vivo. Members and nucleic acid may be formulated with diluents or adjuvants and still for practical purposes be isolated—for example the members will normally be mixed with gelatin or other carriers if used to coat microtitre plates for use in immunoassays, or will be mixed with pharmaceutically acceptable carriers or diluents when used in diagnosis or therapy.

As used herein, "pg" means picogram, "ng" means nanogram, "ug" or "µg" mean microgram, "mg" means milligram, "ul" or "µl" mean microliter, "ml" means milliliter, "l" means liter.

The amino acid residues described herein are preferred to be in the "L" isomeric form. However, residues in the "D" isomeric form can be substituted for any L-amino acid residue, as long as the desired functional property of immunoglobulin-binding is retained by the polypeptide. $NH_2$ refers to the free amino group present at the amino terminus of a polypeptide. COOH refers to the free carboxy group present at the carboxy terminus of a polypeptide. In keeping with standard polypeptide nomenclature, *J. Biol. Chem.*, 243:3552-59 (1969), abbreviations for amino acid residues are shown in the following Table of Correspondence:

| TABLE OF CORRESPONDENCE | | |
|---|---|---|
| SYMBOL | | |
| 1-Letter | 3-Letter | AMINO ACID |
| Y | Tyr | tyrosine |
| G | Gly | glycine |
| F | Phe | phenylalanine |
| M | Met | methionine |
| A | Ala | alanine |
| S | Ser | serine |
| I | Ile | isoleucine |
| L | Leu | leucine |
| T | Thr | threonine |
| V | Val | valine |
| P | Pro | proline |
| K | Lys | lysine |
| H | His | histidine |
| Q | Gln | glutamine |
| E | Glu | glutamic acid |
| W | Trp | tryptophan |
| R | Arg | arginine |
| D | Asp | aspartic acid |
| N | Asn | asparagine |
| C | Cys | cysteine |

It should be noted that all amino-acid residue sequences are represented herein by formulae whose left and right orientation is in the conventional direction of amino-terminus to carboxy-terminus. Furthermore, it should be noted that a dash at the beginning or end of an amino acid residue sequence indicates a peptide bond to a further sequence of one or more amino-acid residues. The above Table is presented to correlate the three-letter and one-letter notations which may appear alternately herein.

A "replicon" is any genetic element (e.g., plasmid, chromosome, virus) that functions as an autonomous unit of DNA replication in vivo; i.e., capable of replication under its own control.

A "vector" is a replicon, such as plasmid, phage or cosmid, to which another DNA segment may be attached so as to bring about the replication of the attached segment.

A "DNA molecule" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA).

An "origin of replication" refers to those DNA sequences that participate in DNA synthesis.

A DNA "coding sequence" is a double-stranded DNA sequence which is transcribed and translated into a polypeptide in vivo when placed under the control of appropriate regulatory sequences. The boundaries of the coding sequence are determined by a start codon at the 5' (amino) terminus and a translation stop codon at the 3' (carboxyl) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A polyadenylation signal and transcription termination sequence will usually be located 3' to the coding sequence.

Transcriptional and translational control sequences are DNA regulatory sequences, such as promoters, enhancers, polyadenylation signals, terminators, and the like, that provide for the expression of a coding sequence in a host cell.

A "promoter sequence" is a DNA regulatory region capable of binding RNA polymerase in a cell and initiating transcription of a downstream (3' direction) coding sequence. For purposes of defining the present invention, the promoter sequence is bounded at its 3' terminus by the transcription initiation site and extends upstream (5' direction) to include the minimum number of bases or elements necessary to initiate transcription at levels detectable above background. Within the promoter sequence will be found a transcription initiation site (conveniently defined by mapping with nuclease S1), as well as protein binding domains (consensus sequences) responsible for the binding of RNA polymerase. Eukaryotic promoters will often, but not always, contain "TATA" boxes and "CAT" boxes. Prokaryotic promoters contain Shine-Dalgarno sequences in addition to the –10 and –35 consensus sequences.

An "expression control sequence" is a DNA sequence that controls and regulates the transcription and translation of another DNA sequence. A coding sequence is "under the control" of transcriptional and translational control sequences in a cell when RNA polymerase transcribes the coding sequence into mRNA, which is then translated into the protein encoded by the coding sequence.

A "signal sequence" can be included before the coding sequence. This sequence encodes a signal peptide, N-terminal to the polypeptide, that communicates to the host cell to direct the polypeptide to the cell surface or secrete the polypeptide into the media, and this signal peptide is clipped off by the host cell before the protein leaves the cell. Signal sequences can be found associated with a variety of proteins native to prokaryotes and eukaryotes.

The term "oligonucleotide," as used herein in referring to the probe of the present invention, is defined as a molecule comprised of two or more ribonucleotides, preferably more than three. Its exact size will depend upon many factors which, in turn, depend upon the ultimate function and use of the oligonucleotide.

The term "primer" as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and use of the method. For example, for diagnostic applications, depending on the complexity of the target sequence, the oligonucleotide primer typically contains 15-25 or more nucleotides, although it may contain fewer nucleotides.

The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

As used herein, the terms "restriction endonucleases" and "restriction enzymes" refer to bacterial enzymes, each of which cut double-stranded DNA at or near a specific nucleotide sequence.

A cell has been "transformed" by exogenous or heterologous DNA when such DNA has been introduced inside the cell. The transforming DNA may or may not be integrated (covalently linked) into chromosomal DNA making up the genome of the cell. In prokaryotes, yeast, and mammalian cells for example, the transforming DNA may be maintained on an episomal element such as a plasmid. With respect to eukaryotic cells, a stably transformed cell is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

Two DNA sequences are "substantially homologous" when at least about 75% (preferably at least about 80%, and most preferably at least about 90 or 95%) of the nucleotides match over the defined length of the DNA sequences. Sequences that are substantially homologous can be identified by comparing the sequences using standard software available in sequence data banks, or in a Southern hybridization experiment under, for example, stringent conditions as defined for that particular system. Defining appropriate hybridization conditions is within the skill of the art. See, e.g., Maniatis et al., supra; DNA Cloning, Vols. I & II, supra; Nucleic Acid Hybridization, supra.

It should be appreciated that also within the scope of the present invention are DNA sequences encoding or protein or peptide sequences of the Gag proteins, peptides or immune activator proteins or peptides of the invention which code for e.g. a Gag or capsid having the same amino acid sequence as provided herein, or comprising sequences which are degenerate thereto. DNA sequences having the nucleic acid sequence encoding the peptides of the invention are contemplated, including degenerate sequences thereof encoding the same, or a conserved or substantially similar, amino acid sequence. By "degenerate to" is meant that a different three-letter codon is used to specify a particular amino acid. It is well known in the art that the following codons can be used interchangeably to code for each specific amino acid:

```
Phenylalanine (Phe or F)
UUU or UUC

Leucine (Leu or L)
UUA or UUG or CUU or CUC or CUA or CUG

Isoleucine (Ile or I)
AUU or AUC or AUA

Methionine (Met or M)
AUG

Valine (Val or V)
GUU or GUC of GUA or GUG

Serine (Ser or S)
UCU or UCC or UCA or UCG or AGU or AGC

Proline (Pro or P)
CCU or CCC or CCA or CCG

Threonine (Thr or T)
ACU or ACC or ACA or ACG

Alanine (Ala or A)
GCU or GCG or GCA or GCG

Tyrosine (Tyr or Y)
UAU or UAC

Histidine (His or H)
CAU or CAC

Glutamine (Gln or Q)
CAA or CAG

Asparagine (Asn or N)
AAU or AAC

Lysine (Lys or K)
AAA or AAG

Aspartic Acid (Asp or D)
GAU or GAC

Glutamic Acid (Glu or E)
GAA or GAG

Cysteine (Cys or C)
UGU or UGC

Arginine (Arg or R)
CGU or CGC or CGA or CGG or AGA or AGG

Glycine (Gly or G)
GGU or GGC or GGA or GGG

Tryptophan (Trp or W)
UGG

Termination codon
UAA (ochre) or UAG (amber) or UGA (opal)
```

It should be understood that the codons specified above are for RNA sequences. The corresponding codons for DNA have a T substituted for U.

Mutations can be made in the sequences encoding the protein or peptide sequences of the Gag proteins, peptides or immune activator proteins or peptides of the invention, such that a particular codon is changed to a codon which codes for a different amino acid. Such a mutation is generally made by making the fewest nucleotide changes possible. A substitution mutation of this sort can be made to change an amino acid in the resulting protein in a non-conservative manner (i.e., by changing the codon from an amino acid belonging to a grouping of amino acids having a particular size or characteristic to an amino acid belonging to another grouping) or in a conservative manner (i.e., by changing the codon from an amino acid belonging to a grouping of amino acids having a particular size or characteristic to an amino acid belonging to the same grouping). Such a conservative change generally leads to less change in the structure and function of the resulting protein. A non-conservative change is more likely to alter the structure, activity or function of the resulting protein. The present invention should be considered to include sequences containing conservative changes which do not significantly alter the activity or binding characteristics of the resulting protein. Further, variants and subtypes of HIV are known and recognized and any such variants or subtype corresponding protein or peptide sequences of the Gag proteins, peptides or immune activator proteins or peptides of the invention are encompassed and contemplated herein.

The following is one example of various groupings of amino acids:

Amino acids with nonpolar R groups
Alanine, Valine, Leucine, Isoleucine, Proline, Phenylalanine, Tryptophan, Methionine
Amino acids with uncharged polar R groups
Glycine, Serine, Threonine, Cysteine, Tyrosine, Asparagine, Glutamine
Amino acids with charged polar R groups (negatively charged at Ph 6.0) Aspartic acid, Glutamic acid
Basic amino acids (positively charged at pH 6.0)
Lysine, Arginine, Histidine (at pH 6.0)

Another grouping may be those amino acids with phenyl groups: Phenylalanine, Tryptophan, Tyrosine Another grouping may be according to molecular weight (i.e., size of R groups):

| | | | |
|---|---|---|---|
| Glycine | 75 | Alanine | 89 |
| Serine | 105 | Proline | 115 |
| Valine | 117 | Threonine | 119 |
| Cysteine | 121 | Leucine | 131 |
| Isoleucine | 131 | Asparagine | 132 |
| Aspartic acid | 133 | Glutamine | 146 |
| Lysine | 146 | Glutamic acid | 147 |
| Methionine | 149 | Histidine (at pH 6.0) | 155 |
| Phenylalanine | 165 | Arginine | 174 |
| Tyrosine | 181 | Tryptophan | 204 |

Particularly preferred substitutions are:

Lys for Arg and vice versa such that a positive charge may be maintained;

Glu for Asp and vice versa such that a negative charge may be maintained;

Ser for Thr such that a free —OH can be maintained; and

Gln for Asn such that a free $NH_2$ can be maintained.

Exemplary and preferred conservative amino acid substitutions include any of: glutamine (Q) for glutamic acid (E) and vice versa; leucine (L) for valine (V) and vice versa; serine (S) for threonine (T) and vice versa; isoleucine (I) for valine (V) and vice versa; lysine (K) for glutamine (Q) and vice versa; isoleucine (I) for methionine (M) and vice versa; serine (S) for asparagine (N) and vice versa; leucine (L) for methionine (M) and vice versa; lysine (L) for glutamic acid (E) and vice versa; alanine (A) for serine (S) and vice versa; tyrosine (Y) for phenylalanine (F) and vice versa; glutamic acid (E) for aspartic acid (D) and vice versa; leucine (L) for isoleucine (I) and vice versa; lysine (K) for arginine (R) and vice versa.

Amino acid substitutions may also be introduced to substitute an amino acid with a particularly preferable property. For example, a Cys may be introduced a potential site for disulfide bridges with another Cys. A H is may be introduced as a particularly "catalytic" site (i.e., H is can act as an acid or base and is the most common amino acid in biochemical catalysis). Pro may be introduced because of its particularly planar structure, which induces β-turns in the protein's structure.

Two amino acid sequences are "substantially homologous" when at least about 70% of the amino acid residues (preferably at least about 80%, and most preferably at least about 90 or 95%) are identical, or represent conservative substitutions.

A "heterologous" region of the DNA construct is an identifiable segment of DNA within a larger DNA molecule that is not found in association with the larger molecule in nature. Thus, when the heterologous region encodes a mammalian gene, the gene will usually be flanked by DNA that does not flank the mammalian genomic DNA in the genome of the source organism. Another example of a heterologous coding sequence is a construct where the coding sequence itself is not found in nature (e.g., a cDNA where the genomic coding sequence contains introns, or synthetic sequences having codons different than the native gene). Allelic variations or naturally-occurring mutational events do not give rise to a heterologous region of DNA as defined herein.

A DNA sequence is "operatively linked" to an expression control sequence when the expression control sequence controls and regulates the transcription and translation of that DNA sequence. The term "operatively linked" includes having an appropriate start signal (e.g., ATG) in front of the DNA sequence to be expressed and maintaining the correct reading frame to permit expression of the DNA sequence under the control of the expression control sequence and production of the desired product encoded by the DNA sequence. If a gene that one desires to insert into a recombinant DNA molecule does not contain an appropriate start signal, such a start signal can be inserted in front of the gene.

The term "standard hybridization conditions" refers to salt and temperature conditions substantially equivalent to 5×SSC and 65° C. for both hybridization and wash. However, one skilled in the art will appreciate that such "standard hybridization conditions" are dependent on particular conditions including the concentration of sodium and magnesium in the buffer, nucleotide sequence length and concentration, percent mismatch, percent formamide, and the like. Also important in the determination of "standard hybridization conditions" is whether the two sequences hybridizing are RNA-RNA, DNA-DNA or RNA-DNA. Such standard hybridization conditions are easily determined by one skilled in the art according to well known formulae, wherein hybridization is typically 10-20° C. below the predicted or determined $T_m$ with washes of higher stringency, if desired.

The term 'agent' means any molecule, including polypeptides, antibodies, polynucleotides, chemical compounds and small molecules. In particular the term agent includes compounds such as test compounds or drug candidate compounds.

The term 'agonist' refers to a ligand that stimulates the receptor the ligand binds to in the broadest sense or stimulates a response that would be elicited on binding of a natural binder to a binding site.

The term 'assay' means any process used to measure a specific property of a compound or agent. A 'screening assay' means a process used to characterize or select compounds based upon their activity from a collection of compounds.

The term 'preventing' or 'prevention' refers to a reduction in risk of acquiring or developing a disease or disorder (i.e., causing at least one of the clinical symptoms of the disease not to develop) in a subject that may be exposed to a disease-causing agent, or predisposed to the disease in advance of disease onset.

The term 'prophylaxis' is related to and encompassed in the term 'prevention', and refers to a measure or procedure the purpose of which is to prevent, rather than to treat or cure a disease. Non-limiting examples of prophylactic measures may include the administration of vaccines; the administration of low molecular weight heparin to hospital patients at risk for thrombosis due, for example, to immobilization; and the administration of an anti-malarial agent such as chloroquine, in advance of a visit to a geographical region where malaria is endemic or the risk of contracting malaria is high.

'Therapeutically effective amount' means that amount of a drug, compound, antimicrobial, antibody, or pharmaceutical agent that will elicit the biological or medical response of a subject that is being sought by a medical doctor or other clinician. As an example, with regard to immune response, the term "effective amount" is intended to include an effective amount of a compound or agent that will bring about a biologically meaningful decrease in the amount of or extent of immune response, activation indicator and/or a biologically meaningful increase in the amount or extent of dendritic cell, T cell and/or B cell effects. The phrase "therapeutically effective amount" is used herein to mean an amount sufficient to prevent, and preferably reduce by at least about 30 percent, more preferably by at least 50 percent, most preferably by at least 90 percent, a clinically significant change in the immune response or immune cell indicator or response, or in a patient's response to an antigen, vaccine, or other immune agent, or in a patient's clearance of an infectious agent, or other feature of pathology such as for example, elevated activated T or B cells, activated DC cell count, fever or white cell count.

The term 'treating' or 'treatment' of any disease or infection refers, in one embodiment, to ameliorating the disease or infection (i.e., arresting the disease or growth of the infectious agent or bacteria or reducing the manifestation, extent or severity of at least one of the clinical symptoms thereof). In another embodiment 'treating' or 'treatment' refers to ameliorating at least one physical parameter, which may not be discernible by the subject. In yet another embodiment, 'treating' or 'treatment' refers to modulating the disease or infection, either physically, (e.g., stabilization of a discernible symptom), physiologically, (e.g., stabilization of a physical parameter), or both. In a further embodiment, 'treating' or 'treatment' relates to slowing the progression of a disease or reducing an infection.

The phrase "pharmaceutically acceptable" refers to molecular entities and compositions that are physiologically tolerable and do not typically produce an allergic or similar untoward reaction, such as gastric upset, dizziness and the like, when administered to a human.

As used herein, "pg" means picogram, "ng" means nanogram, "ug" or "µg" mean microgram, "mg" means milligram, "ul" or "µl" mean microliter, "ml" means milliliter, "l" means liter.

As used herein, the term "replication defective HIV vector" refers to a vector that encodes HIV peptides/proteins, but does not encode live virus.

B. DETAILED DISCLOSURE

The invention relates generally to methods and agents for inducing and evaluating the innate immune response to HIV-1. Current HIV-1 vaccines strategies have failed at eliciting protective immunity and ignore the innate aspect of the immune response, relying on classical adjuvant and/or on unrelated viral vectors to drive the initial innate response. The present invention now provides indicators of innate immune response to HIV, methods for stimulating or facilitating immune response to HIV, and assays for screening and identifying agents, compounds or peptides to modulate immune response to HIV. The method of the invention leads to and the assays of the invention are based on the up-regulation of activation markers, including co-stimulatory molecules for effective activation of T cells, and to the secretion of type-I interferon by dendritic cells. The methods, agents and assays of the invention can be implemented in vaccine strategies and the stimulation of immune response to HIV.

Thus, a purpose of the present invention and method is to induce the innate response to HIV-1 along with, or in the absence of, other adaptive responses. Triggering the innate response to HIV-1 should then shape adaptive immune responses so that T and B cells are polarized appropriately for HIV-1. This invention thus provides a means to overcome earlier failures to develop vaccines.

The present invention demonstrates that Cyclophilin A binding plays a critical role in the activation of DCs (monocyte-derived dendritic cells) on HIV infection. Cyclosporin A treatment prevents activation. Cyclophilin A binds HIV GAG protein, particularly p24 capsid protein, particularly via a cyclophilin binding peptide corresponding to position 213 to 237 of Gag polyprotein. In a particular embodiment a cyclophilin binding peptide comprises or consists of the sequence of DRLHPVHAGPIAPGQMREPRGSDIA (SEQ ID NO: 15) or DRVHPVHAGPIAPGQMREPRGSDIA (SEQ ID NO: 16). The invention demonstrates that mutant Gag proteins which disrupt Cyclophilin binding do not induce activation. Other mutant Gag proteins are herein identified that enhance activation. Therefore, in an aspect of the invention, Gag proteins or peptides which facilitate or promote activation may be utilized in modulating and enhancing activation and immune response to HIV antigens of HIV infection. Gag or capsid protein, polypeptide or cyclophilin binding regions or peptides thereof may be utilized to enhance innate immunity. The Gag proteins or peptides of the invention may be provided as naked DNA, in any of various vectors, as monomers, multimers, dendrimers, or peptide fusions. One or more Gag proteins or peptides from HIV subtypes, variants, or mutants may be combined to enhance immune response. The peptides may be combined with, associated with, covalently attached to or fused to other immune modulators, including interferons, interleukins, T or B cell antigens or stimulators, other activators, or adjuvant molecules.

The invention provides proteins and peptides, particularly HIV gag peptides or proteins which have application and use, alone or in combination with other immune system modulators, T cell modulators, antibodies, vaccines, antigens, or chemotherapeutics for stimulating, facilitating or enhancing desired innate immune system or immune cell actions or activities, particularly to HIV, including antigen response, vaccine response, anti-HIV response.

In a further embodiment, the present invention relates to certain therapeutic methods which would be based upon the activity of the cyclophilin binding or immune activator peptides, or upon agents or other drugs determined to possess the same activity. A therapeutic method is associated with the modulation of the immune response, particularly stimulation or enhancement of innate immunity and response to viral antigens and/or infection, particularly of HIV. A further therapeutic method is associated with methods for stimulating immune response to HIV comprising administering the cyclophilin binding or immune activator peptides, or agents or other drugs determined to possess the same activity, alone or in combination with HIV antigens or immunogens, or other immune modulators, including adjuvants, for generating an immunogenic and/or protective response to HIV. In one aspect of this method, the cyclophilin binding or immune activator peptides, or agents or other drugs determined to possess the same activity, are administered to individuals exposed to or at risk of exposure to HIV. In a further aspect, the cyclophilin binding or immune activator peptides, or agents or other drugs determined to possess the same activity are administered to an HIV-infected individual to stimulate immune response and clearance of the virus.

The present invention also includes the cyclophilin binding or immune activator peptides, or agents or other drugs determined to possess the same activity, which are covalently attached to or otherwise associated with other molecules or agents. These other molecules or agents include, but are not limited to, molecules (including antibodies or antibody fragments) with distinct recognition, targeting or binding characteristics, immune cell modulators, immune cell antigens, toxins, ligands, adjuvants, and chemotherapeutic agents.

Peptides, proteins of the invention may be labelled with a detectable or functional label. Detectable labels include, but are not limited to, radiolabels such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{121}I$, $^{124}I$, $^{125}I$, $^{131}I$, $^{111}In$, $^{117}Lu$, $^{211}At$, $^{198}Au$, $^{67}Cu$, $^{225}Ac$, $^{213}Bi$, $^{99}Tc$ and $^{186}Re$, which may be attached to antibodies of the invention using conventional chemistry known in the art of antibody imaging. Labels also include fluorescent labels (for example fluorescein, rhodamine, Texas Red) and labels used conventionally in the art for MRI-CT imaging. They also include enzyme labels such as horseradish peroxidase, β-glucoronidase, β-galactosidase, urease. Labels further include chemical moieties such as biotin which may be detected via binding to a specific cognate detectable moiety, e.g. labelled avidin. Functional labels include substances which are designed to be targeted to the site of a tumor to cause destruction of tumor tissue. Such functional labels include cytotoxic drugs such as 5-fluorouracil or ricin and enzymes such as bacterial carboxypeptidase or nitroreductase, which are capable of converting prodrugs into active drugs at the site of a tumor.

Peptides of and of use in the present invention may include synthetic, recombinant or peptidomimetic entities. The peptides may be monomers, polymers, multimers, dendrimers, concatamers of various forms known or contemplated in the art, and may be so modified or multimerized so as to improve activity, specificity or stability. For instance, and not by way of limitation, several strategies have been pursued in efforts to increase the effectiveness of antimicrobial peptides including dendrimers and altered amino acids (Tam, J. P. et al (2002) Eur J Biochem 269 (3): 923-932; Janiszewska, J. et al (2003) Bioorg Med Chem Lett 13 (21):3711-3713; Ghadiri et al. (2004) Nature 369(6478):301-304; DeGrado et al (2003) Protein Science 12(4):647-665; Tew et al. (2002) PNAS 99(8): 5110-5114; Janiszewska, J et al (2003) Bioorg Med Chem Lett 13 (21): 3711-3713). U.S. Pat. No. 5,229,490 to Tam discloses a particular polymeric construction formed by the binding of multiple antigens to a dendritic core or backbone.

Protamines or polycationic amino acid peptides containing combinations of one or more recurring units of cationic amino acids, such as arginine (R), tryptophan (W), lysine (K), even synthetic polyarginine, polytryptophan, polylysine, have been shown to be capable of killing microbial cells. These peptides cross the plasma membrane to facilitate uptake of various biopolymers or small molecules (Mitchell D J et al (2002) J Peptide Res 56(5):318-325).

Conjugates or fusion proteins of the present invention, wherein the immune activator proteins, Gag, capsid proteins or peptides, particularly cyclophilin binding fragments thereof, of the present invention are conjugated or attached to other molecules or agents further include, but are not limited to binding members conjugated to a cell targeting agent or sequence, chemical ablation agent, toxin, immunomodulator, cytokine, cytotoxic agent, chemotherapeutic agent or drug.

Uptake and targeting of DCs can be achieved using variety techniques known in the art, including coupling to antibodies targeting DC-specific surface molecules (Romani et al., 2010; the entire contents of which is incorporated herein in its entirety, including references cited therein); utilization of engineered Sindbis envelope that specifically target DC instead of VSV-G (Yang et al., 2008; the entire contents of which is incorporated herein in its entirety); site of administration; blood infusion; or ex vivo culture of DC, treatment if ex vivo cultured DC to introduce the desired construct/s, and re-injection of same into subject in need thereof.

In vitro assays are described herein which may be utilized by the skilled artisan to further or additionally screen, assess, and/or verify the immune activator proteins, Gag, capsid proteins or peptides, particularly cyclophilin binding fragments thereof, or agents of the present invention, including further assessing innate immune response, adaptive immunity, or protection against HIV. Cell based assays and in vitro methods are described herein below and were utilized to perform experiments as described, for example, in Example 3.

In vivo animal models of HIV or HIV-like viral infection or HIV immune response may be utilized by the skilled artisan to further or additionally screen, assess, and/or verify the immune activator proteins, Gag, capsid proteins or peptides, particularly cyclophilin binding fragments thereof, or agents of the present invention, including further assessing innate immune response, adaptive immunity, or protection against HIV in vivo. Such animal models include, but are not limited to models of immune system modulation or immune response. In particular, HIV models, including "humanized" mice models are known and can be utilized. Immunodeficient mice are engrafted with a human immune system using various sources of hematopoietic stem cells, depending on the model (CD34+ cells from fetal liver, from cord blood, etc). Humanized mice may be challenged with HIV after immunization, for example humanized bone marrow-liver-thymus (BLT) mice (Wege A K et al 92008) Curr Top Microbiol Immunol 324:149-165; Denton P W et al (2008) PLoS Jan 15; 5(1):e16). DKO-hu HSC mice may be used as a humanized mouse model susceptible to HIV infection (Zhang L et al (2007) Blood 109(7):2978-81). Also, hu-PBL-SCID mice have been immunized with IFN-DCs and pulsed with inactivated HIV or infected with HIV to assess response and protection (Lapenta C et al (2003) J Exp Med 198(2):361-7.

Proteins, peptides, immune activators or agents of the present invention may be administered to a patient in need of treatment via any suitable route, including by intravenous, intraperitoneal, intramuscular injection, or orally. The precise dose will depend upon a number of factors, including whether the proteins, peptides, immune activators or agents are for diagnosis or for treatment or for prevention. The dosage or dosing regime of an adult patient may be proportionally adjusted for children and infants, and also adjusted for other administration or other formats, in proportion for example to molecular weight or immune response. Administration or treatments may be repeated at appropriate intervals, at the discretion of the physician.

Proteins, peptides, immune activators or agents of the present invention will usually be administered in the form of a pharmaceutical composition, which may comprise at least one component in addition to the proteins, peptides, immune activators or agents. Thus pharmaceutical compositions according to the present invention, and for use in accordance with the present invention, may comprise, in addition to active ingredient, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. intravenous, or by deposition at a tumor site.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient may be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

A composition may be administered alone or in combination with other treatments, therapeutics or agents, either simultaneously or sequentially dependent upon the condition to be treated. In addition, the present invention contemplates and includes compositions comprising the proteins, peptides, immune activators or agents herein described and other agents or therapeutics such as immune modulators, antibodies, immune cell stimulators, or adjuvants. In addition, the composition may be administered with hormones such as dexamethasone, immune modulators, such as interleukins, tumor necrosis factor (TNF) or other growth factors, colony stimulating factors, or cytokines which stimulate the immune response and reduction or elimination of virus. The composition may also be administered with, or may include combinations along with immune cell antigen antibodies or immune cell modulators.

The preparation of therapeutic compositions which contain polypeptides, analogs or active fragments as active ingredients is well understood in the art. Typically, such compositions are prepared as injectables, either as liquid solutions or suspensions. However, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

A protein, peptide, immune activator or agent can be formulated into the therapeutic composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

Accordingly, also encompassed herein is a composition comprising a protein or peptide comprising the cyclophilin binding domain of HIV Gag protein or a first nucleic acid sequence encoding a protein or peptide comprising the cyclophilin binding domain of HIV Gag protein alone or in combination with at least one viral protein or peptide encoded by HIVGFP (SEQ ID NO: 1); HIVGFP viral particles or derivatives thereof; or a second nucleic acid sequence encoding the at least one viral protein or peptide of HIVGFP (SEQ ID NO: 1), and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising a protein or peptide comprising the cyclophilin binding domain of HIV Gag protein or a first nucleic acid sequence encoding a protein or peptide comprising the cyclophilin binding domain of HIV Gag protein alone or in combination with at least one viral protein or peptide encoded by HIVGFP (SEQ ID NO: 1); HIVGFP viral particles or derivatives thereof; or a second nucleic acid sequence encoding the at least one viral protein or peptide of HIVGFP (SEQ ID NO: 1), and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

Also encompassed herein is a composition comprising a Vpx-Vpr fusion protein, a Vpx protein, SIVVLP(G), or a vector comprising a nucleic acid sequence encoding the Vpx-Vpr fusion protein or the Vpx protein, and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising a Vpx-Vpr fusion protein, a Vpx protein, SIVVLP(G), or a vector comprising a nucleic acid sequence encoding the Vpx-Vpr fusion protein or the Vpx protein, and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

Also encompassed herein is a composition comprising an agent, compound or peptide capable of binding the cyclophilin binding domain of HIV Gag protein; or the agent, compound or peptide capable of binding the cyclophilin binding domain of HIV Gag protein in combination with the protein or peptide comprising the cyclophilin binding domain of HIV Gag protein, and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising an agent, compound or peptide capable of binding the cyclophilin binding domain of HIV Gag protein; or the agent, compound or peptide capable of binding the cyclophilin binding domain of HIV Gag protein in combination with the protein or peptide comprising the cyclophilin binding domain of HIV Gag protein, and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the MN-related disorder when administered to the patient.

Also encompassed herein is a composition comprising a replication defective HIV vector encoding at least one HIV-1 Gag polypeptide or one HIV-2 Gag polypeptide comprising a cyclophilin binding domain, wherein the replication defective vector is missing at least one gene or activity essential for HIV-1 or HIV-2 replication and/or budding, and a pharmaceutically acceptable buffer, for use in treating a patient with HIV, wherein said composition alleviates symptoms of HIV-1 infection in the patient with HIV when administered to the patient in a therapeutically effective amount. Such compositions also have utility for use in prophylaxis for a patient at risk for exposure to HIV-1 or suspected of being exposed to HIV-1 wherein said composition prevents or alleviates symptoms of a potential subsequent HIV-1 infection in the patient when administered to the patient in a therapeutically effective amount. Also encompassed herein is the use of a therapeutically effective amount of a composition comprising a replication defective HIV vector encoding at least one HIV-1 Gag polypeptide or one HIV-2 Gag polypeptide comprising a cyclophilin binding domain, wherein the replication defective vector is missing at least one gene or activity essential for HIV-1 or HIV-2 replication and/or budding, and a pharmaceutically acceptable buffer in the manufacture of a medicament for treating a patient with HIV or prophylaxis for a patient suspected of being exposed to HIV-1 or at risk for exposure to HIV-1, wherein the medicament alleviates or prevents symptoms of the HIV-related disorder when administered to the patient.

The peptide or agent containing compositions are conventionally administered intramuscularly, intravenously, as by injection of a unit dose, or orally, for example. The term "unit dose" when used in reference to a therapeutic composition of the present invention refers to physically discrete units suitable as unitary dosage for humans, each unit containing a predetermined quantity of active material calculated to produce the desired therapeutic effect in association with the required diluent; i.e., carrier, or vehicle.

The compositions are administered in a manner compatible with the dosage formulation, and in a therapeutically effective amount. The quantity to be administered depends on the subject to be treated, capacity of the subject's immune system to utilize the active ingredient, and degree of activation and immune response desired. Precise amounts of active ingredient required to be administered depend on the judgment of the practitioner and are peculiar to each individual. Suitable regimes for initial administration and follow on administration are also variable, and may include an initial administration followed by repeated doses at appropriate intervals by a subsequent injection or other administration.

Pharmaceutical compositions for oral administration may be in tablet, capsule, powder or liquid form. A tablet may comprise a solid carrier such as gelatin or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

For intravenous, injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The present invention includes assay methods and assay systems for screening and identifying modulators, including enhancers of innate immune response, particularly to HIV. Thus, in one aspect, cyclophilin binding domains, peptides, Gag or capsid may be utilized in assay to identify compounds, agents, peptides which bind or otherwise interact therewith. Alternatively or additionally, activation markers, such as but not limited to one or more of CD86, CD80, CD38, CD83 may be utilized as indicators for screening to identify or characterize compounds, agents, peptides which facilitate activation. In a further aspect interferon production, or induction of Type-I interferon response signature genes may be utilized in an assay to identify or characterize compounds, agents, peptides which facilitate activation and/or innate response to HIV infection.

The diagnostic utility of the present invention extends to the use of the activation markers, including CD86, CD80, CD38, CD83, interferon production, or induction of Type-I interferon response signature genes in assays to characterize immune response or immune system cell activation response to HIV. The expression or activity of the markers may be examined by known techniques, including FACs analysis, immunoassay, RTPCR, etc which may vary with the nature of the marker and are known to the artisan. This analysis may be conducted in cell systems, in vitro, or in animal model systems, in vivo, or in patient or clinical or vaccine trials or evaluation studies.

Diagnostic applications of the present invention, particularly protein, peptide, immune activator or agents thereof, include in vitro and in vivo applications well known and standard to the skilled artisan and based on the present description. Diagnostic assays and kits for in vitro assessment and evaluation of immune system status and/or immune response, HIV infection and/or response, HIV replication, may be utilized to diagnose, evaluate and monitor patient samples with regard to an anticipated or desired immune system response, antigen response, or vaccine response. The assessment and evaluation of immune system status and/or immune response is also useful in determining the suitability of a patient for a clinical trial of a drug or for the administration of a particular chemotherapeutic agent, including a protein, peptide, immune activator or agent of the present invention, including combinations thereof, versus a different agent.

In accordance with the above, an assay system for screening potential drugs effective to modulate innate immune response, particularly to HIV, may be prepared. The HIV Gag or capsid protein, for example may be introduced into a test system, and the prospective drug may also be introduced into the resulting cell culture, and the culture thereafter examined to observe any changes in the activity of the cells, or amount and extent of immune response indicator activity (for example CD86, IFN, or interferon response gene) due either to the addition of the prospective drug alone, or due to the effect of added quantities of the known agent(s).

Nucleic Acids

The present invention further provides an isolated nucleic acid encoding a protein, peptide, immune activator or agent of the present invention. Nucleic acid includes DNA and RNA. In a preferred aspect, the present invention provides a nucleic acid which codes for a polypeptide of the invention as defined above, including a polypeptide of HIV Gag or capsid as set out herein, particularly cyclophilin binding regions, domains or peptides.

The present invention also provides constructs in the form of plasmids, vectors, transcription or expression cassettes which comprise at least one polynucleotide as above. The present invention also provides a recombinant host cell which comprises one or more constructs as above. A nucleic acid encoding any specific binding member as provided itself forms an aspect of the present invention, as does a method of production of the specific binding member which method comprises expression from encoding nucleic acid therefor. Expression may conveniently be achieved by culturing under appropriate conditions recombinant host cells containing the nucleic acid. Following production by expression a specific binding member may be isolated and/or purified using any suitable technique, then used as appropriate.

Systems for cloning and expression of a polypeptide in a variety of different host cells are well known. Suitable host cells include bacteria, mammalian cells, yeast and baculovirus systems. Mammalian cell lines available in the art for expression of a heterologous polypeptide include Chinese hamster ovary cells, HeLa cells, baby hamster kidney cells, NSO mouse melanoma cells and many others. A common, preferred bacterial host is E. coli. The expression of antibodies and antibody fragments in prokaryotic cells such as E. coli is well established in the art.

Suitable vectors can be chosen or constructed, containing appropriate regulatory sequences, including promoter sequences, terminator sequences, polyadenylation sequences, enhancer sequences, marker genes and other sequences as appropriate. Vectors may be plasmids, viral e.g. 'phage, or phagemid, as appropriate. For further details see, for example, Molecular Cloning: a Laboratory Manual: 2nd edition, Sambrook et al., 1989, Cold Spring Harbor Laboratory Press. Many known techniques and protocols for manipulation of nucleic acid, for example in preparation of nucleic acid constructs, mutagenesis, sequencing, introduction of DNA into cells and gene expression, and analysis of proteins, are described in detail in Short Protocols in Molecular Biology, Second Edition, Ausubel et al. eds., John Wiley & Sons, 1992. The disclosures of Sambrook et al. and Ausubel et al. are incorporated herein by reference.

Thus, a further aspect of the present invention provides a host cell containing nucleic acid as disclosed herein. A still further aspect provides a method comprising introducing such nucleic acid into a host cell. The introduction may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. For bacterial cells, suitable techniques may include calcium chloride transformation, electroporation and transfection using bacteriophage. The introduction may be followed by causing or allowing expression from the nucleic acid, e.g. by culturing host cells under conditions for expression of the gene. The present invention also provides a method which comprises using a construct as stated above in an expression system in order to express a specific binding member or polypeptide as above.

Another feature of this invention is the expression of DNA sequences contemplated herein, particularly encoding the HIV Gag or capsid peptide, immune activator or agent of the invention. As is well known in the art, DNA sequences may be expressed by operatively linking them to an expression control sequence in an appropriate expression vector and employing that expression vector to transform an appropriate unicellular host. A wide variety of host/expression vector combinations may be employed in expressing the DNA sequences of this invention. Useful expression vectors, for example, may consist of segments of chromosomal, non-chromosomal and synthetic DNA sequences. Suitable vectors include derivatives of SV40 and known bacterial plasmids, e.g., E. coli plasmids col El, pCR1, pBR322, pMB9 and their derivatives, plasmids such as RP4; phage DNAs, e.g., the numerous derivatives of phage λ, e.g., NM989, and other phage DNA, e.g., M13 and filamentous single stranded phage DNA; yeast plasmids such as the 2u plasmid or derivatives thereof; vectors useful in eukaryotic cells, such as vectors useful in insect or mammalian cells; vectors derived from combinations of plasmids and phage DNAs, such as plasmids that have been modified to employ phage DNA or other expression control sequences; and the like.

Any of a wide variety of expression control sequences—sequences that control the expression of a DNA sequence operatively linked to it—may be used in these vectors to express the DNA sequences of this invention. Such useful expression control sequences include, for example, the early or late promoters of SV40, CMV, vaccinia, polyoma or adenovirus, the lac system, the trp system, the TAC system, the TRC system, the LTR system, the major operator and promoter regions of phage λ, the control regions of fd coat protein, the promoter for 3-phosphoglycerate kinase or other glycolytic enzymes, the promoters of acid phosphatase (e.g., Pho5), the promoters of the yeast-mating factors, and other sequences known to control the expression of genes of prokaryotic or eukaryotic cells or their viruses, and various combinations thereof.

A wide variety of unicellular host cells are also useful in expressing the DNA sequences of this invention. These hosts may include well known eukaryotic and prokaryotic hosts, such as strains of E. coli, Pseudomonas, Bacillus, Streptomyces, fungi such as yeasts, and animal cells, such as CHO, YB/20, NSO, SP2/0, R1.1, B-W and L-M cells, African Green Monkey kidney cells (e.g., COS 1, COS 7, BSC1, BSC40, and BMT10), insect cells (e.g., Sf9), and human cells and plant cells in tissue culture.

It will be understood that not all vectors, expression control sequences and hosts will function equally well to express the DNA sequences of this invention. Neither will all hosts function equally well with the same expression system. However, one skilled in the art will be able to select the proper vectors, expression control sequences, and hosts without undue experimentation to accomplish the desired expression without departing from the scope of this invention. In selecting an expression control sequence, a variety of factors will normally be considered. These include, for example, the relative strength of the system, its controllability, and its compatibility with the particular DNA sequence or gene to be expressed, particularly as regards potential secondary structures. Suitable unicellular hosts will be selected by consideration of, e.g., their compatibility with the chosen vector, their secretion characteristics, their ability to fold proteins correctly, and their fermentation requirements, as well as the toxicity to the host of the product encoded by the DNA sequences to be expressed, and the ease of purification of the expression products. Considering these and other factors a person skilled in the art will be able to construct a variety of vector/expression control sequence/host combinations that will express the DNA sequences of this invention on fermentation or in large scale animal culture.

The invention may be better understood by reference to the following non-limiting Examples, which are provided as exemplary of the invention. The following examples are presented in order to more fully illustrate the preferred embodiments of the invention and should in no way be construed, however, as limiting the broad scope of the invention.

EXAMPLE 1

Introduction

While the T cell response to HIV-1 has been studied extensively in humans, the role of cells involved in the innate response to HIV-1 and other retroviruses has received relatively little attention. Dendritic cells (DC) play a major role in detecting and initiating the response to pathogens, thus linking the innate immune response to adaptive immunity. They serve as early response sensors of microbial infection and also as specialized antigen presenting cells in the induction of T cell responses (Steinman et al., 2006; Takeuchi et al., 2009). They are also likely to play a role in the innate response to HIV-1, as shown for instance by the dense network of DC at mucosal surfaces where HIV-1 enters the organism and replicates extensively early after transmission (Veazey et al., 2003).

Host cells recognize the invasion of viruses and mount strong antiviral responses. Viruses initially activate the innate immune system, which recognizes viral components through pattern-recognition receptors (PRRs). Acquired immunity plays a major role in the responses to re-infection with viruses. Host PRRs detect viral components, such as genomic DNA, single-stranded RNA (ssRNA), double-stranded RNA (dsRNA), RNA with 5'-triphosphate ends and viral proteins. Currently, three classes of PRRs have been shown to be involved in the recognition of virus-specific components in innate immune cells, namely Toll-like receptors (TLRs), retinoic acid-inducible gene I (RIG-I)-like receptors (RLRs), and nucleotide oligomerization domain (NOD)-like receptors (NLRs). Among these receptor types, TLRs and RLRs are important for the production of type I interferons (IFNs) and various cytokines. Detection of viral components by RLRs and TLRs in immune cells activates intracellular signaling cascades, leading to the secretion of type I IFNs, proinflammatory cytokines and chemokines, and increased expression of costimulatory molecules such as CD40, CD80, and CD86.

Innate detection of viral elements has been mostly observed for viral nucleic acids (Takeuchi et al., 2009). In vesicular compartments, TLR3 and TLR7 recognize dsRNA and ssRNA, respectively. In the cytoplasm, AIM2, RIG-I and MDA5 recognize DNA, dsRNA, 5'-triphosphage ssRNA, respectively. For retroviruses, TREX1 has been shown to play a role in the catabolism of viral cDNA (Stetson et al., 2008). In addition, Myd88 was shown to play a role in in vivo clearance of Friend MLV infection (Browne et al., 2009). In the case of HIV-1, TLR7/8 expressed in pDC can recognize ssRNA derived from HIV-1 RNA following endocytosis of HIV-1 particles (Beignon et al., 2005; Heil et al., 2004).

High multiplicities of infection (MOI) or long-term cultures are usually utilized to achieve substantial HIV-1 infection of monocyte-derived cells (Gendelman et al., 1990; Izmailova et al., 2003; Woelk et al., 2004; Szebeni et al., 1991; Harman et al., 2009). In fact, it was found HIV-1 infection of monocyte-derived dendritic cells is restricted (Negre et al., 2000). Incubation of dendritic cells with SIVmac particles containing Vpx are able to alleviate the restriction and allow complete infection of dendritic cells at standard MOI in a single round of infection (Mangeot et al., 2002; Goujon et al., 2006). We took advantage of this system to explore the innate response of HIV-1 in monocyte-derived dendritic cells.

Pathogens induce an innate response through pattern-recognition receptors (Steinman et al., 2006). This shapes the subsequent adaptive immune response appropriately. While the innate response to several viruses is known (Takeuchi et al., 2009), the response to HIV-1 has remained elusive. We describe a method for inducing the innate response to HIV-1. This method leads to the up-regulation of activation markers, including co-stimulatory molecules for effective activation of T cells, and to the secretion of type-I interferon by dendritic cells. This approach can potentially be implemented in vaccine strategies.

Results

Figure 2:
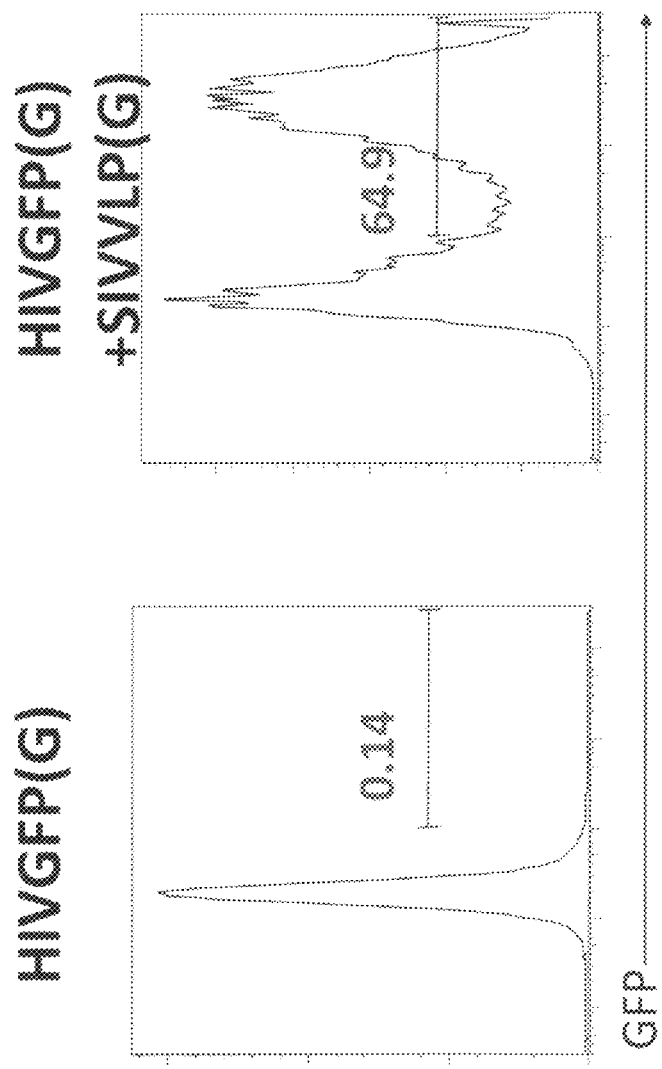
FIG. 2 shows that co-infection of MDCC with HIVGFP(G) and SIVVLP(G) vectors renders MDCC susceptible to HIV-1 infection.

HIV-1 is inefficient at infecting monocyte-derived dendritic cells. Using SIVmac virus-like particles carrying Vpx alleviates this restriction (Goujon et al., 2006). Using a combination of GFP-encoding HIV-1 defective vector (HIVGFP (G)) and SIVmac particles (SIVVLP(G)) (FIG. 1), we are able to infect 99% of the dendritic cells (FIG. 2).

Figure 3:
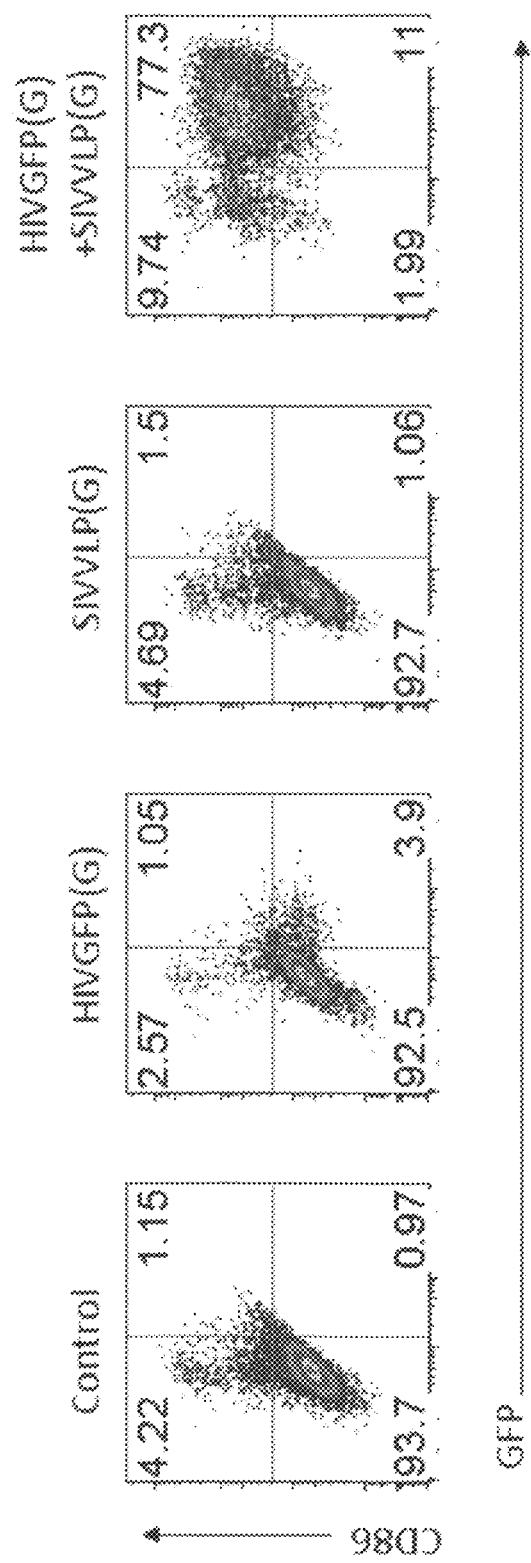
FIG. 3 depicts induction of dendritic cell activation by HIVGFP(G)+SIVVLP(G). Monocyte-derived dendritic cells (MDDC) were infected with HIVGFP(G) and SIVVLP(G) alone or in combination. CD86 and GFP expression were measured at 48 h. In the presence of SIVVLP(G), HIVGFP(G) is able to infect MDDC (as shown by GFP infection) and induces activation (as shown by the upregulation of the costimulatory molecule CD86).
Figure 4:
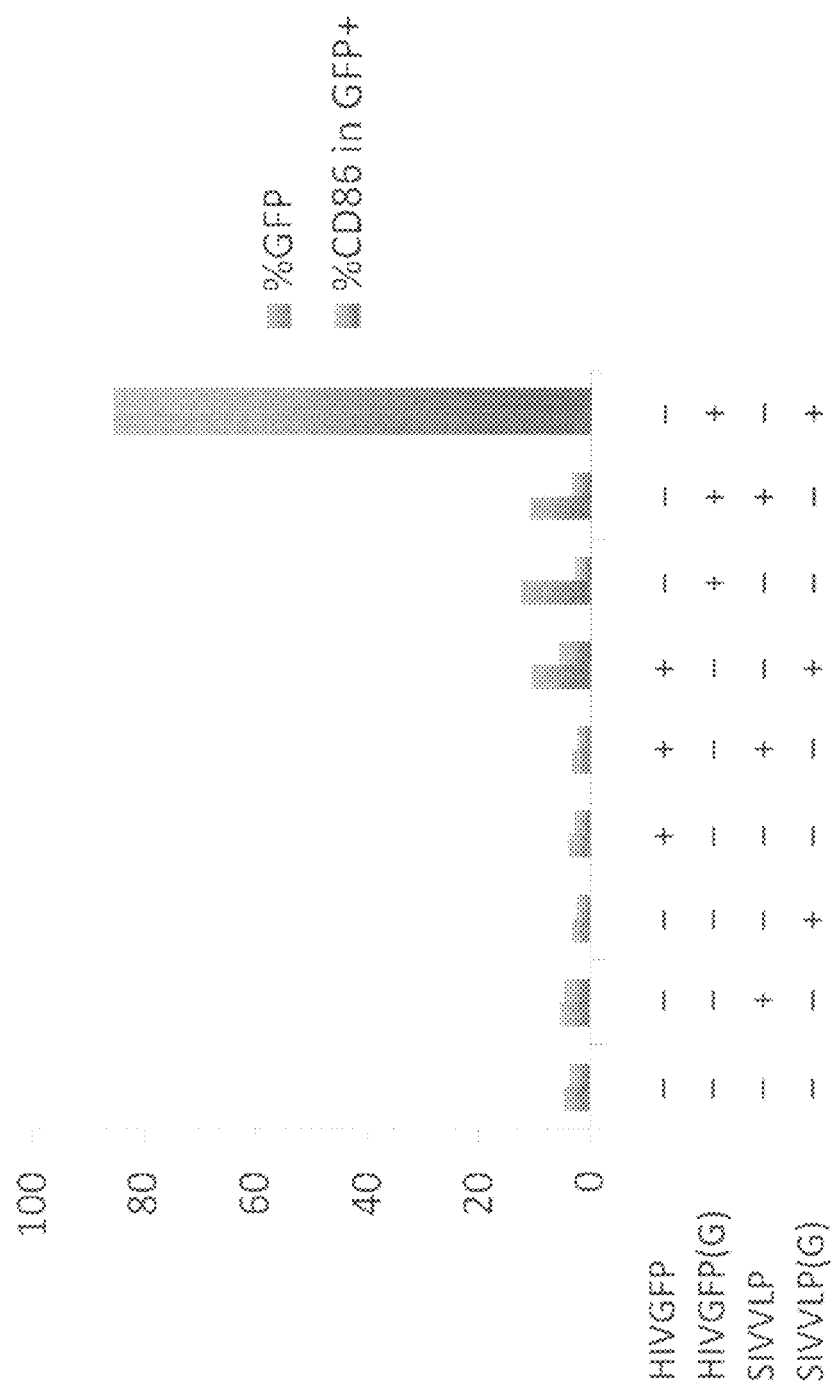
FIG. 4 activation of dendritic cells as assessed by CD86 requires entry of HIV-1 and of SIV VLP.
Figure 5:
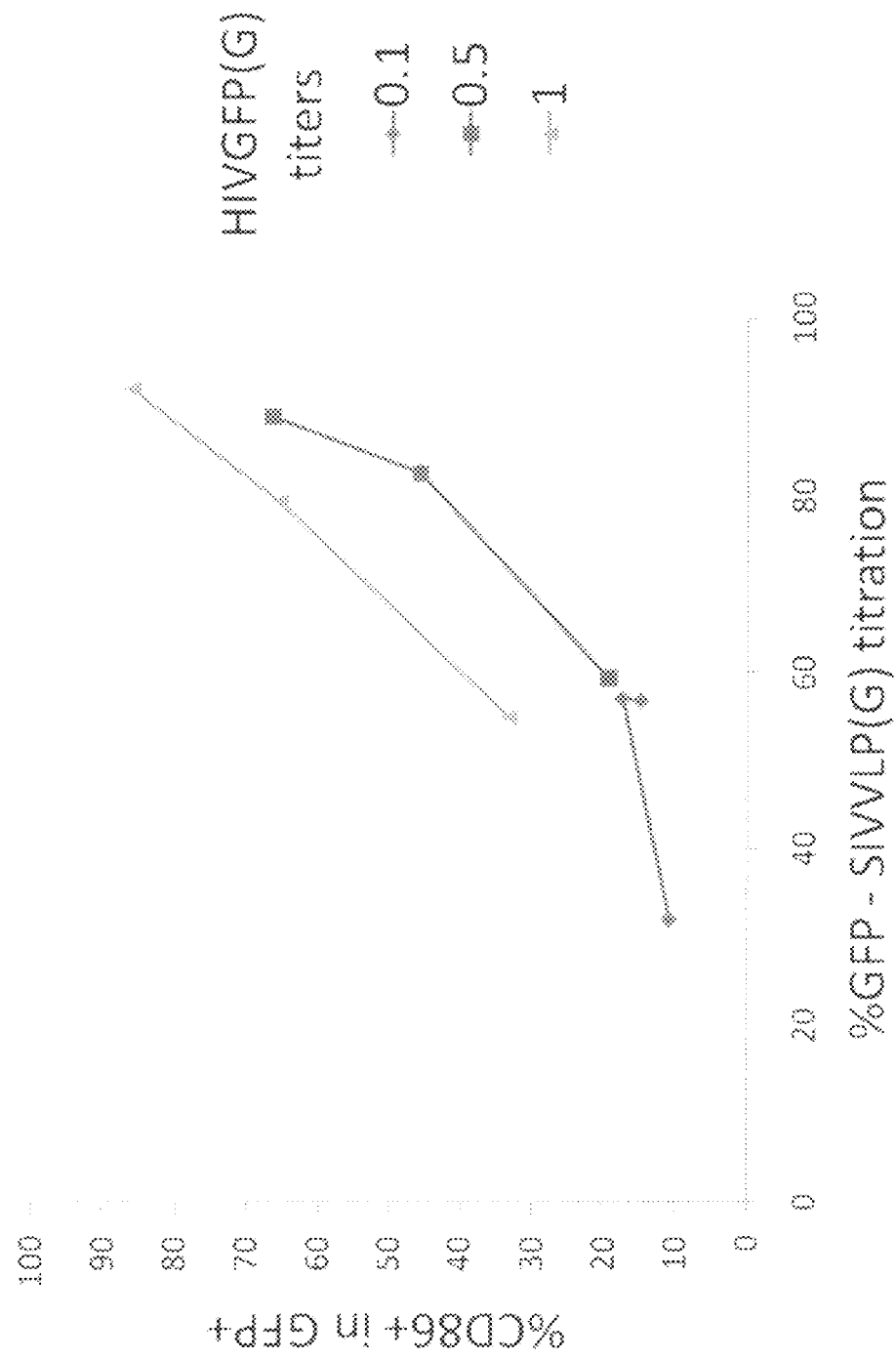
FIG. 5 activation with wild-type Capsid requires high levels of infection. Percent CD86 in GFP+ is graphed versus % GFP at various HIV titers.

We found that this induces the up-regulation of activation markers CD86, CD80, CD38, CD83. Monocyte-derived dendritic cells (MDDC) were infected with HIVGFP(G) and SIVVLP(G) alone or in combination. CD86 and GFP expression were measured at 48 h. In the presence of SIVVLP(G), HIVGFP(G) is able to infect MDDC (as shown by GFP infection) and induces activation (as shown by the upregulation of the costimulatory molecule CD86) (FIG. 3). This activation required a entry of HIV-1 and SIV VLP (FIG. 4). Further, activation using the wild-type Capsid required a high level of infection (FIG. 5).

Figure 6:
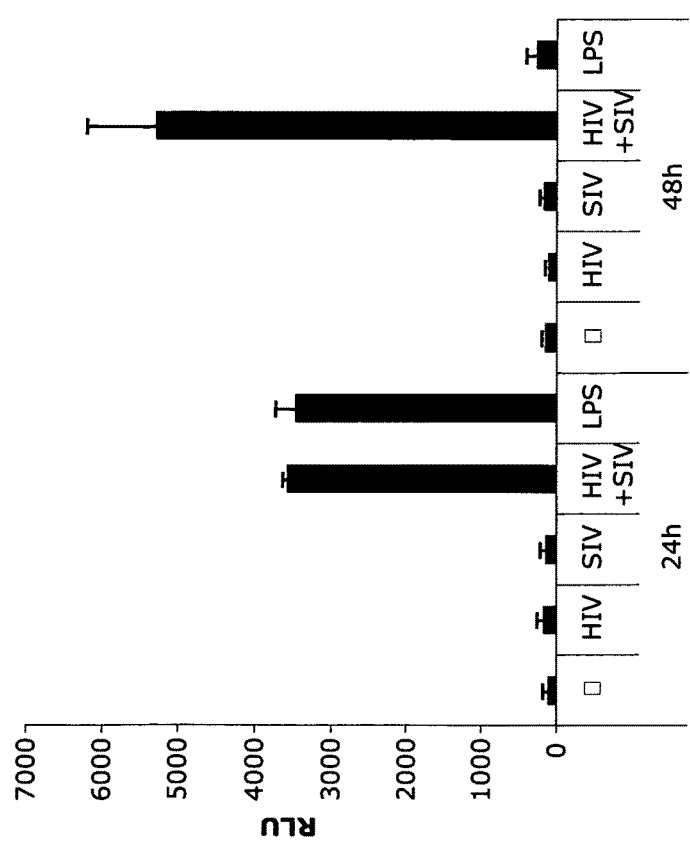
FIG. 6 depicts production of type-I interferon by HIVGFP(G)+SIVVLP(G). Interferon was measured in culture supernatants of MDDC infected with HIVGFP(G), SIVVLP(G) or treated with LPS. A reporter cell line was used to measure the production of interferon.
Figure 7:
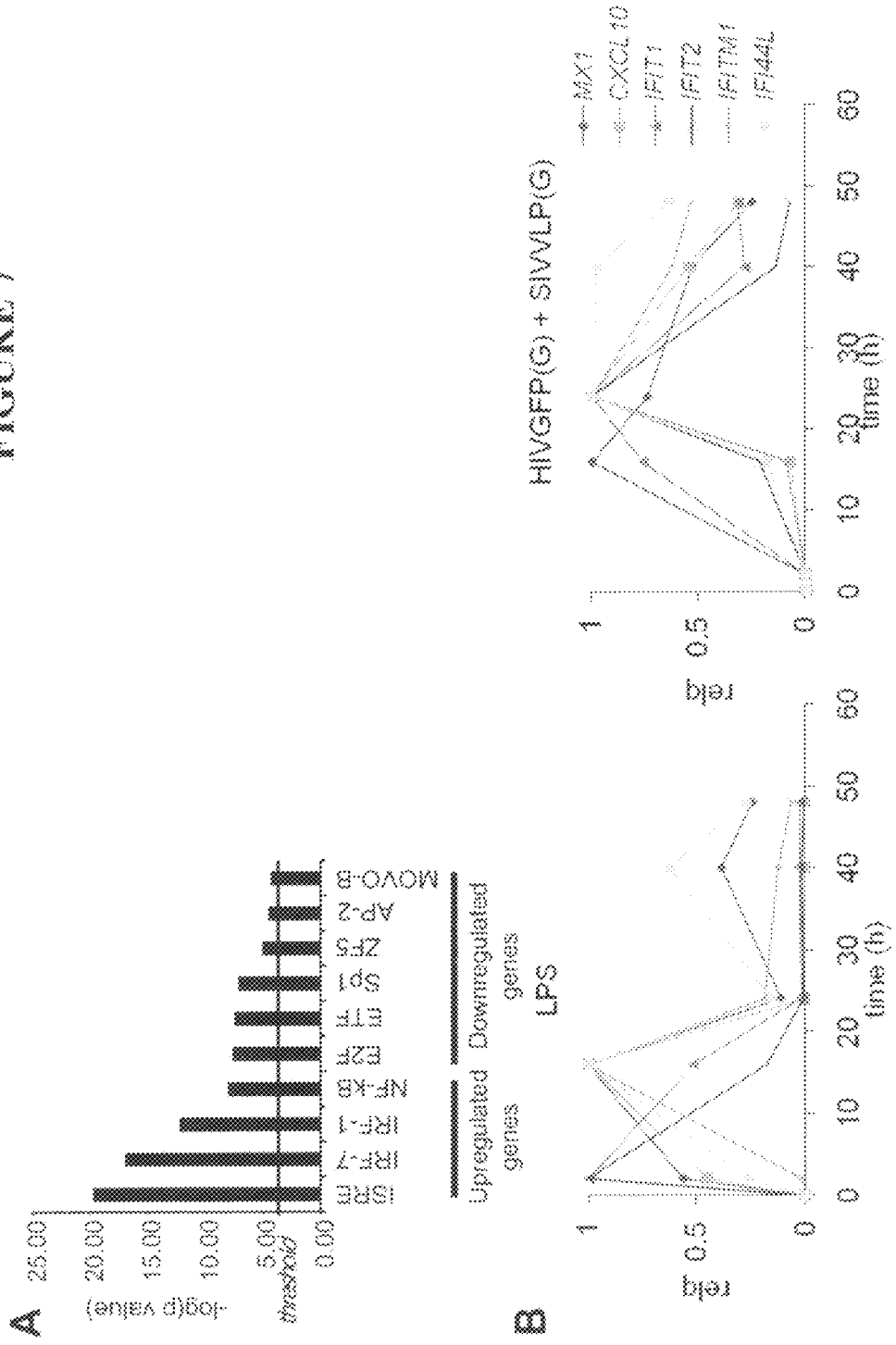
FIGS. 7A and 7B shows that HIV-1/SIV infection of MDCC induces Type-I interferon responsive genes, as assessed by transcription factor binding site analysis in the promoters of upregulated genes. (A) Transcription factor binding sites that were significantly enriched in the promoter region of the up-regulated and down-regulated genes. P value was generated using a random background set of promoters. (B) Time-course RT-PCR analysis of MX1, CXCL10, IFIT1, IFIT2, IFITM1 and IFI44L expression relative to ACTB in MDDC infected with HIVGFP(G) and SIVVLP(G) or treated with LPS.

HIV/SIV infection of MDCC induces a type-I interferon response (FIG. 6) and the expression of Type-I interferon response signature genes (for example mx1, cxcl10, ifit1, ifit2). Interferon was measured in culture supernatants of MDDC infected with HIVGFP(G), SIVVLP(G) or treated with LPS. A reporter cell line was used to measure the production of interferon. Also, transcription factors ISRE, IRF-7, IRF-1 and NF-kB were above threshold by transcription factor binding site analysis in the promoters of IFN-upregulated genes (FIGS. 7A and 7B). The table below lists exemplary genes in TLR signaling network that are significantly affected by MDDC infection with HIVGFP(G) and SIVVLP(G). P value generated using a random background set of promoters.

| Promoter | Direction | p value |
|---|---|---|
| ISRE | Upregulated | 1.90E−20 |
| IRF-7 | Upregulated | 1.10E−17 |
| IRF-1 | Upregulated | 5.90E−13 |
| NF-kB | Upregulated | 1.00E−08 |
| E2F | Downregulated | 2.60E−08 |
| ETF | Downregulated | 3.80E−08 |
| Sp1 | Downregulated | 8.90E−08 |
| ZF5 | Downregulated | 1.10E−05 |
| AP-2 | Downregulated | 3.70E−05 |
| MOVO-B | Downregulated | 6.60E−05 |

Early steps of HIV infection were required for activation, as assessed by CD86 determination in GFP+ in the presence or absence of viral inhibitors AZT and/or RAL. Addition of AZT or RAL within the first 24 hours of infection blocked activation.

Figure 9D:
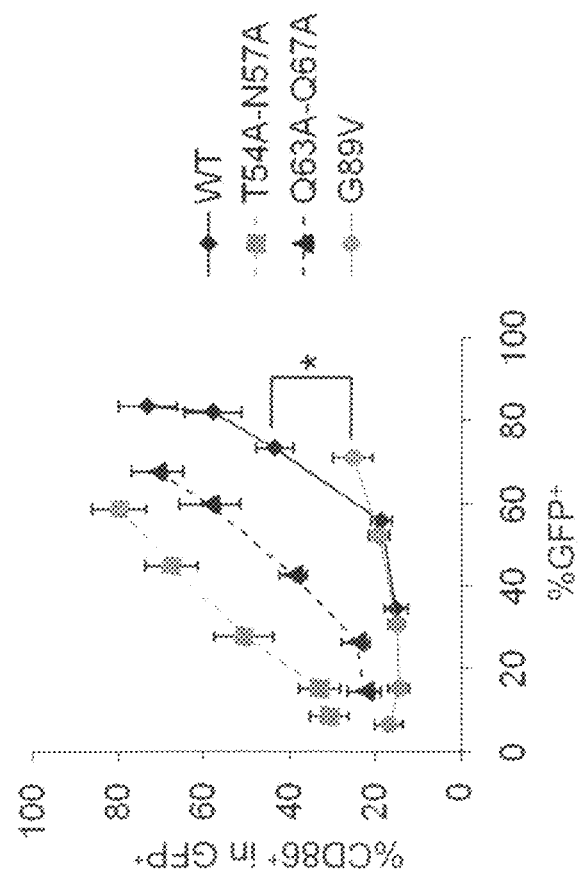
FIGS. 9A, 9B and 9C depicts inhibition or improvement of the activation by Capsid mutants. (A) In order to determine which part of HIV-1 was responsible for activation, several mutants were generated. PR D25N is a catalytic mutant of the viral protease and prevents maturation. This mutant still activated MDDC, albeit to a lesser extent. ΔGag is a deletion of Gag. It does not induce CD86 expression. PTAP- is a budding mutant and it induces CD86 expression. ΔRev is a mutant lacking Rev, leading to splicing of the genomic RNA and thus no expression of Gag. This indicates that activation most likely maps to a Gag determinant, after integration/expression, but before budding. (B) Effect of CA mutations on proportion of GFP+ infected MDDC that express CD86. MDDC were infected with serially diluted wild-type (WT) pLaiΔEnv-GFP3(G) or CA mutants T54A/N57A, Q63A/Q67A or Q89V, in the presence of SIVVLP(G). CA mutant infectivity was rescued by co-expression of wild-type proteins in packaging cells. * p<0.026 (n=9). Mutants T54A/N57A and Q63A/Q67A decrease the threshold of activation. G89V does not induce significant activation. (C) Mutants A92E and G94D decrease the threshold of activation. P90A, P90A-A92E and P90A-G94D do not induce significant activation.

The activation and response is not induced by defective HIV-1 vectors lacking Gag (FIG. 9A e.g. lentiviral vectors used to express heterologous genes). Various capsid mutants were evaluated by assessing activation markers with increasing amounts of HIVGFP (FIGS. 9B and 9C). Mutants of Capsid T54N-N57A, Q63A-Q67A, A92E, G94D are more efficient at inducing the activation. Thus, mutants T54A-N57A, Q63A-Q67A, A92E and G94D all decrease the threshold of activation. On the contrary, mutants P90A, G89V, P90A-A92E and P90A-G94D, which disrupt Cyclophilin A binding, do not induce significant activation.

Figure 10:
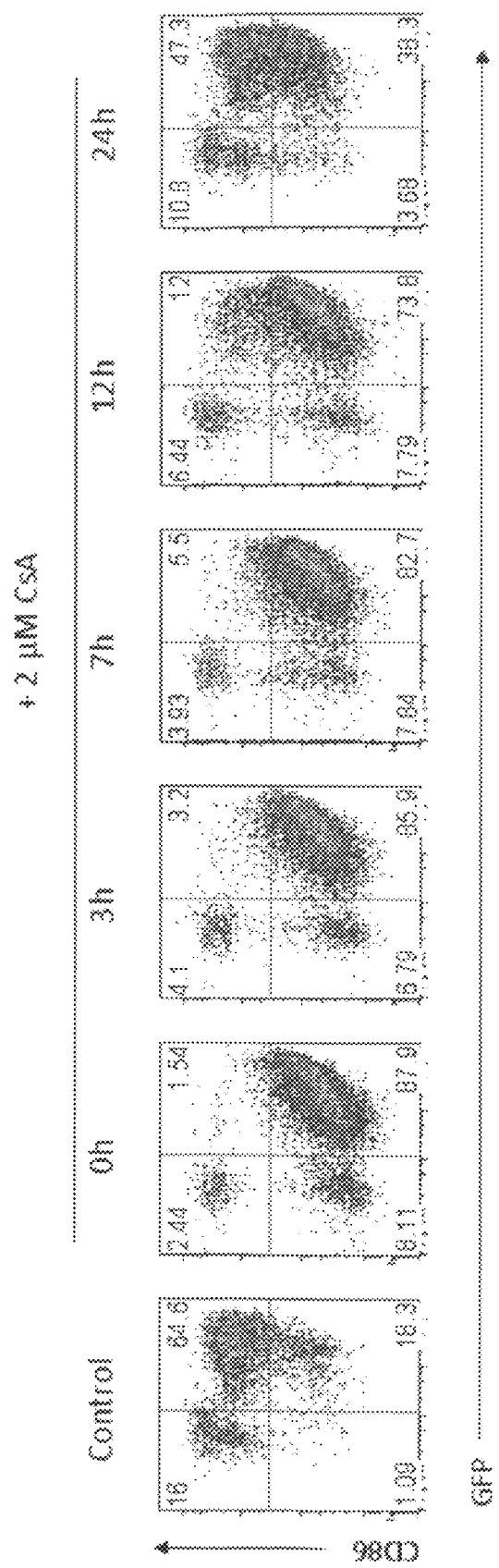
FIG. 10 depicts inhibition of the activation by HIVGFP(G)+SIVVLP(G) using Cyclosporin A. MDDC were infected with HIVGFP(G)+SIVVLP(G), and treated at different time points with Cyclosporin A. CD86 and GFP expression were measured at 48 h. Up to 24 h, Cyclosporin A (CsA) reduces CD86 expression. CsA is known to reduce infectivity of incoming virions, during the early phase of infection which occurs between 0 h to 12 h. The low concentration of CsA and its addition up to 24 h after infection discard any effect of CsA on infection itself, as shown by the constant proportion of GFP+ cells. This indicates that CsA acts on de novo synthesized Capsid, and not on Capsid from incoming viral particles.

Cyclosporin A treatment upon infection and up to 12 hours after infection prevents the activation (FIG. 10). MDDC were infected with HIVGFP(G)+SIVVLP(G), and treated at different time points with Cyclosporin A. CD86 and GFP expression were measured at 48 h. Up to 24 h, Cyclosporin A (CsA) reduces CD86 expression. Cyclosporin A inhibits Cyclophilin A (PPIA), which normally binds to the HIV-1 Capsid at residue P90A (Reimer et al., 1997). CsA is known to reduce infectivity of incoming virions, during the early phase of infection which occurs between 0 h to 12 h. The low concentration of CsA and its addition up to 24 h after infection circumvent any effect of CsA on infection itself, as shown by the constant proportion of GFP+ cells. This indicates that CsA acts on de novo synthesized Capsid, and not on Capsid from incoming viral particles.

An RNAi strategy was employed to further explore the activation and cellular gene response(s). MDDC were transduced at day 0 with control, IRF3 or PPIA shRNA small hairpin RNA (shRNA) vectors in the presence of SIVVLP (G). At day 4, cells were challenged with HIV (encoding RFP), polyIC or LPS. At day 6 activation (CD86 and CD38) and infection (RFP) were measured. IRF3 was inhibited by various shRNA constructs as depicted in FIG. 11. Inhibition of IRF3 (which induces type-I interferon) or PPIA (cyclophilin A) expression using small interfering RNA prevents the activation (FIG. 12). Therefore, activation by HIV-1 requires cyclophilin and also independently requires a functioning Type-I interferon response system, particularly mediated by IRF-3.

These results demonstrate that efficient HIV-1 infection of MDCC can be achieved with SIV VLP, and that activation of innate immune responses can be achieved in this system. Specific activation markers, including CD86 are upregulated. Interferon-response genes are expressed and Type-I interferon is produced. This cell activation on HIV infection requires early steps of infection and Gag. The activation can be blocked by shRNAs designed against particular components of the activation response, including PPIA (CyclophilinA) and IRF3.

Materials and Methods

Cells: GHOST and 293FT (Invitrogen) were cultured in DMEM, 10% fetal bovine serum (FBS) (HyClon) and antibiotics. PBMC were isolated from IRB-approved buffy coats from normal donors. CD14+ cells were isolated by double positive selection with anti-human CD14 magnetic beads (Miltenyii). Purity was at least 99%. CD14+ were culture in RPMI, 10% FBS, antibiotics and HEPES in the presence of recombinant human GM-CSF at 10 ng/ml and IL-4 at 50 ng/ml (eBioscience). Fresh media was added at day 3, and cells were stimulated or infected at day 4.

Reagents: LPS (lipopolysaccharide) and pIC (polyriboinosinic:polyribocytidylic acid) were from Sigma. Cyclosporin A, FK506 and Rapamycin were from Calbiochem. AZT (Zidovudine), RAL (Raltegravir), NFV (Nelfinavir), LPV (Lopinavir), SQV (Saquinavir), TPV (Tipranavir) were obtained through the NIH AIDS Research & Reference Reagent Program.

Infection and stimulation: At day 4 of differentiation, cells were harvested, counted and resuspended in their own media at a concentration of one million/ml and 100 µl were aliquoted in round bottom 96-well plates. For infection, 50 µl of media or SIVVLP(G) were first added. 100 µl of media or various dilutions of various HIV-1-derived viral preparations were then added. NFV, SQV, TPV, AZT and RAL were added at 10 Neutralizing anti-IFNα, anti-IFNβ were added at 20 µg/ml.

Western blot analysis: Cells were lysed in 1% NP-40, 50 mM Tris pH 8, 120 mM NaC, 4 mM EDTA, 50 mM NaF, 1 mM $NA_3VO_4$ and a protease inhibitors cocktail (Roche). Total lysates were resolved on SDS-PAGE, transferred to PVDF membranes and probed with primary antibodies and corresponding HRP-conjugated secondary antibodies.

IFN assay: Developed by Yaming Wang and David E. Levy (NYU). A cell line carrying a Luciferase gene under the control of an interferon-response element (ISRE) was generated. This cell line responds to all isoforms of type-I interferon. Upon addition of recombinant interferon or supernatant containing interferon, Luciferase is induced. Luciferase activity is then measured by a standard luminescence assay. Recombinant IFN-a2 is used for generating a standard curve.

Microarray analysis: Cells were infected with HIVGFP (G), SIVVLP(G), both or treated with LPS. Cells harvested after 48 h. A subset was analyzed by flow cytometry. RNA was prepared with TRIZOL and microarray data generation was done using standard protocols on Human Genome U133A 2.0 arrays (Elkon et al., 2003). Promoter analysis was performed using PRIMA2 in EXPANDER3 (Shamir et al., 2005). TLR Pathway analysis was performed using SPIKE4 (Elkon et al., 2008).

Electron microscopy: Dendritic cells were infected with HIVGFP(G) and SIVVLP(G) with or without NFV. Cells were fixed and processed for transmission electron microscopy analysis. Images were taken on a Philipps CM12 microscope.

qPCR: qPCR analysis was performed essentially as described (Manel et al., 2008) using the standard curve method or the ΔCt method (primers sets, Table 2).

Plasmids: HIVGFP is env⁻vpu⁻vpr⁻vif⁻nef⁻, GFP in nef, has already been described (Unutmaz et al., 1999). HIVGFP ΔRev was generated by mutating the start codon of Rev. HIVGFP PTAP⁻ was generated by mutating PTAP to LIRL. HIVGFP D52N is a point mutation of protease. HIVGFP P90A, A92E, G94D, P90A-A92E and P90A-G94D are point mutants in CA. HIVGFP ΔGag was generating by inserting a stop codon after 7 amino acids of Gag. VPX-VPR fusion protein was generated by fusing SIVmac251 Vpx with HIV-1 NL4-3 Vpr using the linker ANYAAAAAAADPS (SEQ ID NO: 17) in pIRE2EGFP. LKO1gfp was generated by replacing the puro$^R$ ORF in pLKO1puro7 with EGFP. shRNA were designed as described previously (Moffat et al., 2006) (Table 3), except that a partial mir30 sequence CTGTGAAGCCACAGATGGG (SEQ ID NO: 18) was used for the loop. shRNA were then cloned as described (Moffat et al., 2006). T54A/N57A, Q63AQ67A, G89V and the parental vector are env⁻nef⁻, GFP in nef, and were already described (Yamashita et al., 2007).

Virus production: Viral particles were produced by transfection of 293FT cells with 3 µg DNA and 8 µl TransIT-293 (Mints Bio); for shRNA vectors, 0.4 µg CMV-VSVG, 1 µg pCMV-ΔR8.91 and 1.6 µg shRNA were used; for SIVVLP (G), 0.4 µg CMV-VSVG and 2.6 µg pSIV3+9; for HIVGFP (G), 0.4 µg CMV-VSVG and 2.6 µg HIVGFP; for NL4-3-deltaE-EGFP, 0.4 µg pCMV-VSVG and 2.6 µg pNL4-3-deltaE-EGFP10. HIVGFP ΔRev, HIVGFP PTAP⁻ and HIVGFP D52N were produced with 0.4 µg CMV-VSVG, 0.5 µg pCMV-ΔR8.91 and 2.1 µg HIV plasmid. HIVGFP ΔGag and CA mutants were produced with 0.4 µg CMV-VSVG, 1 µg pCMV-ΔR8.91 and 1.6 µg HIV plasmid.

shRNA transduction: Five million freshly isolated CD14+ cells were cultured in 5 ml of media containing GM-CSF, IL-4, and 5 µg/ml polybrene. One ml of SIVVLP(G) supernatant and 2.5 ml of shRNA vector supernatant were added to cells. At day 1 and 3, 2 ml of fresh media was added. At day 4, cells were transduced at more than 96% based on GFP expression and were used for further infections and stimulation as above.

TABLE 1

Antibodies used in this study

| Target | Company | Clone or Reference |
|---|---|---|
| actin | Sigma | AC-40 |
| CD11c | eBioscience | 3.9 |
| CD14 | eBioscience | 61D3 |
| CD16 | eBioscience | CB16 |
| CD19 | eBioscience | HIB19 |
| CD20 | eBioscience | 2H7 |
| CD25 | eBioscience | BC96 |
| CD3 | eBioscience | UCHT1 |
| CD3 | Hybridoma (ATCC) | OKT3 |
| CD38 | eBioscience | HIT2 |
| CD4 | eBioscience | RPA-T4 |
| CD45RA | eBioscience | HI100 |
| CD45RO | eBioscience | UCHL1 |
| CD56 | eBioscience | MEM-188 |
| CD80 | eBioscience | 2D14.4 |
| CD83 | eBioscience | HB15e |
| CD86 | eBioscience | IT2.2 |
| CypA | Wes Sundquist lab | UT96 |
| HLA-DR | eBioscience | LN3 |
| IFNa | PBL | 31101-1 |
| IFNAR | PBL | MMHAR-2 |
| IFNb | PBL | 31401-1 |
| IFNg | eBioscience | 4S.B3 |
| IRF3 | IBL | 18781 |
| Lamin B1 | Santa Cruz Biotechnology | sc-20682 |
| p24 | Dako | Kal-1 |
| p24 (intracellular) | Beckman Coulter | KC57 |
| p24CA | NIH AIDS Research & Reference Reagent Program | 183-H12-5C |
| p24CA | NIH AIDS Research & Reference Reagent Program | #24-2 |
| p24CA | NIH AIDS Research & Reference Reagent Program | #24-4 |
| p50 | eBioscience | 14-6732 |
| Phospho-Ser396-IRF3 | Cell Signaling | 4947 |
| phospho-Y690-Stat2 | David Levy lab | Custom |
| phospho-Y701-Stat1 | Inivitrogen | 333400 |

TABLE 2

Primer sets used in this study

| Target | Forward sequence | Reverse sequence |
|---|---|---|
| ACTB | GGACTTCGAGCAAGAGATGG (SEQ ID NO: 19) | AGCACTGTGTTGGCGTACAG (SEQ ID NO: 20) |
| CXCL10 | TGGCATTCAAGGAGTACCTC (SEQ ID NO: 21) | TTGTAGCAATGATCTCAACACG (SEQ ID NO: 22) |
| IFIT1 | CAACCATGAGTACAAATGGTG (SEQ ID NO: 23) | CTCACATTTGCTTGGTTGTC (SEQ ID NO: 24) |
| IFIT2 | AGGTCTCTTCAGCATTTATTGG (SEQ ID NO: 25) | TATTGTTCTCACTCATGGTTGC (SEQ ID NO: 26) |
| IFITM1 | TACTCCGTGAAGTCTAGGGA (SEQ ID NO: 27) | TAATATGGTAGACTGTCACAGAGC (SEQ ID NO: 28) |
| IFI44L | AACTGTGGTATAGCATATGTGG (SEQ ID NO: 29) | CTCTCAATTGCACCAGTTTCC (SEQ ID NO: 30) |
| PPIA | GTCTCCTTTGAGCTGTTTGC (SEQ ID NO: 31) | CGTATGCTTTAGGATGAAGTTCTC (SEQ ID NO: 32) |
| IRF3 | CCCTTCATTGTAGATCTGATTACC (SEQ ID NO: 33) | TGCAGGTCCACAGTATTCTC (SEQ ID NO: 34) |

TABLE 3 shRNA used in this study

| Target | Identifier | Hairpin sequence |
|---|---|---|
| IRF3 | sh1 | CTGCCTGGATGGCCAGTCACAC (SEQ ID NO: 35) |
| IRF3 | sh2 | CATTGTAGATCTGATTACCTTC (SEQ ID NO: 36) |
| IRF3 | sh3 | GCCACACATACTGGGCAGTGAG (SEQ ID NO: 37) |
| IRF3 | sh4 | GCCTCAGGGCCTTGGTAGAAAT (SEQ ID NO: 38) |
| IRF3 | sh5 | TACCCAGGAAGACATTCTGGAT (SEQ ID NO: 39) |
| PPIA | sh1 | CTGGCATCTTGTCCATGGCAAA (SEQ ID NO: 40) |
| PPIA | sh2 | GGTTCCTGCTTTCACAGAATTA (SEQ ID NO: 41) |
| PPIA | sh3 | TGTGGTGTTTGGCAAAGTGAAA (SEQ ID NO: 42) |

EXAMPLE 2

It has been previously demonstrated that an interaction of the Gag polyprotein precursor Pr55gag with human recombinant cytosolic Cyclophilin A (Cyp18/PPIA) is necessary for replication of HIV type 1 (HIV-1) virions (Fischer, 1994; Luban et al., 1993; Franke et al., 1994; Thali et al., 1994; Braaten et al., 1996a; Braaten et al., 1996b). The Gag polyprotein (Pr55$^{gag}$) of HIV-1 plays an important role in the assembly, infection and disassembly of the HIV virion (Gitti et al., 1996) and constitutes three major components: p17 matrix, p24 capsid and p7 nucleocapsid (Henderson et al.; 1992). Pr55gag has been shown to interact with host cell cyclophilins (Fischer, 1994; Luban et al., 1993; Franke et al., 1994; Thali et al., 1994; Braaten et al., 1996a; Braaten et al., 1996b). Cyclophilins are ubiquitously occurring peptidyl-prolyl cis/trans isomerases (PPIases; EC 5.2.1.8). PPIases have been found to guide protein folding by the catalytic acceleration of rate-limiting peptidyl-prolyl cis/trans isomerizations (Fischer et al., 1990) and likely play an important role in protein folding.

A proline-rich region with an indispensable Gly-Pro segment in Pr55gag was identified to be important for Cyclophilin A binding (Franke et al., 1994; Braaten et al., 1996b; Colgan et al., 1996). When Proline 90 (of the capsid protein) is changed to Ala, the interaction of Pr55gag with Cyclophilin A is abolished, resulting in a loss of virus infectivity (Colgan et al., 1996). Alteration of the other proline residues of the proline-rich array to alanine shows no detectable effect on the binding of Pr55gag to Cyp18 (Franke et al., 1994). Peptide fragments from this proline-rich region have been used to investigate the interaction of those peptides with Cyclophilin A and strong and selective binding of a peptide containing 25 amino acid residues from position 213 to 237 of Gag polyprotein was demonstrated with an IC50 of 180 µM (peptide Asp1-Arg2-Val3-His4-Pro5-Val6-His7-Ala8-Gly9-Pro10-Ile11-Ala12-Pro13-Gly14-Gln15-Met16-Arg17-Glu18-Pro19-Arg20-Gly21-Ser22-Asp23-Ile24-Ala25; SEQ ID NO: 16) (this fragment corresponds to residues 81-105 of HIV-1 p24 capsid protein) (Schutkowski et al., 1996). A second peptide sequence, modified from the above peptide by the replacement of Gly9 with Ala and a conservative change of Met16 to norleucine (Nle) also has activity (Reimer et al., 1997).

Although Cyclophilin A binding to HIV gag protein has been shown previously to be involved in HIV replication in the early phase of infection, the previous example now demonstrates that Cyclophilin A binding is critical for innate immune response to the HIV virion in the late phase of infection, including for dendritic cell response and activation. The above example shows that cyclosporine A treatment at or up to 24 hours after HIV infection prevents activation and upregulation of the costimulatory molecule CD86. Further, Gag mutants defective in cyclophilin binding, as shown in Example 1, are defective in activation and CD86 upregulation. Inhibition of IRF3 or PPIA (Cyclophilin A) using shRNA prevents activation and CD86 and CD38 upregulation. Therefore, Cyclophilin A binding is necessary for dendritic cell activation by HIV-1 specifically and modulation of Cyclophilin A binding now provides a novel approach to stimulating or facilitating innate immune response, particularly to HIV.

The incorporation of the HIV Gag Cyclophilin A binding peptide in a vaccine or in conjunction with presentation of HIV or HIV antigen(s) is now predicted to facilitate dendritic cell activation and innate immune response to HIV or HIV infection. The Cyclophilin A binding peptide, or peptides with mutated sequences showing enhanced activation (as demonstrated in Example 1), are provided in an HIV vaccine or HIV antigen mixture to facilitate innate immune response and dendritic cell activation. Peptides may be combined with or fused or otherwise covalently attached to a cell penetrating peptide or other peptide for enhanced cellular uptake or delivery. For example polybasic transactivator of HIV-transcription HIV-tat derived peptides have been shown and utilized to stimulate cellular uptake and intracellular delivery of various molecules, peptides, DNA and liposomes (Sandgren, S et al (2002) J Biol Chem 277(41):38877-38883; Torchilin, V P et al (2001) PNAS 98(15):8786-8791).

Peptide sequences may be selected from DRLHPVHAGPIAPGQMREPRGSDIA (SEQ ID NO: 15) (corresponding to cyclophilin binding peptide from HIV strain HIV-1 NL4-3) or any corresponding sequence from a known HIV subtype. A peptide may encompass the HIV-1 NL4-3 Cyclophilin A binding peptide fused to a Tat intracellular targeting peptide to be used as an adjuvant for an HIV-1 vaccine. This fused peptide sequence may be GRKKRRQRRRDRLHPVHAGPIAPGQMREPRGSDIA (SEQ ID NO: 43) (peptide #1). The Tat intracellular targeting sequence may be RKKRRQRRR (SEQ ID NO: 44). The CyclophilinA binding peptide may be DRLHPVHAGPIAPGQMREPRGSDIA (SEQ ID NO: 15). Derivates from the peptide #1 are generated corresponding to the same sequence region in known subtypes of HIV-1. Derivatives from the peptide #1 are generated in which residues are changed to a gain of function. As an example, the peptide corresponding to the gain of function mutant A92E is GRKKRRQRRRDRLHPVHAGPI<u>E</u>PGQMREPRGSDIA (SEQ ID NO: 45). The peptide corresponding to the gain of function mutant G94D is GRKKRRQRRRDRLHPVHAGPIAP<u>D</u>QMREPRGSDIA (SEQ ID NO: 46).

Evaluation of gag peptides or proteins proceeds using methods as outlined in Example 1 and as previously described. Dendritic cells or other HIV sensitive cell systems are utilized and HIV infection is initiated in the presence or absence of gag proteins, peptides or other peptide constructs (for instance gag peptides fused to targeting sequences). Dendritic cells are treated with or without the peptide(s). Dendritic cell activation is measured overtime using markers such as CD86, secretion of type-I interferon, and expression of interferon-response genes by real-time PCR or other marker expression analysis methods. In addition, the consequences of dendritic cell activation are measured directly on T cells. Namely, HLA-matched T cell clones (CD4 and CD8) are exposed to dendritic cells treated with the peptide or no peptide. T cell response can be measured by means of interferon-gamma production (by intracellular staining) and by means of proliferation (by CFSE dilution). An increase in proliferation and/or in gamma-interferon production is indicative of an increased immune response or activated cell response. Importantly, stimulation of T cell clones will require the provision of an antigen for TCR stimulation. This will be achieved by providing either the actual peptide recognized by the T cell clone, in a soluble form, or by infecting the dendritic cells with HIV-1, which will lead to presentation of HIV-1 antigens.

EXAMPLE 3

Methods and Materials

Summary: Monocytes were isolated and incubated with GM-CSF and IL-4 to induce dendritic cell differentiation. Pseudotyped viruses and virus-like particles were produced by transient transfection of 293FT cells using TransIT-293 (Minis). Infections were performed by incubating $10^5$ MDDCs in 96 well U bottom plates in the presence of 8 μg/ml polybrene. Cell surface staining of activation markers was performed 48 h after infection. shRNA vectors carrying GFP were transduced into fresh monocytes together with SIVVLP (G) and dendritic cell differentiation was induced. More than 90% of cells were routinely transduced and cells were challenged at day 4 with HDVIRESRFP(G) or other control PAMPs. Additional methods and materials are presented herein below.

Cells: GHOST(28) and 293FT (Invitrogen) cells were cultured in DMEM, 10% fetal bovine serum (FBS) (HyClone) and antibiotics. PBMC were isolated from IRB-approved buffy coats from normal donors. CD14+ cells were isolated by double positive selection with anti-human CD14 magnetic beads (Miltenyii). Purity was at least 99%. CD14+ cells were cultured in RPMI, 10% FBS, antibiotics and HEPES in the presence of recombinant human GM-CSF at 10 ng/ml and IL-4 at 50 ng/ml (eBioscience). Fresh media was added at day 3, and cells were stimulated or infected at day 4. To isolate CD11c+DC, CD14-depleted PBMC were further depleted using biotin-labeled antibodies against CD3, CD16, CD19 and CD56 and streptavidin magnetic beads (Miltenyi). The negative fraction was stained and sorted on a FACSAria (BD Biosciences) as CD3−CD14−CD16−CD19−CD20−CD56−HLA-DR+CD11c+ (for antibodies, see Table 1). Purity was at least 98%. Total CD4+ T cells were isolated using human CD4 magnetic beads (Miltenyii). Naive CD4+ T cells were further sorted as CD4+CD25−CD45RA+CD45RO−.

T cell clones: T cell clones were expanded as previously described (Morner et al., 1999). The clone DR4LI15 (LGLNKIVRMYSPTSI) (SEQ ID NO: 47) was obtained from Nina Bhardwaj and the clones B81TL9 (TPQDLNTML) (SEQ ID NO: 48) and B14DA9 (DRFYKTLRA) (SEQ ID NO: 49) were obtained from Bruce Walker.

Reagents: LPS (lipopolysaccharide) and poly(I:C) (polyriboinosinic:polyribocytidylic acid) were from Sigma and were used at 1 μg/ml and 10 μg/ml, respectively. Curdlan (CM-Curdlan) was from Wako and was used at 1 μg/ml. Cyclosporin A and FK506 were from Calbiochem. AZT (Zidovudine), RAL (Raltegravir), LPV (Lopinavir), SQV (Saquinavir), TPV (Tipranavir) were obtained through the NIH AIDS Research & Reference Reagent Program. SCY (SCYX00011867717) is similar to SCY-635 and was a generous gift from Scynexis.

Infection and stimulation: At day 4 of MDDC differentiation, cells were harvested, counted and resuspended in their own media at a concentration of one million/ml with 5 μg/ml polybrene and 100 μl were aliquoted in round bottom 96-well plates. For infection, 50 μl of media or SWVLP(G) was first added. 100 μl of media or dilutions of various HIV-1-derived viral preparations were then added. SQV, TPV, AZT and RAL were added at 10 μM. Neutralizing anti-IFNα and anti-IFNβ were added at 20 μg/ml. B18R (eBioscience) was added at 0.2 μg/ml. IL28RA-Fc (R&D Systems) was added at 1 μg/ml.

Neutralizing anti-IFNAR was added at 1 μg/ml. For shRNA-transduced DC, cells were harvested, counted and resuspended in fresh media containing GM-CSF, IL-4 and 1 μg/ml polybrene at a concentration of one million/ml. 100 μl were aliquoted in round bottom 96-well plate and 100 μl of media or virus was added.

Western blot analysis: Cells were lysed in 1% NP-40, 50 mM Tris pH 8, 120 mM NaCl, 4 mM EDTA, 50 mM NaF, 1 mM $NA_3VO_4$ and a protease inhibitor cocktail (Roche). Total lysates were resolved on SDS-PAGE, transferred to PVDF membranes and probed with primary antibodies and corresponding HRP-conjugated secondary antibodies (GE Healthcare).

Cytoplasmic and nuclear fractionation: MDDC were harvested at 24 hours after infection or treatment. $4 \times 10^6$ cells were washed once with room temperature PBS, gently pelleted and resuspended in 400 μl of cold cytoplasmic lysis buffer (CL buffer) containing 10 mM Hepes pH 7.9, 10 mM sodium potassium, 1.5 mM magnesium chloride, 1 mM sodium orthovanadate, 2 mM sodium pyrophosphate, 2 mM sodium β-glycerophosphate, 5 mM sodium fluoride, complete EDTA-free protease inhibitor cocktail (Roche) and phosphatase inhibitor cocktail (SIGMA P2850). Cells in cold CL buffer were immediately pelleted at 4° C., supernatant was discarded, 40 μl CL was added, and buffer and cells were gently resuspended by slow pipetting and soft flicking and left on ice for 15 minutes. 2.5 μl of 10% NP-40 was added and cells were lysed by gentle flicking. Nuclei were pelleted at 13,000 rpm for 5 minutes at 4° C. 40 μl of supernatant was harvested and saved as the cytoplasmic fraction, and remaining liquid was discarded. 40 μl of cold nuclear lysis buffer (NL buffer) containing 420 mM sodium chloride, 20 mM HEPES pH7.9, 1.5 mM magnesium chloride, 0.2 mM EDTA, 25% glycerol and protease and phosphatase inhibitors as in CL buffer was added. Nuclei were resuspended by vigorous flicking and incubated on ice for 15 minutes, with occasional flicking. Nuclei were vortexed for 10 seconds and sonicated for 10 minutes in a 4° C. bath sonicator (30 seconds on, 30 seconds off). The nuclear lysate was cleared by centrifugation at 13,000 rpm for 5 minutes at 4° C., and the resulting supernatant was saved as the nuclear extract. Western blot loading buffer with dithiothreitol was added to the cytoplasmic and nuclear extracts, and the samples were heated at 70° C. for 15 minutes. 10 μl of each sample were run on a 7.5% SDS-PAGE gel and transferred to PVDF membrane (Roche). Membranes were blocked with 5% non-fat dry milk in TBS containing 0.1% Tween-20 (TBST) and probed with primary antibody overnight while rocking at 4° C., washed six times for 5 minutes with TBST, probed with secondary HRP-conjugated antibody (GE Healthcare) for one hour at room temperature, washed six times for 5 minutes in TBST, and incubated with ECL reagents (Pierce Pico or Pierce Femto). Chemiluminescence signal was visualized using Kodak film.

Quantitative Bioassay for Interferons: 293FT and THP-1 were infected with HIVGFP(G) and SIVVLP(G) or transfected with polyI:C or total RNA from New Castle Disease (NDV)-infected A549 cells harvested in Trizol (Invitrogen) 8 hours after infection using lipofectamine 2000 (Invitrogen). NDV viral stock was produced by inoculating 10-day-old embryonated chicken eggs (Charles River). CD4+ T cells were expanded with 5 μg/ml Phytohemagglutinin-L (Sigma) and 10 U/ml human IL-2 for 4 days and infected with 100 HA units/ml of Sendai virus (Charles River) or infected with HIVGFP(G) and SIVVLP(G). Media was replaced after 24 hours and culture supernatants were harvested after another 24 hours. Cell culture supernatants were UV-irradiated to inactivate traces of Sendai virus. Supernatants were assayed for interferon activity using a recombinant COS-1 cell line, which carries a luciferase reporter containing multiple repeats of interferon-stimulated response element (ISRE). In brief, the reporter cells were exposed to cell culture supernatants for 8 hours to overnight, and assayed for luciferase activities, which were then translated to interferon activities by using a standard curve generated from a serial dilution of human interferon alpha 2a.

Microarray analysis: MDDC were infected with HIVGFP (G), SIVVLP(G), both or treated with LPS. Cells were harvested after 48 h and a subset was analyzed by flow cytometry. RNA was prepared with TRIZOL and microarray data generation was done using standard protocols on Human Genome U133A 2.0 arrays (Affymetrix). Microarray analysis was performed using the Bioconductor package in R and Genespring GX10 (Agilent). Probes were filtered based on at least a 2-fold change in expression and $p<0.05$. Promoter analysis was performed using PRIMA (Fonteneau et al., 2001) in EXPANDER (Shamir et al., 2005). TLR Pathway analysis was performed using SPIKE (Elkon et al., 2008).

qPCR: qPCR analysis was performed as described (Manel et al, 2008) using the standard curve method or the ΔCt method (for primer sets, see Table 2).

Plasmids: HIVGFP, which is env–vpu–vpr–vif–nef–, with GFP in place of nef, has already been described (Unutmaz et al., 1999). HIVGFP ΔRev was generated by mutating the start codon of Rev. HIVGFP PTAP- was generated by mutating PTAP to LIRL. HIVGFP D52N is a point mutation of protease. HIVGFP ΔGag was generated by inserting a stop codon after 7 amino acids of Gag. VPX-VPR fusion protein was generated by fusing SIVmac251 Vpx with HIV-1 NL4-3 Vpr using the linker ANYAAAAAAADPS (SEQ ID NO: 17) in pIRES2-EGFP (Clontech). LKO1gfp was generated by replacing the puroR open-reading frame in pLKO1puro (Moffat et al., 2006) with the EGFP coding region. shRNAs were designed as described previously (see Table 3), except that a partial mir30 sequence "CTGTGAAGCCACA-GATGGG" (SEQ ID NO: 18) was used for the loop. shRNAs were then cloned as described (Moffat et al., 2006). T54A/N57A, Q63AQ67A, G89V and the parental vector pLaiΔEnv-GFP3 are env–nef–, with GFP in place of nef, and were previously described (Yamashita et al., 2007). HDVIRES-RFP was described elsewhere (Oswald-Richter et al., 2004). HIV-2 RODS Δenv GFP was generated from a HIV-2 Δenv construct (Griffin et al., 2001) by inserting the GFP coding sequence in nef, thus disrupting nef. All plasmid DNA were prepared with Invitrogen HiPure plasmid kit. Plasmid DNA did not induce DC maturation, and viral producing cells were washed after DNA transfection.

Virus production: Viral particles were produced by transfection of 293FT cells with 3 μg DNA and 8 μl TransIT-293 (Minis Bio); for shRNA vectors, we used 0.4 μg CMV-VSVG, 1 μg pCMV-ΔR8.91 and 1.6 μg shRNA; for SIVVLP (G), 0.4 μg CMV-VSVG and 2.6 μg pSIV3+ (38); for HIVG-FP(G), 0.4 μg CMV-VSVG and 2.6 μg HIVGFP; for HIV2 ROD9 Δenv GFP(G), 0.4 μg CMV-VSVG and 2.6 μg HIV2 ROD9 Δenv GFP; for NL4-3-deltaEEGFP, 0.4 μg pCMV-VSVG and 2.6 μg pNL4-3-deltaE-EGFP (Zhang et al., 2004). HIVGFP ΔRev, HIVGFP PTAP- were produced with 0.4 μg CMV-VSVG, 0.5 μg pCMV-ΔR8.91 and 2.1 μg HIV plasmid. HIVGFP ΔGag and CA mutants were produced with 0.4 μg CMVVSVG, 1 μg pCMV-ΔR8.91 and 1.6 μg HIV plasmid. R5-GFP is NL4-3 encoding for the BAL envelope and GFP in nef (Unutmaz et al., 1999; Oswald-Richter et al., 2004). One day after transfection, media was removed, cells were washed out once, and fresh media was added. Viral supernatants were harvested one day later and filtered at 0.45 μM. In some experiments, p24 concentration was measured by p24 enzyme-linked immunosorbent assay (ELISA).

RNAi: Synthetic siRNA can be delivered in MDDC by electroporation, but this is highly and rapidly toxic and renders difficult the interpretation of dendritic cell activation, which can be altered by the presence of apoptotic or necrotic cells. In addition, we have not been able to achieve significant knock-down using synthetic siRNA with lipid-based reagents in MDDC. In fact, fluorescently-labeled siRNA appeared to be simply endocytosed with all the lipid-based reagents that were tested. We thus utilized shRNA vectors. Using this method, we routinely obtained >90% transduction efficiency, alleviating the need for cell sorting or selection. Five million freshly isolated CD14+ cells were cultured in 5 ml of media containing GM-CSF, IL-4, and 1 µg/ml polybrene. One ml of SIVVLP(G) supernatant and 2.5 ml of shRNA vector supernatant were added to cells. At days 1 and 3, 2 ml of fresh media was added. At day 4, cells were transduced at more than 96% based on GFP expression and were used for further infections and stimulation as above.

HIV-specific T cell clone stimulation: 48 h after infection of MDDC, $10^5$ rested HIV-specific T cell clones were added in the presence of GolgiStop (BD Biosciences). Where indicated, t cells were activated with 50 ng/ml PMA (Sigma) and 0.5 µg/ml ionomycin (Sigma). Cells were incubated for 6 hours and processed for intracellular staining (Manel et al., 2008).

Naive T cell proliferation assay: 48 h after infection, naive T cells were labeled with CFSE (eBioscience) as described previously (Antons et al., 2008). DC were infected with dilutions of SIVVLP(G) and pLaiΔEnv-GFP3(G) WT (indicated as HIVGFP(G)) or G89V. AZT was added at the time of infection and SCY was added from 3 to 8 hours after infection. 48 hours after infection, half of the DC was processed for surface staining and cytometry. The other half was washed with media and resuspended in fresh media without cytokines. 20,000 T cells were mixed with DC at a DC to T ratio of 1:5 and 1:15. Cells were stimulated by dilutions of anti-CD3 (OKT3 hybridoma supernatant, approximately 1-100 ng/ml) in a total volume of 150 to 200 µl in round bottom 96-well plates. Cells were harvested and analyzed by flow cytometry at day 4 or day 5 postactivation.

Trans-enhancement: $10^5$ Day 4 MDDC were infected with dilutions of HDVIRESRFP(G) and SIVVLP(G) in 96 well round bottom plates in the presence of 5 µg/ml polybrene. Type I IFN neutralizing antibodies and recombinant proteins were maintained throughout the experiment in some samples. Media was replaced after 24 hours. Another 24 hours later, half of the cells were processed for surface staining and RFP and CD86 expression were measured by flow cytometry. The other half was mixed with a preparation of replication competent R5-GFP and $5\times10^5$ CD4+ T cells at day 4 post-activation with PHA-L (Sigma) and IL-2, in the absence of polybrene. GFP expression in CD4+ T cells was measured another 48 hours later.

Results

Exposure of monocyte-derived DC (MDDC) to GFP-encoding HIV-1 pseudotyped with VSV-G (HIVGFP(G)) (MOI 1-2) resulted in little infection and absence of cell activation, as monitored by expression of CD86, CD80, CD38, and CD83 (FIG. 3). Likewise, VSV-G pseudotyped SIVmac239 virus-like particles (SIVVLP(G)) had no effect DC activation. In contrast, co-infection of MDDC with HIVGFP(G) and SIVVLP(G), which provides Vpx-mediated relief of restriction to HIV-1 replication (Goujon et al., 2006), resulted in GFP expression in more than 85% of the cells as well as up-regulation of CD86 and other activation markers after 48 h (FIG. 3). Entry of both virions into the cytoplasm was required, and activation occurred only beyond a variable threshold of infection. A virus that expressed all accessory proteins and a CCR5-tropic replication competent virus also infected MDDC in the presence of SIVVLP(G) and induced expression of CD86. Expression of a Vpx-Vpr fusion protein in packaging cells rescued the ability of HIVGFP(G) to productively infect MDDC and to induce CD86 up-regulation, indicating that Vpx is the only SIVVLP component required for infection with HIV-1. Thus, MDDC carry an intact mechanism of activation following HIV-1 infection.

As observed with MDDC, infection of primary peripheral blood CD11c+ DC with HIVGFP(G) did not result in detectable expression of GFP. However, CD11c+ DC were infected with HIVGFP(G) in the presence of SIVVLP(G), resulting in up-regulation of CD86 in a proportion of cells similar to that observed after incubation with poly(I:C).

Figure 13:
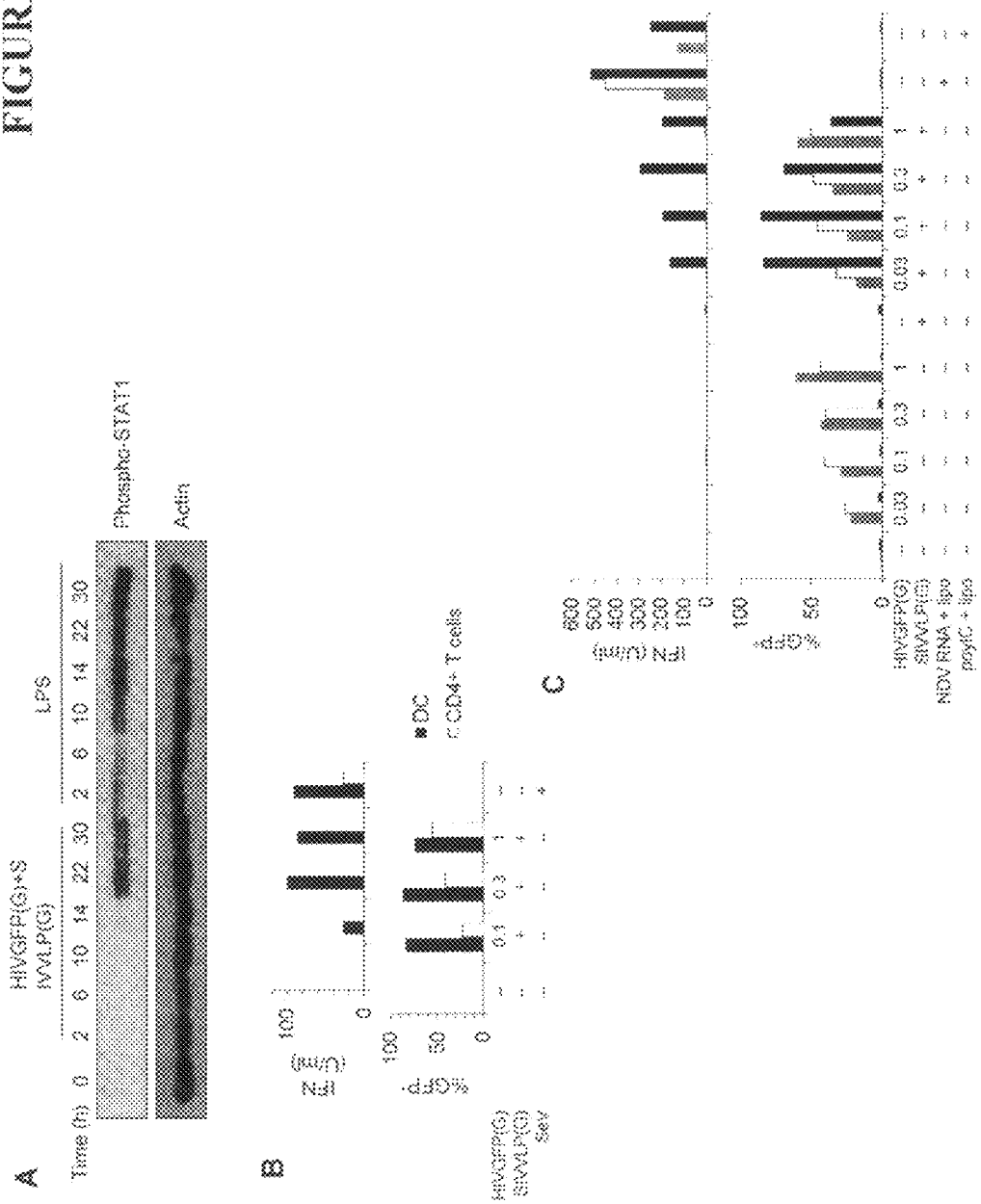
FIGS. 13A, 13B, and 13C shows that productive infection of MDDC with HIV-1 induces a type I interferon response. (A) Immunoblot of phospho-STAT1 and total actin expression over time in MDDC infected with HIVGFP(G) and SIV-VLP(G) or treated with LPS. (B) Type I interferon activity in the supernatant of MDDC or activated CD4+ T cells infected with SIVVLP(G) alone or in combination with dilutions of HIVGFP(G) or with Sendai virus (SeV). (C) Type I interferon activity in supernatants of MDDC, 293FT and THP-1 cells infected with SIVVLP(G) alone or in combination with dilutions of HIVGFP(G) or transfected with poly(I:C) or RNA from Newcastle Disease Virus (NDV)-infected cells.

Genome-wide expression profiling demonstrated induction of a type I interferon response following co-infection, but not following infection with either HIV-1 or SIV particles (FIGS. 7A and B). After infection, expression of interferon-regulated genes was delayed as compared to the response to LPS (FIG. 7B). Accordingly, STAT1 phosphorylation was present at 2 h after LPS treatment, but only at 22 h after infection (FIG. 13A). Type I interferon was produced by infected MDDC over the course of 48 hours, but was not detected following infection of CD4+ T cells (FIG. 13B), 293T cells, and THP-1 cells (FIG. 13C), despite the ability of those cells to produce type I IFN after other viral innate stimuli. Blocking antibodies against IFNβ, but not IFNα, reduced expression of the activation markers on MDDC. Further neutralization of type I and type III IFN did not improve the inhibition. Together, these results suggest that CD86 induction is mainly due to the production of soluble type I IFMβ, in accordance with observations in murine DC (Honda et al., 2003).

Next, we sought to determine which step of the viral replication cycle is required for MDDC activation. Inhibitors of HIV-1 reverse transcriptase (AZT) and integrase (Raltegravir) inhibited transduction efficiency and MDDC activation only when added during the first 24 hours and had no effect on LPS- or poly(I:C)-induced CD86 up-regulation. These results suggested that DC activation is induced after integration. There was no activation of MDDC after infection with an HIV-1-based vector devoid of viral protein-coding sequences (LKO1gfp). We therefore introduced mutations in the packaged HIVGFP genome, and evaluated activation of infected MDDC. Inactivation of Rev, required for nuclear export of unspliced viral RNA (Malim et al., 1988), and abrogation of Gag expression prevented MDDC activation (FIG. 9A), but mutation of the PTAP sequence in p6, required for viral budding (Demirov et al., 2002), and treatment with HIV-1 protease inhibitors had no effect. In the absence of SIVVLP(G), intracellular CA from incoming viral particles failed to induce CD86 expression. These results suggested that newly synthesized GagPol is required for DC activation, which is consistent with the delayed induction of the type I interferon response. We next tested a panel of viruses with CA mutations (Yamashita et al., 2007) for the ability to induce the innate response in MDDC. These mutants were defective for DC infection and were thus partially rescued by cotransfection of wild type viral proteins in the packaging cells. The T54A/N57A and Q63A/Q67A mutants induced CD86 expression despite reduced infectivity compared to wild-type virus (FIG. 9B). In contrast, infection with the G89V mutant, which is compromised for CA binding to cyclophilin A (CypA), a peptidyl-prolyl isomerase required for optimal HIV-1 infectivity (Yoo et al., 1997), resulted in substantially reduced CD86 expression at similar levels of infection.

Figure 14:
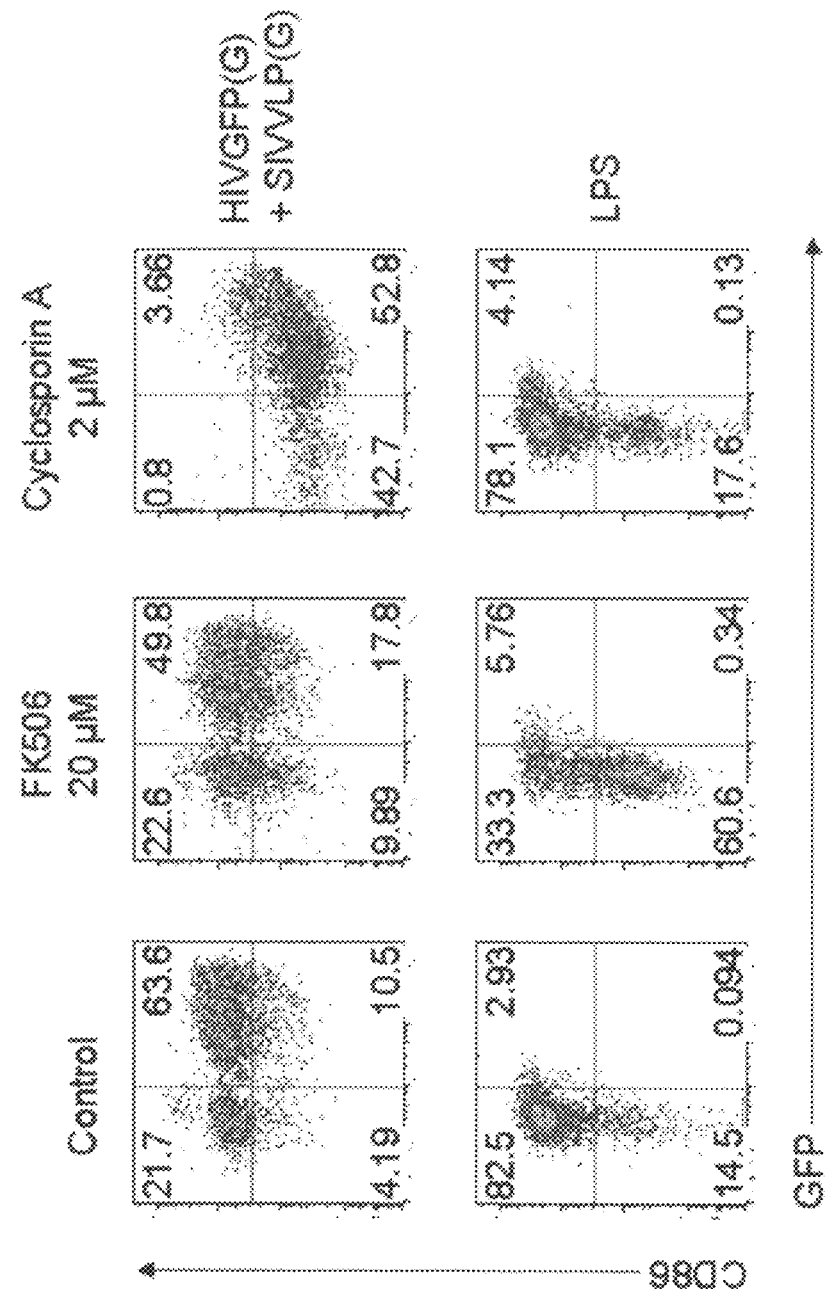
FIG. 14 depicts the effect of Cyclosporin A and FK506 on expression of CD86 in MDDC infected with HIVGFP(G) and SIVVLP(G) or after treatment with LPS. CsA and FK506 target the calcineurin pathway but FK506 does not bind to CypA.

Treatment with Cyclosporin A (CsA), which disrupts the interaction between CypA and CA (Luban et al., 1993), prevented MDDC activation following infection with HIVGFP (G) and SIVVLP(G), but not following treatment with LPS (FIG. 14). Because CsA also inhibits infection with HIV-1, we assessed its effect when administered at different times after infection of MDDC. When CsA was added as late as 12 h following infection, it prevented up-regulation of CD86 despite highly efficient infection and expression of CA.

Figure 12A:
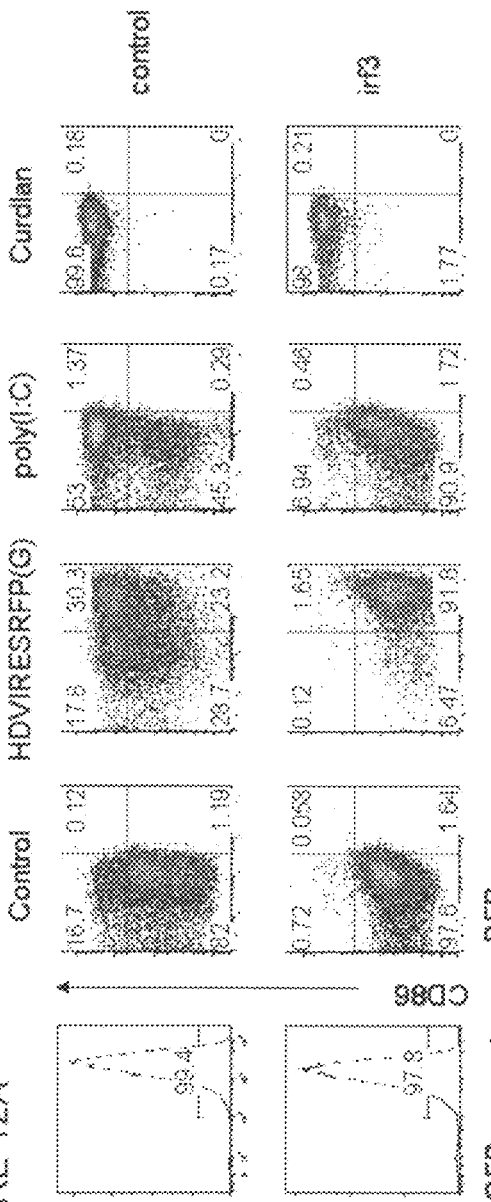
FIGS. 12A and 12B shows that dendritic cell activation by HIV-1 requires IRF-3 and cyclophilin A interaction with newly synthesized HIV-1 capsid. (A) GFP, RFP and CD86 expression in MDDC initially transduced with GFP-encoding control shRNA vector or a shRNA vector targeting IRF3 and subsequently challenged with HDVIRESRFP(G) or treated with poly(I:C) or Curdlan. Right panel: cells are gated on GFP+ transduced populations. (B) Expression of GFP, RFP and CD86 in HIV-infected cells following CypA knock-down by RNAi. MDDC were transduced with GFP-encoding control shRNA vector or a shRNA vector targeting the CypA-encoding PPIA, in the presence of SIVVLP(G), and subsequently challenged with HDVIRESRFP(G) or treated with LPS. Right panel: cells are gated on GFP+ populations shown in the left panels. Experiments were performed on a total of at least 6 donors.
Figure 12B:
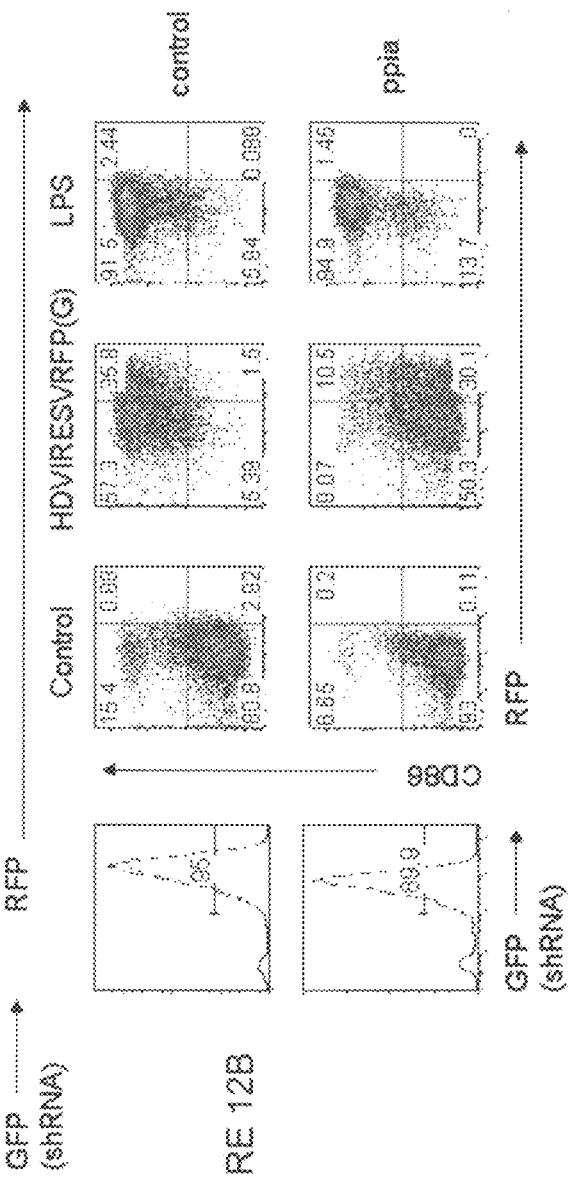

To study the role of CypA and other host genes in innate immune signaling following productive infection of MDDC with HIV-1, we employed an RNAi approach using shRNA lentiviral vectors (that also express GFP) (Boggiano et al., 2007) along with SIVVLP(G). Knockdown of PPM markedly reduced expression of its product, CypA, and prevented CD86 up-regulation following infection with HIV-1 (HD-VIRESRFP(G), encoding the reporter RFP), but not following treatment with LPS (FIG. 12B). The interaction between CypA and newly synthesized CA is therefore essential for the innate response of MDDC to HIV-1.

Figure 15:
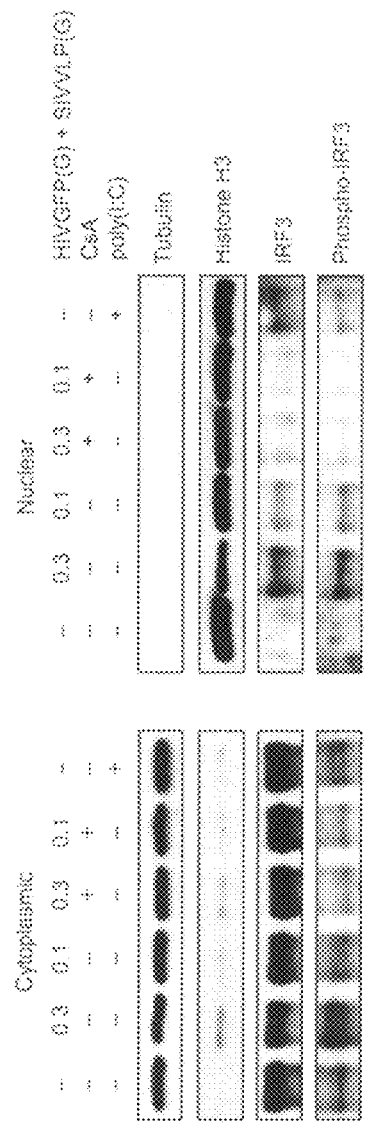
FIG. 15 demonstrates that dendritic cell activation by HIV-1 activates IRF-3. (a) Tubulin, Histone H3, IRF3 and Phosphor-Ser396-IRF3 expression in cytoplasmic and nuclear fractions of MDDC infected with SIVVLP(G) and dilutions of HIVGFP(G) in the presence or the absence of CsA. Cells were harvested at 8 hours after infection or after control treatment with poly(I:C).

Type I interferon responses following infection with multiple viruses requires the phosphorylation, dimerization, and nuclear translocation of IRF3 (Sato et al., 2000). Productive infection of MDDC with HIV-1 resulted in CsA-sensitive nuclear accumulation of phosphorylated IRF3 (FIG. 15). Knock-down of IRF3 in MDDC abrogated the induction of CD86 upon infection with HIV-1 and, as expected, following treatment with LPS or poly(I:C)), but not after treatment with curdlan, indicating that IRF3 knockdown did not lead to an intrinsic defect in CD86 expression (FIG. 12A). IRF3 knockdown, as well as CypA knockdown, also increased the threshold at which virus induced CD86 and CD38.

To determine if productive infection and subsequent activation of MDDC influences antiviral adaptive immunity, we first examined whether HIV-infected DC could activate HIV-1 Gag-specific CD4+ and CD8+ T cell clones. In the presence of MDDC incubated with HIV-1 alone, low levels of IFNγ were detected (Moris et al., 2006). In contrast, MDDC infected with HIVGFP(G) and SIVVLP(G) stimulated a high proportion of MHC class I and class II restricted T cell clones to produce IFNγ. Maturation induced by unrelated TLR ligands coupled with abortive HIV infection was not sufficient for MDDC to potently stimulate HIV antigen-specific T cells.

Figure 16A:
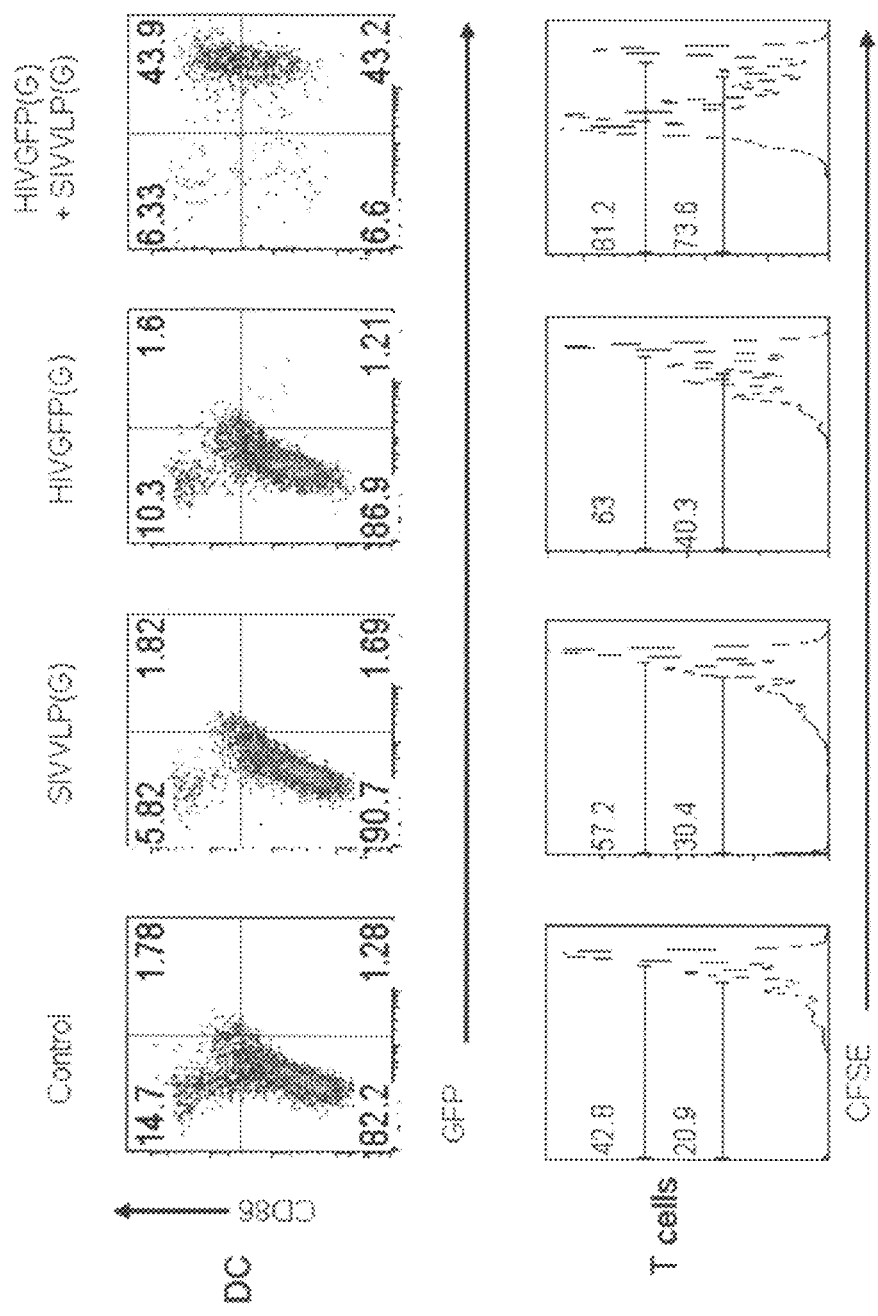

To directly measure the contribution of co-stimulation to T cell activation, we examined the polyclonal proliferation of naive CD4+ T cells in response to infected DC in the presence of sub-optimal concentrations of anti-CD3 antibody (Antons et al., 2008; Gett et al., 2003; Langenkamp et al., 2002). Under these conditions, T cells that were co-cultured with productively infected and activated MDDC proliferated through multiple cell cycles whereas T cells cultured with the abortively infected or uninfected MDDC had little proliferation (FIG. 16A). We next examined the effect of SCY, a non-immunosuppressive CsA analog (Hopkins et al., 2009; Chatterji et al., 2009) that, unlike CsA, does not have any direct effect on activation or proliferation of T cells (Hopkins et al., 2009). SCY inhibited DC activation induced by HIVGFP(G) similarly to CsA at similar levels of infection. DC treated with SCY or the RT inhibitor AZT at the time of HIVGFP(G) and SIVVLP(G) infection showed a reduced ability to induce proliferation (FIG. 16B), as did DC infected with the G89V CA mutant. These results are consistent with a requirement for interaction of newly-synthesized CA with CypA in the induction of DC costimulatory activity.

Trans-enhancement by MDDC of CD4+ T cell infection with a CCR5-tropic virus encoding GFP was inhibited if the DC were previously infected with HIV-1. The inhibition was relieved by neutralizing antibody against IFNβ, indicating that the innate response to HIV-1 in DC restricts infection of surrounding T cells (FIG. 16C) and suggesting that activation of such response may also limit infection in vivo.

Our results show that, in contrast to CD4+ T cells, human dendritic cells have intrinsic machinery for responding to infection with HIV-1 and for activating antiviral defenses and adaptive immunity. However, they are unlikely to do so effectively in infected individuals because HIV-1 fails to replicate in DCs. HIV-2, which is not pandemic (de Silva et al., 2008), encodes Vpx and has the potential to infect and activate MDDC in a CypA-dependent manner, which is consistent with the reported ability of HIV-2 CA to bind human CypA (Neagu et al., 2009; Price et al., 2009). The finding that newly synthesized CA is required to induce DC activation through a pathway involving CypA and IRF3 implicates an intracellular viral protein, in addition to viral nucleic acids, among the type I interferon-inducing pathogen-associated molecular patterns (PAMPs) (Janeway et al., 1989) and constitutes the first description of a cell-intrinsic recognition mechanism of retroviruses (Janeway et al., 1989). It will be important to determine whether the mechanism described herein contributes to control of the viral load in individuals infected with HIV-2, as well as in HIV-1-infected long-term non-progressors or "elite controllers" (Kosmrlj et al., advance online pub. 2010). A better mechanistic understanding of this DC-intrinsic signaling pathway may also inform HIV vaccine development.

The following present amino acid and nucleotide sequences for the indicated HIVGFP elements:

```
Protein sequences
>TAT
                                                        (SEQ ID NO: 2)
MEPVDPRLEPWKHPGSQPKTACTNCYCKKCCFHCQVCFMTKALGISYGRKKRRQRRRAHQNSQTHQASLSKQPTSQSR

GDPTGPKE

>REV
                                                        (SEQ ID NO: 3)
MAGRSGDSDEELIRTVRLIKLLYQSNPPPNPEGTRQARRNRRRRWRERQRQIHSISERILSTYLGRSAEPVPLQLPPL

ERLTLDCNEDCGTSGTQGVGSPQILVESPTILESGAKE

>GAG
                                                        (SEQ ID NO: 4)
MGARASVLSGGELDKWEKIRLRPGGKKQYKLKHIVWASRELERFAVNPGLLETSEGCRQILGQLQPSLQTGSEELRSL

YNTIAVLYCVHQRIDVKDTKEALDKIEEEQNKSKKKAQQAAADTGNNSQVSQNYPIVQNLQGQMVHQAISPRTLNAWV
```

-continued

KVVEEKAFSPEVIPMFSALSEGATPQDLNTMLNTVGGHQAAMQMLKETINEEAAEWDRLHPVHAGPIAPGQMREPRGS

DIAGTTSTLQEQIGWMTHNPPIPVGEIYKRWIILGLNKIVRMYSPTSILDIRQGPKEPFRDYVDRFYKTLRAEQASQE

VKNWMTETLLVQNANPDCKTILKALGPGATLEEMMTACQGVGGPGHKARVLAEAMSQVTNPATIMIQKGNFRNQRKTV

KCFNCGKEGHIAKNCRAPRKKGCWKCGKEGHQMKDCTERQANFLGKIWPSHKGRPGNFLQSRPEPTAPPEESFRFGEE

TTTPSQKQEPIDKELYPLASLRSLFGSDPSSQ

>GAGPOL
(SEQ ID NO: 5)
MGARASVLSGGELDKWEKIRLRPGGKKQYKLKHIVWASRELERFAVNPGLLETSEGCRQILGQLQPSLQTGSEELRSL

YNTIAVLYCVHQRIDVKDTKEALDKIEEEQNKSKKKAQQAAADTGNNSQVSQNYPIVQNLQGQMVHQAISPRTLNAWV

KVVEEKAFSPEVIPMFSALSEGATPQDLNTMLNTVGGHQAAMQMLKETINEEAAEWDRLHPVHAGPIAPGQMREPRGS

DIAGTTSTLQEQIGWMTHNPPIPVGEIYKRWIILGLNKIVRMYSPTSILDIRQGPKEPFRDYVDRFYKTLRAEQASQE

VKNWMTETLLVQNANPDCKTILKALGPGATLEEMMTACQGVGGPGHKARVLAEAMSQVTNPATIMIQKGNFRNQRKTV

KCFNCGKEGHIAKNCRAPRKKGCWKCGKEGHQMKDCTERQANFLREDLAFPQGKAREFSSEQTRANSPTRRELQVWGR

DNNSLSEAGADRQGTVSFSFPQITLWQRPLVTIKIGGQLKEALLDTGADDTVLEEMNLPGRWKPKMIGGIGGFIKVRQ

YDQILIEICGHKAIGTVLVGPTPVNIIGRNLLTQIGCTLNFPISPIETVPVKLKPGMDGPKVKQWPLTEEKIKALVEI

CTEMEKEGKISKIGPENPYNTPVFAIKKKDSTKWRKLVDFRELNKRTQDFWEVQLGIPHPAGLKQKKSVTVLDVGDAY

FSVPLDKDFRKYTAFTIPSINNETPGIRYQYNVLPQGWKGSPAIFQCSMTKILEPFRKQNPDIVIYQYMDDLYVGSDL

EIGQHRTKIEELRQHLLRWGFTTPDKKHQKEPPFLWMGYELHPDKWTVQPIVLPEKDSWTVNDIQKLVGKLNWASQIY

AGIKVRQLCKLLRGTKALTEVVPLTEEAELELAENREILKEPVHGVYYDPSKDLIAEIQKQGQGQWTYQIYQEPFKNL

KTGKYARMKGAHTNDVKQLTEAVQKIATESIVIWGKTPKFKLPIQKETWEAWWTEYWQATWIPEWEFVNTPPLVKLWY

QLEKEPIIGAETFYVDGAANRETKLGKAGYVTDRGRQKVVPLTDTTNQKTELQAIHLALQDSGLEVNIVTDSQYALGI

IQAQPDKSESELVSQIIEQLIKKEKVYLAWVPAHKGIGGNEQVDGLVSAGIRKVLFLDGIDKAQEEHEKYHSNWRAMA

SDFNLPPVVAKEIVASCDKCQLKGEAMHGQVDCSPGIWQLDCTHLEGKVILVAVHVASGYIEAEVIPAETGQETAYFL

LKLAGRWPVKTVHTDNGSNFTSTTVKAACWWAGIKQEFGIPYNPQSQGVIESMNKELKKIIGQVRDQAEHLKTAVQMA

VFIHNFKRKGGIGGYSAGERIVDIIATDIQTKELQKQITKIQNFRVYYRDSRDPVWKGPAKLLWKGEGAVVIQDNSDI

KVVPRRKAKIIRDYGKQMAGDDCVASRQDED

Nucleotide sequences
>TAT
(SEQ ID NO: 6)
ATGGAGCCAGTAGATCCTAGACTAGAGCCCTGGAAGCATCCAGGAAGTCAGCCTAAAACTGCTTGTACCAATTGCTAT

TGTAAAAAGTGTTGCTTTCATTGCCAAGTTTGTTTCATGACAAAAGCCTTAGGCATCTCCTATGGCAGGAAGAAGCGG

AGACAGCGACGAAGAGCTCATCAGAACAGTCAGACTCATCAAGCTTCTCTATCAAAGCAACCCACCTCCCAATCCCGA

GGGGACCCGACAGGCCCGAAGGAATAG

>REV
(SEQ ID NO: 7)
ATGGCAGGAAGAAGCGGAGACAGCGACGAAGAGCTCATCAGAACAGTCAGACTCATCAAGCTTCTCTATCAAAGCAAC

CCACCTCCCAATCCCGAGGGGACCCGACAGGCCCGAAGGAATAGAAGAAGAAGGTGGAGAGAGAGACAGAGACAGATC

CATTCGATTAGTGAACGGATCCTTAGCACTTATCTGGGACGATCTGCGGAGCCTGTGCCTCTTCAGCTACCACCGCTT

GAGAGACTTACTCTTGATTGTAACGAGGATTGTGGAACTTCTGGGACGCAGGGGTGGGAAGCCCTCAAATATTGGTG

GAATCTCCTACAATATTGGAGTCAGGAGCTAAAGAATAG

>GAG
(SEQ ID NO: 8)
ATGGGTGCGAGAGCGTCGGTATTAAGCGGGGGAGAATTAGATAAATGGGAAAAAATTCGGTTAAGGCCAGGGGGAAAG

AAACAATATAAACTAAAACATATAGTATGGGCAAGCAGGGAGCTAGAACGATTCGCAGTTAATCCTGGCCTTTTAGAG

ACATCAGAAGGCTGTAGACAAATACTGGGACAGCTACAACCATCCCTTCAGACAGGATCAGAAGAACTTAGATCATTA

```
TATAATACAATAGCAGTCCTCTATTGTGTGCATCAAAGGATAGATGTAAAAGACACCAAGGAAGCCTTAGATAAGATA

GAGGAAGAGCAAAACAAAAGTAAGAAAAAGGCACAGCAAGCAGCAGCTGACACAGGAAACAACAGCCAGGTCAGCCAA

AATTACCCTATAGTGCAGAACCTCCAGGGGCAAATGGTACATCAGGCCATATCACCTAGAACTTTAAATGCATGGGTA

AAAGTAGTAGAAGAGAAGGCTTTCAGCCCAGAAGTAATACCCATGTTTTCAGCATTATCAGAAGGAGCCACCCCACAA

GATTTAAATACCATGCTAAACACAGTGGGGGGACATCAAGCAGCCATGCAAATGTTAAAAGAGACCATCAATGAGGAA

GCTGCAGAATGGGATAGATTGCATCCAGTGCATGCAGGGCCTATTGCACCAGGCCAGATGAGAGAACCAAGGGGAAGT

GACATAGCAGGAACTACTAGTACCCTTCAGGAACAAATAGGATGGATGACACATAATCCACCTATCCCAGTAGGAGAA

ATCTATAAAAGATGGATAATCCTGGGATTAAATAAAATAGTAAGAATGTATAGCCCTACCAGCATTCTGGACATAAGA

CAAGGACCAAAGGAACCCTTTAGAGACTATGTAGACCGATTCTATAAAACTCTAAGAGCCGAGCAAGCTTCACAAGAG

GTAAAAAATTGGATGACAGAAACCTTGTTGGTCCAAAATGCGAACCCAGATTGTAAGACTATTTTAAAAGCATTGGGA

CCAGGAGCGACACTAGAAGAAATGATGACAGCATGTCAGGGAGTGGGGGGACCCGGCCATAAAGCAAGAGTTTTGGCT

GAAGCAATGAGCCAAGTAACAAATCCAGCTACCATAATGATACAGAAAGGCAATTTTAGGAACCAAAGAAAGACTGTT

AAGTGTTTCAATTGTGGCAAAGAAGGGCACATAGCCAAAAATTGCAGGGCCCCTAGGAAAAAGGGCTGTTGGAAATGT

GGAAAGGAAGGACACCCAAATGAAAGATTGTACTGAGAGACAGGCTAATTTTTTAGGGAAGATCTGGCCTTCCCACAAG

GGAAGGCCAGGGAATTTTCTTCAGAGCAGACCAGAGCCAACAGCCCCACCAGAAGAGAGCTTCAGGTTTGGGGAAGAG

ACAACAACTCCCTCTCAGAAGCAGGAGCCGATAGACAAGGAACTGTATCCTTTAGCTTCCCTCAGATCACTCTTTGGC

AGCGACCCCTCGTCACAATAA

>GAGPOL                                                                        (SEQ ID NO: 9)
ATGGGTGCGAGAGCGTCGGTATTAAGCGGGGGAGAATTAGATAAATGGGAAAAAATTCGGTTAAGGCCAGGGGGAAAG

AAACAATATAAACTAAAACATATAGTATGGGCAAGCAGGGAGCTAGAACGATTCGCAGTTAATCCTGGCCTTTTAGAG

ACATCAGAAGGCTGTAGACAAATACTGGGACAGCTACAACCATCCCTTCAGACAGGATCAGAAGAACTTAGATCATTA

TATAATACAATAGCAGTCCTCTATTGTGTGCATCAAAGGATAGATGTAAAAGACACCAAGGAAGCCTTAGATAAGATA

GAGGAAGAGCAAAACAAAAGTAAGAAAAAGGCACAGCAAGCAGCAGCTGACACAGGAAACAACAGCCAGGTCAGCCAA

AATTACCCTATAGTGCAGAACCTCCAGGGGCAAATGGTACATCAGGCCATATCACCTAGAACTTTAAATGCATGGGTA

AAAGTAGTAGAAGAGAAGGCTTTCAGCCCAGAAGTAATACCCATGTTTTCAGCATTATCAGAAGGAGCCACCCCACAA

GATTTAAATACCATGCTAAACACAGTGGGGGGACATCAAGCAGCCATGCAAATGTTAAAAGAGACCATCAATGAGGAA

GCTGCAGAATGGGATAGATTGCATCCAGTGCATGCAGGGCCTATTGCACCAGGCCAGATGAGAGAACCAAGGGGAAGT

GACATAGCAGGAACTACTAGTACCCTTCAGGAACAAATAGGATGGATGACACATAATCCACCTATCCCAGTAGGAGAA

ATCTATAAAAGATGGATAATCCTGGGATTAAATAAAATAGTAAGAATGTATAGCCCTACCAGCATTCTGGACATAAGA

CAAGGACCAAAGGAACCCTTTAGAGACTATGTAGACCGATTCTATAAAACTCTAAGAGCCGAGCAAGCTTCACAAGAG

GTAAAAAATTGGATGACAGAAACCTTGTTGGTCCAAAATGCGAACCCAGATTGTAAGACTATTTTAAAAGCATTGGGA

CCAGGAGCGACACTAGAAGAAATGATGACAGCATGTCAGGGAGTGGGGGGACCCGGCCATAAAGCAAGAGTTTTGGCT

GAAGCAATGAGCCAAGTAACAAATCCAGCTACCATAATGATACAGAAAGGCAATTTTAGGAACCAAAGAAAGACTGTT

AAGTGTTTCAATTGTGGCAAAGAAGGGCACATAGCCAAAAATTGCAGGGCCCCTAGGAAAAAGGGCTGTTGGAAATGT

GGAAAGGAAGGACACCCAAATGAAAGATTGTACTGAGAGACAGGCTAATTTTTTAGGGAAGATCTGGCCTTCCCACAA

GGGAAGGCCAGGGAATTTTCTTCAGAGCAGACCAGAGCCAACAGCCCCACCAGAAGAGAGCTTCAGGTTTGGGGAAGA

GACAACAACTCCCTCTCAGAAGCAGGAGCCGATAGACAAGGAACTGTATCCTTTAGCTTCCCTCAGATCACTCTTTGG

CAGCGACCCCTCGTCACAATAAAGATAGGGGGGCAATTAAAGGAAGCTCTATTAGATACAGGAGCAGATGATACAGTA

TTAGAAGAAATGAATTTGCCAGGAAGATGGAAACCAAAAATGATAGGGGGAATTGGAGGTTTTATCAAAGTAAGACAG

TATGATCAGATACTCATAGAAATCTGCGGACATAAAGCTATAGGTACAGTATTAGTAGGACCTACACCTGTCAACATA
```

```
ATTGGAAGAAATCTGTTGACTCAGATTGGCTGCACTTTAAATTTTCCCATTAGTCCTATTGAGACTGTACCAGTAAAA
TTAAAGCCAGGAATGGATGGCCCAAAAGTTAAACAATGGCCATTGACAGAAGAAAAAATAAAAGCATTAGTAGAAATT
TGTACAGAAATGGAAAAGGAAGGAAAAATTTCAAAAATTGGGCCTGAAAATCCATACAATACTCCAGTATTTGCCATA
AAGAAAAAAGACAGTACTAAATGGAGAAAATTAGTAGATTTCAGAGAACTTAATAAGAGAACTCAAGATTTCTGGGAA
GTTCAATTAGGAATACCACATCCTGCAGGGTTAAAACAGAAAAAATCAGTAACAGTACTGGATGTGGGCGATGCATAT
TTTTCAGTTCCCTTAGATAAAGACTTCAGGAAGTATACTGCATTTACCATACCTAGTATAAACAATGAGACACCAGGG
ATTAGATATCAGTACAATGTGCTTCCACAGGGATGGAAAGGATCACCAGCAATATTCCAGTGTAGCATGACAAAAATC
TTAGAGCCTTTTAGAAAACAAAATCCAGACATAGTCATCTATCAATACATGGATGATTTGTATGTAGGATCTGACTTA
GAAATAGGGCAGCATAGAACAAAAATAGAGGAACTGAGACAACATCTGTTGAGGTGGGGATTTACCACACCAGACAAA
AAACATCAGAAAGAACCTCCATTCCTTTGGATGGGTTATGAACTCCATCCTGATAAATGGACAGTACAGCCTATAGTG
CTGCCAGAAAAGGACAGCTGGACTGTCAATGACATACAGAAATTAGTGGGAAAATTGAATTGGGCAAGTCAGATTTAT
GCAGGGATTAAAGTAAGGCAATTATGTAAACTTCTTAGGGGAACCAAAGCACTAACAGAAGTAGTACCACTAACAGAA
GAAGCAGAGCTAGAACTGGCAGAAAACAGGGAGATTCTAAAAGAACCGGTACATGGAGTGTATTATGACCCATCAAAA
GACTTAATAGCAGAAATACAGAAGCAGGGGCAAGGCCAATGGACATATCAAATTTATCAAGAGCCATTTAAAAATCTG
AAAACAGGAAAATATGCAAGAATGAAGGGTGCCCACACTAATGATGTGAAACAATTAACAGAGGCAGTACAAAAAATA
GCCACAGAAAGCATAGTAATATGGGGAAAGACTCCTAAATTTAAATTACCCATACAAAAGGAAACATGGGAAGCATGG
TGGACAGAGTATTGGCAAGCCACCTGGATTCCTGAGTGGGAGTTTGTCAATACCCCTCCCTTAGTGAAGTTATGGTAC
CAGTTAGAGAAAGAACCCATAATAGGAGCAGAAACTTTCTATGTAGATGGGGCAGCCAATAGGGAAACTAAATTAGGA
AAAGCAGGATATGTAACTGACAGAGGAAGACAAAAAGTTGTCCCCCTAACGGACACAACAAATCAGAAGACTGAGTTA
CAAGCAATTCATCTAGCTTTGCAGGATTCGGGATTAGAAGTAAACATAGTGACAGACTCACAATATGCATTGGGAATC
ATTCAAGCACAACCAGATAAGAGTGAATCAGAGTTAGTCAGTCAAATAATAGAGCAGTTAATAAAAAAGGAAAAAGTC
TACCTGGCATGGGTACCAGCACACAAAGGAATTGGAGGAAATGAACAAGTAGATGGGTTGGTCAGTGCTGGAATCAGG
AAAGTACTATTTTTAGATGGAATAGATAAGGCCCAAGAAGAACATGAGAAATATCACAGTAATTGGAGAGCAATGGCT
AGTGATTTTAACCTACCACCTGTAGTAGCAAAAGAAATAGTAGCCAGCTGTGATAAATGTCAGCTAAAAGGGGAAGCC
ATGCATGGACAAGTAGACTGTAGCCCAGGAATATGGCAGCTAGATTGTACACATTTAGAAGGAAAAGTTATCTTGGTA
GCAGTTCATGTAGCCAGTGGATATATAGAAGCAGAAGTAATTCCAGCAGAGACAGGGCAAGAAACAGCATACTTCCTC
TTAAAATTAGCAGGAAGATGGCCAGTAAAAACAGTACATACAGACAATGGCAGCAATTTCACCAGTACTACAGTTAAG
GCCGCCTGTTGGTGGGCGGGGATCAAGCAGGAATTTGGCATTCCCTACAATCCCCAAAGTCAAGGAGTAATAGAATCT
ATGAATAAAGAATTAAAGAAAATTATAGGACAGGTAAGAGATCAGGCTGAACATCTTAAGACAGCAGTACAAATGGCA
GTATTCATCCACAATTTTAAAAGAAAAGGGGGGATTGGGGGGTACAGTGCAGGGGAAAGAATAGTAGACATAATAGCA
ACAGACATACAAACTAAAGAATTACAAAAACAAATTACAAAAATTCAAAATTTTCGGGTTTATTACAGGGACAGCAGA
GATCCAGTTTGGAAAGGACCAGCAAAGCTCCTCTGGAAAGGTGAAGGGGCAGTAGTAATACAAGATAATAGTGACATA
AAAGTAGTGCCAAGAAGAAAAGCAAAGATCATCAGGGATTATGGAAAACAGATGGCAGGTGATGATTGTGTGGCAAGT
AGACAGGATGAGGATTAA
>VPX-VPR
                                                       (SEQ ID NO: 10)
ATGTCAGATCCCAGGGAGAGAATCCCACCTGGAAACAGTGGAGAAGAGACAATAGGAGAGGCCTTCGAATGGCTAAAC
AGAACAGTAGAGGAGATAAACAGAGAGGCAGTAAACCACCTACCAAGGGAGCTGATTTTCCAGGTTTGGCAAAGGTCT
TGGGAATACTGGCATGATGAACAAGGGATGTCACAAAGCTATGTAAAATACAGATACTTGTGTTTAATGCAAAAGGCT
TTATTTATGCATTGCAAGAAAGGCTGTAGATGTCTAGGGGAAGGACACGGGCAGGAGGATGGAGACCAGGACCTCCT
CCTCCTCCCCCTCCAGGACTAGCAgcgaactatgcggcagctgccgcggcagctgatccgagcGAACAAGCCCCAGAA
GACCAAGGGCCACAGAGGGAGCCATACAATGAATGGACACTAGAGCTTTTAGAGGAACTTAAGAGTGAAGCTGTTAGA
```

-continued

```
CATTTTCCTAGGATATGGCTCCATAACTTAGGACAACATATCTATGAAACTTACGGGGATACTTGGGCAGGAGTGGAA

GCCATAATAAGAATTCTGCAACAACTGCTGTTTATCCATTTCAGAATTGGGTGTCGACATAGCAGAATAGGCGTTACT

CGACAGAGGAGAGCAAGAAATGGAGCCAGTAGATCCTAG
```

>VPX (SEQ ID NO: 11)

```
atgtcagatcccagggagagaatcccacctggaaacagtggagaagagacaataggagaggccttcgaatggctaaaca gaacagtagaggagataaacagagaggcagtaaaccacctaccaaggagctgattttccaggtttggcaaaggtcttg ggaatactggcatgatgaacaagggatgtcacaaagctatgtaaaatacagatacttgtgtttaatgcaaaaggcttta tttatgcattgcaagaaaggctgtagatgtctaggggaaggacacggggcaggaggatggagaccaggacctcctcctc ctcccccctccaggactagcataa
```

Sequence of SIVVLP(G)
SIVVLP(G) is composed of SIVVLP and VSV-G. The 2 corresponding sequences are listed below.
Location of Features in SIVVLP:

```
CMV promoter    1 . . . 501
SIVVLP_GAG    696 . . . 2213
SIVVLP_POL   1871 . . . 5038
SIVVLP_VPR   5782 . . . 6075
SIVVLP_VPX   5443 . . . 5781
SIVVLP_TAT   5933 . . . 6228 and 7093 . . . 7192
SIVVLP_REV   6159 . . . 6228 and 7093 . . . 7349
SIVVLP_VIF   4971 . . . 5615
```

>SIVVLP (SEQ ID NO: 12)

```
gcgttacataacttacggtaaatggcccgcctggctgaccgcccaacgaccccgcccattgacgtcaataatgacgt atgttcccatagtaacgccaataggactttccattgacgtcaatgggtggagtatttacggtaaactgcccacttgg cagtacatcaagtgtatcatatgccaagtacgccccctattgacgtcaatgacggtaaatggcccgcctggcattatg cccagtacatgaccttatgggactttcctacttggcagtacatctacgtattagtcatcgctattaccatggtgatgc ggttttggcagtacatcaatgggcgtggatagcggtttgactcacggggatttccaagtctccaccccattgacgtca atgggagtttgttttggcaccaaaatcaacgggactttccaaaatgtcgtaacaactccgccccattgacgcaaatgg gcggtaggcgtgtacggtgggaggtctatataagcagagctcgtttagtgaaccgtcagatcgcctggagacgccatc cacgctgttttgacctccatagaagacaccgggaccgatccagcctccggtcgaggccgcaagcttggcctccggttg caggtaagtgcaacacaaaaaagaaatagctgtcttgttatccaggaagggataataagatagagtgggagatgggcg cgagaaactccgtcttgtcaggaagaaagcagatgaattagaaaaaattaggctacgacccggcggaaagaaaaagt acatgttgaagcatgtagtatgggcagcaaatgaattagatagatttggattagcagaaagcctgttggagaacaaag aaggatgtcaaaaaatactttcggtcttagctccattagtgccaacaggctcagaaaatttaaaaagcctttataata ctgtctgcgtcatctggtgcattcacgcagaagagaaagtgaaacacactgaggaagcaaaacagatagtgcagagac acctagtggtggaaacaggaacagcagaaactatgccaaaaacaagtagaccaacagcaccatctagcggcagaggag gaaattacccagtacaacaataggtggtaactatgttcacctggcattaagcccgagaacattaaatgcctgggtaa aattgatagaggaaagaaatttggagcagaagtagtgccaggatttcaggcactgtcagaaggctgcaccccctatg acattaatcagatgttaaattgtgtgggagaccatcaagcggctatgcagattatcagagatattataaatgaggagg ctgcagattgggacttgcagcacccacaaccagctccacaacaaggacagcttagggagccgtcaggatcagatattg caggaacaactagttcagtagatgaacaaatccagtggatgtacagacaacagaacccataccagtaggcaacattt acaggagatggatccaactggggttgcaaaaatgtgtcagaatgtataacccaacaaacattctagatgtaaaacaag ggccaaaagagccatttcagagctatgtagacaggttctacaaaagcttaagagcagaacaaacagatgcagcagtaa agaattggatgactcaaacactgctgattcaaaatgctaacccagattgcaagctagtgctgaaggggctgggtgtga
```

-continued atcccaccctagaagaaatgctgacggcttgtcaaggagtaggggaccaggacagaaggctagattaatggcagaag ccctgaaagaggccctcgcaccagtgccaatcccttttgcagcagcccagaagaggggaccaagaaagccaattaagt gttggaattgtgggaaggagggacactctgcaaggcaatgcagagccccaagaagacagggatgctggaaatgtggaa aaatggaccatgttatggccaaatgcccgacagacaggcgggttttttaggccttggtccatggggaagaagcccc gcaatttccccatggctcaagtgcatcaggggctgacgccaactgctcccccagaggacccagctgtggatctgctaa agaactacatgcagttgggcaagcagcagagagaaagcagagagaagccttacaaggaggtgacagaggatttgctgc acctcaattctctcttggaggagaccagtagtcactgctcatattgaaggacagcctgtagaagtattattggatac aggggctgatgattctattgtaacaggaatagagttaggtccacattatacccaaaaatagtaggaggaatagggag ttttattaatactaaagaatacaaaaatgtaaaaatagaagttttaggcaaaaggattaaagggacaatcatgacagg ggacactccgattaacattttggtaggaatttgctaacagctctgggatgtctctaaatcttcccatagctaaggt agagcctgtaaaagtcaccttaaagccaggaaaggttggaccaaaattgaagcagtggccattatcaaaagaaaagat agttgcattaagagaaatctgtgaaaagatggaaaaggatggtcagttggaggaagctcccccgaccaatccatacaa cacccccacatttgccataaagaaaaaagataagaacaaatggagaatgctgatagattttagggaactaaataggt cactcaggactttacagaagtccaattaggaataccacaccctgcaggactagcaaaaaggaaaaggattacagtact ggatataggtgatgcatatttctccatacctctagatgaagaatttaggcagtacactgcctttacttaccatcagt aaataatgcagagccaggaaaacgatacatttataaggttctgcctcagggatggaagggtcaccagccatcttcca atacactatgagacatgtgctagaacccttcaggaaggcaaatccagatgtgaccttagtccagtatatggatgacat cttaatagctagtgacaggacagacctggaacatgacagggtagttttacagctaaaggaactcttaaatagcatagg gttctctaccccagaagagaaattccaaaaagatcccccatttcaatggatggggtacgaattgtggccgacaaaatg gaagttgcaaaagatagagttgccacaaagagagacctggacagtgaatgatatacagaagttagtaggagtattaaa ttgggcagctcaaatttatccaggtataaaaaccaaacatctctgtaggttaattagaggaaaaatgactctaacaga ggaagttcagtggactgagatggcagaagcagaatatgaggaaaataagataattctcagtcaggaacaagaaggatg ttattaccaagaaggcaagccattagaagccacggtaataaagagtcaggacaatcagtggtcttataaaattcacca agaagacaaaatactgaaagtaggaaaatttgcaaagataaagaatacataccaatggagttagactattagcaca tgtaatacagaaaataggaaaggaagcaatagtgatctggggacaggtcccaaaattccacttaccagttgagaggga tgtatgggaacagtggtggacagactattggcaggtaacctggataccggagtgggattttatctcaacgccaccact agtaagattagtcttcaatctagtgaaggaccctatagagggagaagaaacctattatacagatggatcatgtaataa acagtcaaaagaagggaaagcaggatatatcacagatagggcaaagacaaagtaaaagtgttagaacagactactaa tcaacaagcagaattagaagcatttctcatggcattgacagactcagggccaaagacaaatattatagtagattcaca atatgttatgggaataataacaggatgccctacagaatcagagagcaggctagttaaccaaataatagaagaaatgat taaaaagtcagaaatttatgtagcatgggtaccagcacacaaaggtataggaggaaaccaagaaatagaccacctagt tagtcaggggattagacaagttctcttcttggaaaagatagagccagcacaagaagaacatgataaataccatagtaa tgtaaaagaattggtattcaaatttggattacccagaatagtggccagacagatagtagacacctgtgataaatgtca tcagaaaggagaagctatacatgggcaggtaaattcagatctagggacttggcaaatggactgtacccatctagaagg aaaaatagtcatagttgcagtacatgtagctagtggattcatagaagcagaagtaattccacaagagacaggaagaca gacagcactatttctgttaaaattggcaggcagatggcctattacacatctacacacagataatggtgctaactttgc ctcgcaagaagtaaagatggttgcatggtgggcagggatagagcacacctttggggtaccatacaatccacagagtca gggagtagtggaagcaatgaatcaccacctgaaaaatcaaatagatagaatcagggaacaagcaaattcagtagaaac catagtattaatggcagttcattgcatgaattttaaaagaaggggaggaataggggatatgactccagcagaaagatt aattaacatgatcactacagaacaagaaatacaatttcaacaatcaaaaaactcaaaattttaaaaattttcgggtcta

```
ttacagagaaggcagagatcaactgtggaagggaccggtgagctattgtggaaggggaaggagcagtcatcttaaa
ggtagggacagacattaaggtagtacccagaagaaaggctaaaattatcaaagattatggaggaggaaaagaggtgga
tagcagttcccacatggaggataccggagaggctagagaggtggcatagcctcataaaatatctgaaatataaaacta
aagatctacaaaaggtttgctatgtgccccattttaaggtcggatgggcatggtggacctgcagcagagtaatcttcc
ccctacaggaaggaagccatttagaagtacaagggtattggcatttgacaccagaaagagggtggctcagtacttatg
cagtgaggataacctggtactcaaggaacttttggacagatgtaacaccagactatgcagacattttactgcatagca
cttatttcccttgctttacagcgggagaagtgagaagggccatcagggggagaacaactgctgtcttgctgcaagttcc
cgagagctcataggtaccaggtaccaagcctacagtacttagcactaaaagtagtaagcgatgtcagatcccagggag
agaatcccacctggaaacagtggagaagagacaataggagaggccttcgaatggctaaacagaacagtagaggagata
aacagagaggcagtaaaccacctaccaagggagctgattttccaggtttggcaaaggtcttgggaatactggcatgat
gaacaagggatgtcacaaagctatgtaaaatacagatacttgtgtttaatgcaaaaggctttatttatgcattgcaag
aaaggctgtagatgtctaggggaaggacacggggcaggaggatggagaccaggacctcctcctcctcccctccagga
ctagcataaatggaagaaagacctccagaaaatgaaggcccacaaagggaaccatgggatgaatgggtagtggaggtt
ctggaagaattgaaagaagaagctttaaaacattttgatcctcgcttgctaactgcacttggtaatcatatctataat
agacatggagacacccttgagggagcaggagaactcattagaatcctccaacgagcgctcttcatgcattttagaggc
ggatgcaaccactccagaatcggccaacctgggggaggaaatcctctctcaactataccgccctcttgaggcgtgcta
taacacatgctattgtaaaagtgttgctaccattgccagttttgttttcttaaaaagggattggggatatgttatga
gcagtcacgaaagagaagaagaactccgaaaaaggctaaggctaatacatcttctgcatcaaacaagtaagtatgcca
ttgcatacgttgtatccatatcataatatgtacatttatattggctcatgtccaacattaccgccatgttgacattga
ttattgactagtatcaccatgagtgcagaggtggcagaactgtatcgattggagttgggagattataaattagtagag
atcactccgattggcttggcccccacagatgtgaagaggtacactactggtggcacctcaagaaataaaagaggggtc
tttgtgctagggttcttgggttttctcgcaacggcaggttctgcaatgggcgcggcgtcgttgacgctgaccgctcag
tcccggactttattggctgggatagtgcagcaacagcaacagctgttggacgtggtcaagagacaacaagaattgttg
cgactgaccgtctggggaacaaagaacctccagactagggtcactgccatcgagaagtacttaaaggaccaggcgcag
ctaaatgcttggggatgtgcgtttagacaagtctgccacactactgtaccatggccaaatgcaagtctaacaccagac
tggaacaatgatacttggcaagagtgggagcgaaaggttgacttcttggaggaaaatataacagccctcctagaagag
gcacaaattcaacaagagaagaacatgtatgaattacaaaagttgaatagctgggatgtgtttggcaattggtttgac
cttgcttcttggataaagtatatacaatatggaatttatgtagttgtaggagtaatactgttaagaatagtgatctat
atagtacaaatgctagctaagttaaggcaggggtataggccagtgttctcttcccccacccttctatttccagtagact
catacccaacaggacccggcactgccaaccagagaaggcaaagaaggagacggtggagaaggcggtggcaacagctcc
tggccttggcagatagaatatattcatttcctgatccgccaactgatacgcctcttgacttggctattcagcaactgc
agaaccttgctatcgagagcataccagatcctccaaccaatactccagaggctctctgcgaccctacgaagggttcga
gaagtcctcaggactgaactgacctacctacaatatggggtggagctatttccatgaggcggtccaagccggctggaga
tctgcgacagaaactcttgcgggcgcgtggagagacttatgggagactcttaggagaggtggaagatggatcctcgca
atccctagagatcataatcagccataccacatttgtagaggttttacttgctttaaaaaacctcccacacctcccccct
gaacctgaaacataaaatgaatgcaattgttgttgttaacttgtttattgcagcttataatggttacaaataaa
>VSV-G_open_reading_frame
                                                                    (SEQ ID NO: 13)
atgaagtgccttttgtacttagccttttattcattggggtgaattgcaagttcaccatagttttccacacaaccaa
aaaggaaactggaaaaatgttccttctaattaccattattgcccgtcaagctcagatttaaattggcataatgactta
ataggcacagccttacaagtcaaaatgcccaagagtcacaaggctattcaagcagacggttggatgtgtcatgcttcc
aaatgggtcactacttgtgatttccgctggtatggaccgaagtatatatacacattccatccgatccttcactccatct
```

-continued

```
gtagaacaatgcaaggaaagcattgaacaaacgaaacaaggaacttggctgaatccaggcttccctcctcaaagttgt ggatatgcaactgtgacggatgccgaagcagtgattgtccaggtgactcctcaccatgtgctggttgatgaatacaca ggagaatgggttgattcacagttcatcaacggaaaatgcagcaattacatatgccccactgtccataactctacaacc tggcattctgactataaggtcaaagggctatgtgattctaacctcatttccatggacatcaccttcttctcagaggac ggagagctatcatccctgggaaggagggcacagggttcagaagtaactactttgcttatgaaactggaggcaaggcc tgcaaaatgcaatactgcaagcattggggagtcagactcccatcaggtgtctggttcgagatggctgataaggatctc tttgctgcagccagattccctgaatgcccagaagggtcaagtatctctgctccatctcagacctcagtggatgtaagt ctaattcaggacgttgagaggatcttggattattccctctgccaagaaacctggagcaaaatcagagcgggtcttcca atctctccagtggatctcagctatcttgctcctaaaaacccaggaaccggtcctgctttcaccataatcaatggtacc ctaaaatactttgagaccagatacatcagagtcgatattgctgctccaatcctctcaagaatggtcggaatgatcagt ggaactaccacagaaagggaactgtgggatgactgggcaccatatgaagacgtggaaattggacccaatggagttctg aggaccagttcaggatataagtttcctttatacatgattggacatggtatgttggactccgatcttcatcttagctca aaggctcaggtgttcgaacatcctcacattcaagacgctgcttcgcaacttcctgatgatgagagtttatttttggt gatactgggctatccaaaaatccaatcgagcttgtagaaggttggttcagtagttggaaaagctctattgcctcttt ttctttatcatagggttaatcattggactattcttggttctccgagttggtatccatctttgcattaaattaaagcac accaagaaaagacagatttatacagacatagagatgaaccgacttggaaagtga
```

HIVGFP DNA sequence (SEQ ID NO: 1)
From 5' LTR to 3' LTR
The deoxyribonucleotide positions for the indicated viral elements are identified below.

```
LTR: nucleotides 1-634 and 7383-8416
GAG: nucleotides 790-2289
POL section of GAGPOL (frameshift at AATTTTTA, last A is read twice in
GAGPOL): nucleotides 2290-5093
TAT: nucleotides 5238-5376
TAT/REV overlap: nucleotides 5377-5452 and 6355-6400
REV: nucleotides 6401-6629
GFP: nucleotides 6863-7579

>HIVGFP
tggaagggctaatttggtcccaaaaaagacaagagatccttgatctgtggatctaccacacacaaggctacttccctg attggcagaactacacaccagggccagggatcagatatccactgacctttggatggtgcttcaagttagtaccagttg aaccagagcaagtagaagaggccaaataaggagagaagaacagcttgttacaccctatgagccagcatgggatggagg acccggagggagaagtattagtgtggaagtttgacagcctcctagcatttcgtcacatggcccgagagctgcatccgg agtactacaaagactgctgacatcgagctttctacaagggactttccgctggggactttccaggaggtgtggcctgg gcgggactggggagtggcgagccctcagatgctacatataagcagctgcttttttgcctgtactgggtctctctggtta gaccagatctgagcctgggagctctctggctaactagggaacccactgcttaagcctcaataaagcttgccttgagtg ctcaaagtagtgtgtgcccgtctgttgtgtgactctggtaactagagatccctcagaccctttagtcagtgtggaaa atctctagcagtggcgcccgaacagggacttgaaagcgaaagtaaagccagaggagatctctcgacgcaggactcggc ttgctgaagcgcgcacggcaagaggcgaggggcggcgactggtgagtacgccaaaaattttgactagcggaggctaga aggagagagATGGGTGCGAGAGCGTCGGTATTAAGCGGGGGAGAATTAGATAAATGGGAAAAAATTCGGTTAAGGCCA

GGGGGAAAGAAACAATATAAACTAAAACATATAGTATGGGCAAGCAGGGAGCTAGAACGATTCGCAGTTAATCCTGGC

CTTTTAGAGACATCAGAAGGCTGTAGACAAATACTGGGACAGCTACAACCATCCCTTCAGACAGGATCAGAAGAACTT

AGATCATTATATAATACAATAGCAGTCCTCTATTGTGTGCATCAAAGGATAGATGTAAAAGACACCAAGGAAGCCTTA

GATAAGATAGAGGAAGAGCAAAACAAAAGTAAGAAAAAGGCACAGCAAGCAGCAGCTGACACAGGAAACAACAGCCAG
```

-continued

```
GTCAGCCAAAATTACCCTATAGTGCAGAACCTCCAGGGGCAAATGGTACATCAGGCCATATCACCTAGAACTTTAAAT
GCATGGGTAAAAGTAGTAGAAGAGAAGGCTTTCAGCCCAGAAGTAATACCCATGTTTTCAGCATTATCAGAAGGAGCC
ACCCCACAAGATTTAAATACCATGCTAAACACAGTGGGGGGACATCAAGCAGCCATGCAAATGTTAAAAGAGACCATC
AATGAGGAAGCTGCAGAATGGGATAGATTGCATCCAGTGCATGCAGGGCCTATTGCACCAGGCCAGATGAGAGAACCA
AGGGGAAGTGACATAGCAGGAACTACTAGTACCCTTCAGGAACAAATAGGATGGATGACACATAATCCACCTATCCCA
GTAGGAGAAATCTATAAAAGATGGATAATCCTGGGATTAAATAAAATAGTAAGAATGTATAGCCCTACCAGCATTCTG
GACATAAGACAAGGACCAAAGGAACCCTTTAGAGACTATGTAGACCGATTCTATAAAACTCTAAGAGCCGAGCAAGCT
TCACAAGAGGTAAAAAATTGGATGACAGAAACCTTGTTGGTCCAAAATGCGAACCCAGATTGTAAGACTATTTTAAAA
GCATTGGGACCAGGAGCGACACTAGAAGAAATGATGACAGCATGTCAGGGAGTGGGGGGACCCGGCCATAAAGCAAGA
GTTTTGGCTGAAGCAATGAGCCAAGTAACAAATCCAGCTACCATAATGATACAGAAAGGCAATTTTAGGAACCAAAGA
AAGACTGTTAAGTGTTTCAATTGTGGCAAAGAAGGGCACATAGCCAAAAATTGCAGGGCCCCTAGGAAAAAGGGCTGT
TGGAAATGTGGAAAGGAAGGACACCAAATGAAAGATTGTACTGAGAGACAGGCTAATTTTTTAGGGAAGATCTGGCCT
TCCCACAAGGGAAGGCCAGGGAATTTTCTTCAGAGCAGACCAGAGCCAACAGCCCCACCAGAAGAGAGCTTCAGGTTT
GGGGAAGAGACAACAACTCCCTCTCAGAAGCAGGAGCCGATAGACAAGGAACTGTATCCTTTAGCTTCCCTCAGATCA
CTCTTTGGCAGCGACCCCTCGTCACAAtaaagatagggggcaattaaaggaagctctattagatacaggagcagatg
atacagtattagaagaaatgaatttgccaggaagatggaaaccaaaaatgatagggggaattggaggttttatcaaag
taAgacagtatgatcagatactcatagaaatctgcggacataaagctataggtacagtattagtaggacctacacctg
tcaacataattggaagaaatctgttgactcagattggctgcactttaaattttcccattagtcctattgagactgtac
cagtaaaattaaagccaggaatggatggcccaaaagttaaacaatggccattgacagaagaaaaaataaaagcattag
tagaaatttgtacagaaatggaaaaggaaggaaaaatttcaaaaattgggcctgaaaatccatacaatactccagtat
ttgccataaagaaaaagacagtactaaatggagaaaattagtagatttcagagaacttaataagagaactcaagatt
tctgggaagttcaattaggaataccacatcctgcagggttaaaacagaaaaaatcagtaacagtactggatgtgggcg
atgcatatttttcagttcccttagataaagacttcaggaagtatactgcatttaccatacctagtataaacaatgaga
caccagggattagatatcagtacaatgtgcttccacagggatggaaaggatcaccagcaatattccagtgtagcatga
caaaaatcttagagccttttagaaaacaaaatccagacatagtcatctatcaatacatggatgatttgtatgtaggat
ctgacttagaaatagggcagcatagaacaaaaatagaggaactgagacaacatctgttgaggtggggatttaccacac
cagacaaaaaacatcagaaagaacctccattcctttggatgggttatgaactccatcctgataaatggacagtacagc
ctatagtgctgccagaaaaggacagctggactgtcaatgacatacagaaattagtgggaaaattgaattgggcaagtc
agatttatgcagggattaaagtaaggcaattatgtaaacttcttaggggaaccaaagcactaacagaagtagtaccac
taacagaagaagcagagctagaactggcagaaaacagggagattctaaaagaaccggtacatggagtgtattatgacc
catcaaaagacttaatagcagaaatacagaagcaggggcaaggccaatggacatatcaaatttatcaagagccattta
aaaatctgaaaacaggaaaatatgcaagaatgaagggtgcccacactaatgatgtgaaacaattaacagaggcagtac
aaaaaatagccacagaaagcatagtaatatggggaaagactcctaaatttaaattacccatacaaaaggaaacatggg
aagcatggtggacagagtattggcaagccacctggattcctgagtgggagtttgtcaatacccctcccttagtgaagt
tatggtaccagttagagaaagaacccataataggagcagaaactttctatgtagatggggcagccaatagggaaacta
aattaggaaaagcaggatatgtaactgacagaggaagacaaaaagttgtcccctaacgacacaacaaatcagaaga
ctgagttacaagcaattcatctagctttgcaggattcgggattagaagtaaacatagtgacagactcacaatatgcat
tgggaatcattcaagcacaaccagataagagtgaatcagagttagtcagtcaaataatagagcagttaataaaaaagg
aaaaagtctacctggcatgggtaccagcacacaaaggaattggaggaaatgaacaagtagatgggttggtcagtgctg
gaatcaggaaagtactatttttagatggaatagataaggcccaagaagaacatgagaaatatcacagtaattggagag
caatggctagtgattttaacctaccacctgtagtagcaaaagaaatagtagccagctgtgataaatgtcagctaaaag
```

-continued

```
gggaagccatgcatggacaagtagactgtagcccaggaatatggcagctagattgtacacatttagaaggaaaagtta
tcttggtagcagttcatgtagccagtggatatatagaagcagaagtaattccagcagagacagggcaagaaacagcat
acttcctcttaaaattagcaggaagatggccagtaaaaacagtacatacagacaatggcagcaatttcaccagtacta
cagttaaggccgcctgttggtgggcgggatcaagcaggaatttggcattccctacaatccccaaagtcaaggagtaa
tagaatctatgaataaagaattaaagaaaattataggacaggtaagagatcaggctgaacatcttaagacagcagtac
aaatggcagtattcatccacaattttaaaagaaaagggggattgggggtacagtgcagggaaagaatagtagaca
taatagcaacagacatacaaactaaagaattacaaaaacaaattacaaaaattcaaaattttcgggtttattacaggg
acagcagagatccagtttggaaaggaccagcaaagctcctctggaaaggtgaaggggcagtagtaatacaagataata
gtgacataaaagtagtgccaagaagaaaagcaaagatcatcagggattatggaaaacagatggcaggtgatgattgtg
tggcaagtagacaggatgaggattaacacatggaaaagattagtaaaacaccatatgggaTtggaagccataataaGA
ATTAATTCTGCaacaactgctgtttatccatttcagaattgggtgtcgacatagcagaataggcgttactcgacagag
gagagcaagaaatggagccagtagatcctagactagagccctggaagcatccaggaagtcagcctaaaactgcttgta
ccaattgctattgtaaaaagtgttgctttcattgccaagtttgtttcatgacaaaagccttaggcatctcctatggca
ggaagaagcggagacagcgacgaagagctcatcagaacagtcagactcatcaagcttctctatcaaagcagtaagtag
tacatgGGCGCGCCcatgtggcaggaagtaggaaaagcaatgtatgcccctcccatcagtggacaaattagatgttca
tcaaatattactgggctgctattaacaagagatggtggtaataacaacaatgggtccgagatcttcagacctggagga
ggcgatatgagggacaattggagaagtgaattatataaatataaagtagtaaaaattgaaccattaggagtagcaccc
accaaggcaaagagaagagtggtcagagagaaaaaagagcagtgggaataggagctttgttccttgggttcttggga
gcagcaggaagcactatgggcGCAGcgtcaatgacgctgacggtacaggccagacaattattgtctgatatagtgcag
cagcagaacaatttgctgagggctattgaggcgcaacagcatctgttgcaactcacagtctggggcatcaaacagctc
caggcaagaatcctggctgtggaaagatacctaaaggatcaacagctcctggggatttggggttgctctggaaaactc
atttgcaccactgctgtgccttggaatgctagttggagtaataaatctctggaacagatttggaataacatgacctgg
atggagtgggacagagaaattaacaattacacaagcttaatacactccttaattgaagaatcgcaaaaccagcaagaa
aagaatgaacaagaattattggaattagataaatgggcaagtttgtggaattggtttaacataacaaattggctgtgg
tatataaaattattcataatgatagtaggaggcttggtaggtttaagaatagttttgctgtactttctatagtgaat
agagttaggcagggatattcaccattatcgtttcagacccacctcccaatcccgaggggacccgacaggcccgaagga
atagaagaagaaggtggagagagagacagagacagatccattcgattagtgaacggatccttagcacttatctgggac
gatctgcggagcctgtgcctcttcagctaccaccgcttgagagacttactcttgattgtaacgaggattgtggaactt
ctgggacgcaggggtgggaagcccctcaaatattggtggaatctcctacaAtattggagtcaggaGctaaagaatagt
gctgttaGcttgctcaatgccacagccatagcagtagctgaggggacagatagggttatagaagtaGtacaagGagct
tGtagagctattcgccacatacctagaagaataagacagggcttggaaaggattttgctataaGATGGGTGGCGCGGC
CGCACTCAGATCTTGAGCTCAGGCTTGGATTCTGCAGTCGACGGTACCGCGGGCCCGGGATCCACCGGTCGCCACCAT
GGTGAGCAAGGGCGAGGAGCTGTTCACCGGGGTGGTGCCCATCCTGGTCGAGCTGGACGGCGACGTAAACGGCCACAA
GTTCAGCGTGTCCGGCGAGGGCGAGGGCGATGCCACCTACGGCAAGCTGACCCTGAAGTTCATCTGCACCACCGGCAA
GCTGCCCGTGCCCTGGCCCACCCTCGTGGCCACCCTGACCTACGGCGTGCAGTGCTTCAGCCGCTACCCCGACCACAT
GAAGCAGCACGACTTCTTCAAGTCCGCCATGCCCGAAGGCTACGTCCAGGAGCGCACCATCTTCTTCAAGGACGACGG
CAACTACAAGACCCGCGCCGAGGTGAAGTTCGAGGGCGACACCCTGGTGAACCGCATCGAGCTGAAGGGCATCGACTT
CAAGGAGGACGGCAACATCCTGGGGCACAAGCTGGAGTACAACTACAACAGCCACAACGTCTATATCATGGCCGACAA
GCAGAAGAACGGCATCAAGGTGAACTTCAAGATCCGCCACAACATCGAGGACGGCAGCGTGCAGCTCGCCGACCACTA
CCAGCAGAACACCCCCATCGGCGACGGCCCCGTGCTGCTGCCCGACAACCACTACCTGAGCACCCAGTCCGCCCTGAG
```

```
CAAAGACCCCAACGAGAAGCGCGATCACATGGTCCTGCTGGAGTTCGTGACCGCCGCCGGGATCACTCTCGGCATGGA

CGAGCTGTACAAGTAAAGCGGTCGCGActcgagacctagaaaaacatggagcaatcacaagtagcaatacagcagcta acaatgctgcttgtgcctggctagaagcacaagaggaggaagaggtgggttttccagtcacacctcaggtacctttaa gaccaatgacttacaaggcagctgtagatcttagccacttttaaaagaaaagggggactggaagggctaattcact cccaaagaagacaagatatccttgatctgtggatctaccacacacaaggctacttccctgattggcagaactacacac cagggccaggggtcagatatccactgacctttggatggtgctacaagctagtaccagttgagccagataaggtagaag aggccaataaaggagagaacaccagcttgttacaccctgtgagcctgcatggaatggatgaccctgagagagaagtgt tagagtggaggtttgacagccgcctagcatttcatcacgtggcccgagagctgcatccggagtacttcaagaactgct gacatcgagcttgctacaagggactttccgctggggactttccaggggaggcgtggcctgggcgggactggggagtggc gagccctcagatgctgcatataagcagctgcttttttgcctgtactgggtctctctggttagaccagatctgagcctgg gagctctctggctaactagggaacccactgcttaagcctcaataaagcttgccttgagtgcttcaagtagtgtgtgcc cgtctgttgtgtgactctggtaactagagatccctcagaccctttagtcagtgtggaaaatctctagca
```

HIVGFP RNA sequence (SEQ ID NO: 14)
From 5' LTR to 3' LTR
The ribonucleotide positions for the indicated viral elements
are identified below.

```
LTR: ribonucleotides 1-634 and 7383-8416
GAG: ribonucleotides 790-2289
POL section of GAGPOL (frameshift at AAUUUUUUA, last A is read twice in
GAGPOL): ribonucleotides 2290-5093
TAT: ribonucleotides 5238-5376
TAT/REV overlap: ribonucleotides 5377-5452 and 6355-6400
REV: ribonucleotides 6401-6629
GFP: ribonucleotides 6863-7579

>HIVGFP
uggaagggcuaauuuggucccaaaaaagacaagagauccuugaucuguggaucuaccacacacaaggcuacuucccug auuggcagaacuacacaccagggccagggaucagauauccacugaccuuuggauggugcuucaaguuaguaccaguug aaccagagcaaguagaagaggccaaauaaggagagaagaacagcuuguuacacccuaugagccagcaugggauggagg acccggagggagaaguauuaguguggaaguuugacagccuccuagcauuucgucacauggcccgagagcugcauccgg aguacuacaaagacugcugacaucgagcuuucuacaagggacuuuccgcuggggacuuuccagggaggugugggccuggg gcgggacuggggaguggcgagcccucagaugcuacauauaagcagcugcuuuuugccuguacugggucucucugguua gaccagaucugagccugggagcucucuggcuaacuagggaacccacugcuuaagccucaauaaagcuugccuugagug cucaaaguagugugugcccgucuguugugugacucugguaacuagagaucccucagacccuuuuagucagugugggaaa aucucuagcaguggcgcccgaacagggacuugaaagcgaaaguaaagccagaggagaucucucgacgcaggacucggc uugcugaagcgcgcacggcaagaggcgaggggcggcgacuggugaguacgccaaaaauuuugacuagcggaggcuaga aggagagagAUGGGUGCGAGAGCGUCGGUAUUAAGCGGGGGAGAAUUAGAUAAAUGGGAAAAAAUUCGGUUAAGGCCA

GGGGGAAAGAAACAAUAUAAACUAAAACAUAUAGUAUGGGCAAGCAGGGAGCUAGAACGAUUCGCAGUUAAUCCUGGC

CUUUUAGAGACAUCAGAAGGCUGUAGACAAAUACUGGGACAGCUACAACCAUCCCUUCAGACAGGAUCAGAAGAACUU

AGAUCAUUAUAUAAUACAAUAGCAGUCCUCUAUUGUGUGCAUCAAAGGAUAGAUGUAAAAGACACCAAGGAAGCCUUA

GAUAAGAUAGAGGAAGAGCAAAACAAAAGUAAGAAAAAGGCACAGCAAGCAGCAGCUGACACAGGAAACAACAGCCAG

GUCAGCCAAAAUUACCCUAUAGUGCAGAACCUCCAGGGGCAAAUGGUACAUCAGGCCAUAUCACCUAGAACUUUAAAU

GCAUGGGUAAAAGUAGUAGAAGAGAAGGCUUUCAGCCCAGAAGUAAUACCCAUGUUUUCAGCAUUAUCAGAAGGAGCC

ACCCCACAAGAUUUAAAUACCAUGCUAAACACAGUGGGGGGACAUCAAGCAGCCAUGCAAAUGUUAAAAGAGACCAUC

AAUGAGGAAGCUGCAGAAUGGGAUAGAUUGCAUCCAGUGCAUGCAGGGCCUAUUGCACCAGGCCAGAUGAGAGAACCA

AGGGGAAGUGACAUAGCAGGAACUACUAGUACCCUUCAGGAACAAAUAGGAUGGAUGACACAUAAUCCACCUAUCCCA
```

-continued

```
GUAGGAGAAAUCUAUAAAAGAUGGAUAAUCCUGGGAUUAAAUAAAAUAGUAAGAAUGUAUAGCCCUACCAGCAUUCUG
GACAUAAGACAAGGACCAAAGGAACCCUUUAGAGACUAUGUAGACCGAUUCUAUAAAACUCUAAGAGCCGAGCAAGCU
UCACAAGAGGUAAAAAAUUGGAUGACAGAAACCUUGUUGGUCCAAAAUGCGAACCCAGAUUGUAAGACUAUUUUAAAA
GCAUUGGGACCAGGAGCGACACUAGAAGAAAUGAUGACAGCAUGUCAGGGAGUGGGGGGACCCGGCCAUAAAGCAAGA
GUUUUGGCUGAAGCAAUGAGCCAAGUAACAAAUCCAGCUACCAUAAUGAUACAGAAAGGCAAUUUUAGGAACCAAAGA
AAGACUGUUAAGUGUUUCAAUUGUGGCAAAGAAGGGCACAUAGCCAAAAAUUGCAGGGCCCCUAGGAAAAAGGGCUGU
UGGAAAUGUGGAAAGGAAGGACACCAAAUGAAAGAUUGUACUGAGAGACAGGCUAAUUUUUUAGGGAAGAUCUGGCCU
UCCCACAAGGGAAGGCCAGGGAAUUUUCUUCAGAGCAGACCAGAGCCAACAGCCCCACCAGAAGAGAGCUUCAGGUUU
GGGGAAGAGACAACAACUCCCUCUCAGAAGCAGGAGCCGAUAGACAAGGAACUGUAUCCUUUAGCUUCCCUCAGAUCA
CUCUUUGGCAGCGACCCCUCGUCACAAuaaagauagggggcaauuaaaggaagcucuauuagauacaggagcagaug
auacaguauuagaagaaaugaauuugccaggaagauggaaaccaaaaaugauaggggaauuggaagguuuuaucaaag
uaAgacaguaugaucagauacucauagaaaucugcggacauaaagcuauaggu acaguauuaguaggaccuacaccug
ucaacauaauuggaagaaaucuguugacucagauuggcugcacuuuaaauuuucccauuaguccuauugagacuguac
caguaaaauuaaagccaggaauggauggcccaaaaguuaaacaauggccauugacagaagaaaaaauaaagcauuag
uagaaauuguacagaaauggaaaaggaaggaaaaauuucaaaaauugggccugaaaauccauacaauacuccaguau
uugccauaaagaaaaagacaguacuaaauggagaaaauuaguagauuucagagaacuuaauaagagaacucaagauu
ucugggaaguucaauuaggaauaccacauccugcagggu uaaaacagaaaaaaucaguaacaguacuggaugugggcg
augcauauuuucaguucccuuagauaaagacuucaggaaguauacugcauuuaccauaccuaguauaaacaaugaga
caccagggauuagauaucaguacaaugugcuuccacagggauggaaaggaucaccagcaauauuccaguguagcauga
caaaaaucuuagagccuuuuagaaaacaaaauccagacauagucaucuaucaauacauggaugauuuguauguaggau
cugacuuagaaauagggcagcauagaacaaaaauagaggaacugagacaacaucuguugagguggggauuuaccacac
cagacaaaaaacaucagaaagaaccuccauuccuuuggaugggguuaugaacuccauccugauaaauggacaguacagc
cuauagugcugccagaaaaggacagcuggacugucaaugacauacagaaauuagugggaaaauugaauugggcaaguc
agauuuaugcagggauuaaaguaaggcaauuaugu aaacuucuuaggggaaccaaagcacuaacagaaguaguaccac
uaacagaagaagcagagcuagaacuggcagaaaacagggagauucuaaaagaaccgguacauggaguguauuaugacc
caucaaaagacuuaauagcagaaauacagaagcaggggcaaggccaauggacauaucaaauuuaucaagagccauuua
aaaaucugaaaacaggaaaauaugcaagaaugaagggugcccacacuaaugaugugaaacaauuaacagaggcaguac
aaaaaauagccacagaaagcauaguaauauggggaaagacuccuaaauuuaaauuacccauacaaaaggaaacauggg
aagcauggugg acagaguauuggcaagccaccuggauuccugaguggga guuugucaauaccccucccuuagugaagu
uauggu accaguuagagaaagaacccauaauaggagcagaaacuuucuauguagaugggg cagccaauagggaaacua
aauuaggaaaagcaggauauguaacugacagaggaagacaaaaaguuguccccc uaacggacacaacaaaucagaaga
cugaguuacaagcaauucaucuagcuuugcaggauucgggauuagaaguaaacauagugacagacucacaauaugcau
ugggaaucauucaagcacaaccagauaagagugaaucagaguuagucagucaaauaauagagcaguuaauaaaaaagg
aaaaagucuaccuggcaugggu accagcacacaaaggaauuggaggaaaugaacaaguagaugggu uggucagugcug
gaaucaggaaaguacuauuuuuagauggaauagauaaggcccaagaagaacaugagaaauaucacaguaauuggagag
caauggcuagugauuuuaaccuaccaccuguaguagcaaaagaaauagu agccagcugugauaaaugucagcuaaaag
gggaagccaugcauggacaaguagacuguagcccaggaauauggcagcuagauuguacacauuuagaaggaaaaguua
ucuuggu agcaguucauguagccaguggauauauagaagcagaaguaauuccagcagagacagggcaagaaacagcau
acuuccucuuaaaauuagcaggaagauggccaguaaaaacaguacauacagacaauggcagcaauuucaccaguacua
caguuaaggccgccugu uggu gggcggggaucaagcaggaauuuggcauucccuacaaucccca aagucaaggaguaa
```

-continued uagaaucuaugaauaaagaauuaaagaaaauuauaggacagguaagagaucaggcugaacaucuuaagacagcaguac aaauggcaguauucauccacaauuuuaaaagaaaagggggauuggggggguacagugcagggaaagaauaguagaca uaauagcaacagacauacaaacuaaagaauuacaaaaacaaauuacaaaaauucaaaauuuucggguuuauuacaggg acagcagagauccaguuuggaaaggaccagcaaagcccucuggaaaggugaaggggcaguaguaauacaagauaaua gugacauaaaaguagugccaagaagaaaagcaaagaucaucagggauuauggaaaacagauggcaggugaugauugug uggcaaguagacaggaugaggauuaacacauggaaaagauuaguaaaacaccauaugggaUuggaagccauaauaaGA AUUAAUUCUGCaacaacugcuguuuauccauuucagaauuggguguccgacauagcagaauaggcguuacucgacagag gagagcaagaaauggagccaguagauccuagacuagagcccuggaagcauccaggaagucagccuaaaacugcuugua ccaauugcuauuguaaaaguguugcuuucauugccaaguuuguuucaugacaaaagccuuaggcaucuccuauggca ggaagaagcggagacagcgacgaagagcucaucagaacagucagacucaucaagcuucucuaucaaagcaguaaguag uacaugGGCGCGCCcaugugcaggaaguaggaaaagcaauguaugccccucccaucaguggacaaauuagauguuca ucaaauauuacugggcugcuauuaacaagagauggugguaauaacaacaauggguccgagaucuucagaccuggagga ggcgauaugagggacaauuggagaagugaauuauauaaauauaaaguaguaaaaauugaaccauuaggaguagcaccc accaaggcaaagagaagaguggugcagagagaaaaaagagcagugggaauaggagcuuuguccuugggguucuuggga gcagcaggaagcacuaugggcGCAGcgucaaugacgcugacgguacaggccagacaauuauugucugauauagugcag cagcagaacaauuugcugagggcuauugaggcgcaacagcaucuguugcaacucacagucuggggcaucaaacagcuc caggcaagaauccuggcugugggaaagauaccuaaaggaucaacagcuccuggggauuuggggguugcucuggaaaacuc auuugcaccacugcugugccuuggaaugcuaguuggaguaauaaaucucuggaacagauuuggaauaacaugaccugg auggaguggacagagaaauuaacaauuacacaagcuuaauacacuccuuaauugaagaaucgcaaaaccagcaagaa aagaaugaacaagaauuauuggaauuagauaaaugggcaaguuuguggaauugguuuaacauaacaaauuggcugugg uauauaaaauuauucauaaugauaguaggaggcuuggauagguuuaagaauaguuuuugcuguacuuucuauagugaau agaguuaggcagggauauucaccauuaucguuucagacccaccucccaauccgagggggacccgacaggcccgaagga auagaagaagaagguggagagagagacagagacagauccauucgauuagugaacggauccuuagcacuuaucugggac gaucugcggagccugugccucuucagcuaccaccgcuugagagacuuacucuugauuguaacgaggauuguggaacuu cugggacgcaggggguggggaagcccucaaauauuggguggaaucuccuacaAuauuggagucaggaGcuaaagaauagu gcuguuaGcuugcucaaugccacagccauagcaguagcugagggggacagauaggguuauagaaguaGuacaagGagcu uGuagagcuauucgccacauaccuagaagaauaagacagggcuuggaaaggauuuugcuauaaGAUGGGUGGCGCGGC

CGCACUCAGAUCUUGAGCUCAGGCUUGGAUUCUGCAGUCGACGGUACCGCGGGCCCGGGAUCCACCGGUCGCCACCAU

GGUGAGCAAGGGCGAGGAGCUGUUCACCGGGGUGGUGCCCAUCCUGGUCGAGCUGGACGGCGACGUAAACGGCCACAA

GUUCAGCGUGUCCGGCGAGGGCGAGGGCGAUGCCACCUACGGCAAGCUGACCCUGAAGUUCAUCUGCACCACCGGCAA

GCUGCCCGUGCCCUGGCCCACCCUCGUGGCCACCCUGACCUACGGCGUGCAGUGCUUCAGCCGCUACCCCGACCACAU

GAAGCAGCACGACUUCUUCAAGUCCGCCAUGCCCGAAGGCUACGUCCAGGAGCGCACCAUCUUCUUCAAGGACGACGG

CAACUACAAGACCCGCGCCGAGGUGAAGUUCGAGGGCGACACCCUGGUGAACCGCAUCGAGCUGAAGGGCAUCGACUU

CAAGGAGGACGGCAACAUCCUGGGGCACAAGCUGGAGUACAACUACAACAGCCACAACGUCUAUAUCAUGGCCGACAA

GCAGAAGAACGGCAUCAAGGUGAACUUCAAGAUCCGCCACAACAUCGAGGACGGCAGCGUGCAGCUCGCCGACCACUA

CCAGCAGAACACCCCCAUCGGCGACGGCCCCGUGCUGCUGCCCGACAACCACUACCUGAGCACCCAGUCCGCCCUGAG

CAAAGACCCCAACGAGAAGCGCGAUCACAUGGUCCUGCUGGAGUUCGUGACCGCCGCCGGGAUCACUCUCGGCAUGGA

CGAGCUGUACAAGUAAAGCGGUCGCGAcucgagaccuagaaaaacauggagcaaucacaaguagcaauacagcagcua acaaugcugcuugugccuggcuagaagcacaagaggaggaagaggugggguuuuccagucacaccucagguaccuuuaa gaccaaugacuuacaaggcagcuguagaucuuagccacuuuuuaaaagaaaaggggggacuggaagggcuaauucacu cccaaagaagacaagauauccuugaucuguggaucuaccacacacaaggcuacuucccugauuggcagaacuacacac -continued cagggccaggggucagauauccacugaccuuuggauggugcuacaagcuaguaccaguugagccagauaagguagaag aggccaauaaaggagagaacaccagcuuguuacacccugugagccugcauggaauggaugacccugagagagaagugu uagaguggagguuugacagccgccuagcauuucaucacguggcccgagagcugcauccggaguacuucaagaacugcu gacaucgagcuugcuacaagggacuuccgcuggggacuuuccagggaggcguggccugggcgggacugggagugge gagcccucagaugcugcauauaagcagcugcuuuuugccuguacugggucucucugguuagaccagaucugagccugg gagcucucuggcuaacuagggaacccacugcuuaagccucaauaaagcuugccuugagugcuucaaguagugugugcc cgucuguugugugacucugguaacuagagaucccucagacccuuuuagucagugugggaaaaucucuagca This invention may be embodied in other forms or carried out in other ways without departing from the spirit or essential characteristics thereof. The present disclosure is therefore to be considered as in all aspects illustrated and not restrictive, the scope of the invention being indicated by the appended Claims, and all changes which come within the meaning and range of equivalency are intended to be embraced therein.

Various references are cited throughout this Specification, each of which is incorporated herein by reference in its entirety.

REFERENCES

Antons et al. Suppression of HIV specific and allogeneic T cell activation by human regulatory T cells is dependent on the strength of signals. *PLoS One* 3 (8), e2952 (2008).

Baker, N. K., Colley, N. J. and Zuker, C. S. (1994) EMBO J. 13, 4886-4895.

Beignon et al. (2005). Endocytosis of HIV-1 activates plasmacytoid dendritic cells via Toll-like receptor-viral RNA interactions. J Clin Invest 115, 3265-3275.

Boasso et al. (2008). PDL-1 upregulation on monocytes and T cells by HIV via type I interferon: restricted expression of type I interferon receptor by CCR5-expressing leukocytes. Clin Immunol 129, 132-144.

Boggiano et al. (2007). Dendritic cell-mediated trans-enhancement of human immunodeficiency virus type 1 infectivity is independent of DC-SIGN. J Virol 81, 2519-2523.

Braaten, D., Franke, E. K. and Luban, J. (1996) J. Virol. 70, 4220-4227.

Braaten, D., Franke, E. K. and Luban, J. (1996) J. Virol. 70, 3551-3560.

Browne et al. (2009). Myd88 is required for an antibody response to retroviral infection. PLoS Pathogens *PLoS pathogens* 5, e1000298 (2009).

Cameron et al. (1992a). During HIV-1 infection most blood dendritic cells are not productively infected and can induce allogeneic CD4+ T cells clonal expansion. Clin Exp Immunol 88, 226-236.

Cameron et al. (1992b). Dendritic cells exposed to human immunodeficiency virus type-1 transmit a vigorous cytopathic infection to CD4+ T cells. Science 257, 383-387.

Cao et al. (2007). Innate immune functions of plasmacytoid dendritic cells. Curr Opin Immunol 19, 24-30.

Cavrois et al. (2008). The achilles heel of the trojan horse model of HIV-1 trans-infection. PLoS Pathog 4, e1000051.

Cavrois et al. (2006). Human immunodeficiency virus fusion to dendritic cells declines as cells mature. J Virol 80, 1992-1999.

Cavrois et al. (2007). In vitro derived dendritic cells trans-infect CD4 T cells primarily with surface-bound HIV-1 virions. PLoS Pathog 3, e4.

Chatterji, U. et al., The isomerase active site of cyclophilin A is critical for hepatitis C virus replication. *J Biol Chem* 284 (25), 16998-17005 (2009).

Colgan, J., Yuan, H. E. H., Franke, E. K. and Luban, J. (1996) J. Virol. 70, 4299-4310.

Colonna et al. (2004). Plasmacytoid dendritic cells in immunity. Nat Immunol 5, 1219-1226.

Cameron et al., Dendritic cells exposed to human immunodeficiency virus type-1 transmit a vigorous cytopathic infection to CD4+ T cells. *Science* (New York, N.Y 257 (5068), 383-387 (1992).

Coombes et al. (2007). A functionally specialized population of mucosal CD103+ DCs induces Foxp3+ regulatory T cells via a TGF-beta and retinoic acid-dependent mechanism. J Exp Med 204, 1757-1764.

de Silva, T. I., Cotten, M., & Rowland-Jones, S. L., HIV-2: the forgotten AIDS virus. *Trends Microbiol* 16 (12), 588-595 (2008).

Demirov et al. The late domain of human immunodeficiency virus type 1 p6 promotes virus release in a cell type-dependent manner. *Journal of virology* 76 (1), 105-117 (2002).

Duran-Troise et al. (1977). Loss of Fv-1 restriction in Balb/3T3 cells following infection with a single N tropic murine leukemia virus particle. Cell 10, 479-488.

Elkon, R., Linhart, C., Sharan, R., Shamir, R., & Shiloh, Y., Genome-wide in silico identification of transcriptional regulators controlling the cell cycle in human cells. *Genome research* 13 (5), 773-780 (2003).

Elkon et al. (2008). SPIKE—a database, visualization and analysis tool of cellular signaling pathways. BMC Bioinformatics 9, 110.

Fantuzzi et al. (2004). Human immunodeficiency virus type 1 gp120 induces abnormal maturation and functional alterations of dendritic cells: a novel mechanism for AIDS pathogenesis. J Virol 78, 9763-9772.

Fedele et al. (2004). CD38 is expressed on human mature monocyte-derived dendritic cells and is functionally involved in CD83 expression and IL-12 induction. Eur J Immunol 34, 1342-1350.

Fischer, G., Bang, H. and Mech, C. (1984) Biomed. Biochim. Acta 43, 1101-1111.

Fischer, G. and Schmid, F. X. (1990) Biochemistry 29, 2205-2212

Fischer, G. (1994) Angew. Chem. Int. Ed. Engl. 33, 1415-1436.

Fonteneau, J. F. et al., Generation of high quantities of viral and tumor-specific human CD4+ and CD8+ T-cell clones using peptide pulsed mature dendritic cells. *J Immunol Methods* 258 (1-2), 111-126 (2001).

Franke, E. K., Yuan, H. E. H. and Luban, J. (1994) Nature (London) 372, 359-362

Galat, A. and Metcalfe, S. M. (1995) Progr. Biophys. Mol. Biol. 63, 67-118.

Geijtenbeek et al. (2000). DC-SIGN, a dendritic cell-specific HIV-1-binding protein that enhances trans-infection of T cells. Cell 100, 587-597.

Gendelman, H. E. et al. A selective defect of interferon alpha production in human immunodeficiency virus-infected monocytes. *The Journal of experimental medicine* 172, 1433-1442 (1990).

Gerlach et al. (2006). Effects of type I interferons on Friend retrovirus infection. J Virol 80, 3438-3444.

Gett et al. T cell fitness determined by signal strength. *Nature immunology* 4 (4), 355-360 (2003).

Gitti, R. K., Lee, B. M., Walker, J., Summers, M. F., Yoo, S, and Sundquist, W. I. (1996) Science 273, 231-235

Goff. (1996). Operating under a Gag order: a block against incoming virus by the Fv1 gene. Cell 86, 691-693.

Goujon et al. (2008). Characterization of simian immunodeficiency virus SIVSM/human immunodeficiency virus type 2 Vpx function in human myeloid cells. J Virol 82, 12335-12345.

Goujon et al. (2003). Heterologous human immunodeficiency virus type 1 lentiviral vectors packaging a simian immunodeficiency virus-derived genome display a specific postentry transduction defect in dendritic cells. J Virol 77, 9295-9304.

Goujon et al. (2006). With a little help from a friend: increasing HIV transduction of monocyte-derived dendritic cells with virion-like particles of SIV(MAC). Gene Ther 13, 991-994.

Goujon et al. (2007). SIVSM/HIV-2 Vpx proteins promote retroviral escape from a proteasome-dependent restriction pathway present in human dendritic cells. Retrovirology 4, 2.

Granelli-Piperno et al. (2004). HIV-1-infected monocyte-derived dendritic cells do not undergo maturation but can elicit IL-10 production and T cell regulation. Proc Natl Acad Sci USA 101, 7669-7674.

Griffin, S. D., Allen, J. F., & Lever, A. M., The major human immunodeficiency virus type 2 (HIV-2) packaging signal is present on all HIV-2 RNA species: cotranslational RNA encapsidation and limitation of Gag protein confer specificity. *Journal of virology* 75 (24), 12058-12069 (2001).

Gummuluru et al. (2003). Binding of human immunodeficiency virus type 1 to immature dendritic cells can occur independently of DC-SIGN and mannose binding C-type lectin receptors via a cholesterol-dependent pathway. J Virol 77, 12865-12874.

Harman, A. N. et al. HIV-1 infected dendritic cells show two phases of gene expression changes with lysosomal enzyme activity decreased during the second phase. *Blood* (2009).

Hasenkrug et al. (1997). Immunity to retroviral infection: the Friend virus model. Proc Natl Acad Sci USA 94, 7811-7816.

Heil, F. et al. Species-specific recognition of single-stranded RNA via toll-like receptor 7 and 8. *Science* (New York, N.Y 303, 1526-1529 (2004).

Henderson, L. E., Bowers, M. A., Sowder, II, R. C., Serabyn, S. A., Johnson, D. G., Bess, Jr., J. W., Arthur, L. O., Bryant, D. K. and Fenselau, C. (1992) J. Virol. 66, 1856-1865.

Hoffmann et al. (2002). *Drosophila* innate immunity: an evolutionary perspective. Nat Immunol 3, 121-126.

Honda et al., Selective contribution of IFN-alpha/beta signaling to the maturation of dendritic cells induced by double-stranded RNA or viral infection. *Proc Natl Acad Sci USA* 100 (19), 10872-10877 (2003).

Hopkins et al. (2009) SCY-635, a novel nonimmunosuppressive analog of cyclosporine that exhibits potent inhibition of hepatitis C virus RNA replication in vitro. *Antimicrob Agents Chemother* 54 (2), 660-672.

Hornung et al. (2006). 5'-Triphosphate RNA is the ligand for RIG-I. Science 314, 994-997.

Izmailova, E. et al. HIV-1 Tat reprograms immature dendritic cells to express chemoattractants for activated T cells and macrophages. *Nature medicine* 9, 191-197 (2003).

Janeway, C. A., Jr., Approaching the asymptote? Evolution and revolution in immunology. *Cold Spring Harb Symp Quant Biol* 54 Pt 1, 1-13 (1989).

Jaensson et al. (2008). Small intestinal CD103+ dendritic cells display unique functional properties that are conserved between mice and humans. J Exp Med.

Jung et al. (2002). In vivo depletion of CD11c(+) dendritic cells abrogates priming of CD8(+) T cells by exogenous cell-associated antigens. Immunity 17, 211-220.

Kosmrlj, A. et al., Effects of thymic selection of the T-cell repertoire on HLA class[thinsp]I-associated control of HIV infection. *Nature advance online publication,* 2010.

Kwon et al. (2002). DC-SIGN-mediated internalization of HIV is required for trans-enhancement of T cell infection. Immunity 16, 135-144.

Lang, K., Schmid, F. X. and Fischer, G. (1987) Nature (London) 329, 268-270.

Langenkamp et al., T cell priming by dendritic cells: thresholds for proliferation, differentiation and death and intraclonal functional diversification. *Eur J Immunol* 32 (7), 2046-2054 (2002).

Luban, J., Bossolt, K. L., Franke, E. K., Kalpana, G. V. and Goff, S. P. (1993) Cell 73, 1067-1078.

Mahalingam et al. (2001). Functional analysis of the simian immunodeficiency virus Vpx protein: identification of packaging determinants and a novel nuclear targeting domain. J Virol 75, 362-374.

Malim et al. Immunodeficiency virus rev trans-activator modulates the expression of the viral regulatory genes. *Nature* 335 (6186), 181-183 (1988).

Manel et al. The differentiation of human T(H)-17 cells requires transforming growth factor-beta and induction of the nuclear receptor RORgammat. *Nature immunology* 9 (6), 641-649 (2008).

Mangeot et al. (2000). Development of minimal lentivirus vectors derived from simian immunodeficiency virus (SIVmac251) and their use for gene transfer into human dendritic cells. J Virol 74, 8307-8315.

Mangeot, P. E. et al. High levels of transduction of human dendritic cells with optimized SIV vectors. *Mol Ther* 5, 283-290 (2002).

Maranon et al. (2004). Dendritic cells cross-present HIV antigens from live as well as apoptotic infected CD4+ T lymphocytes. Proc Natl Acad Sci USA 101, 6092-6097.

Medzhitov. (2007). Recognition of microorganisms and activation of the immune response. Nature 449, 819-826.

Mehandru et al. (2004). Primary HIV-1 infection is associated with preferential depletion of CD4+ T lymphocytes from effector sites in the gastrointestinal tract. J Exp Med 200, 761-770.

Miyazawa et al. (2008). Host genetic factors that control immune responses to retrovirus infections. Vaccine 26, 2981-2996.

Moffat, J. et al., A lentiviral RNAi library for human and mouse genes applied to an arrayed viral high-content screen. *Cell* 124 (6), 1283-1298 (2006).

Moris et al. (2006). Dendritic cells and HIV-specific CD4+ T cells: HIV antigen presentation, T-cell activation, and viral transfer. Blood 108, 1643-1651.

Morner, A. et al., Primary human immunodeficiency virus type 2 (HIV-2) isolates, like HIV-1 isolates, frequently use CCR5 but show promiscuity in coreceptor usage. *Journal of virology* 73 (3), 2343-2349 (1999).

Morner, A. et al., Primary human immunodeficiency virus type 2 (HIV-2) isolates, like HIV-1 isolates, frequently use CCR5 but show promiscuity in coreceptor usage. *Journal of virology* 73 (3), 2343-2349 (1999).

Mucida et al. (2007). Reciprocal TH17 and regulatory T cell differentiation mediated by retinoic acid. Science 317, 256-260.

Neagu, M. R. et al., Potent inhibition of HIV-1 by TRIM5-cyclophilin fusion proteins engineered from human components. *The Journal of clinical investigation* 119 (10), 3035-3047 (2009).

Negre et al. (2000). Characterization of novel safe lentiviral vectors derived from simian immunodeficiency virus (SIVmac251) that efficiently transduce mature human dendritic cells. Gene Ther 7, 1613-1623.

Niess et al. (2005). CX3CR1-mediated dendritic cell access to the intestinal lumen and bacterial clearance. Science 307, 254-258.

Oswald-Richter, K. et al., HIV infection of naturally occurring and genetically reprogrammed human regulatory T-cells. *PLoS Biol* 2 (7), E198 (2004).

Price, A. J. et al., Active site remodeling switches HIV specificity of antiretroviral TRIMCyp. *Nat Struct Mol Biol* 16 (10), 1036-1042 (2009).

Reimer U. et al., Conformational state of a 25-mer peptide from the cyclophilin-binding loop of the HIV type 1 capsid protein. *Biochem J* 326(Pt 1):181-5 (1997).

Romani N. et al., Targeting of antigens to skin dendritic cells: possibilities to enhance vaccine efficacy. Immunol Cell Biol. 88(4):424-30 (Epub 2010).

Saito et al. (2008). Innate immunity induced by composition-dependent RIG-I recognition of hepatitis C virus RNA. Nature 454, 523-527.

Sakai et al. (2006). The Vif and Vpr accessory proteins independently cause HIV-1-induced T cell cytopathicity and cell cycle arrest. Proc Natl Acad Sci USA 103, 3369-3374.

Sato et al., Distinct and essential roles of transcription factors IRF-3 and IRF-7 in response to viruses for IFN-alpha/beta gene induction. *Immunity* 13 (4), 539-548 (2000).

Schutkowski, M., Drewello, M., Wosllner, S., Jakob, M., Reimer, U., Scherer, G., Schierhorn, A. and Fischer, G. (1996) FEBS Lett. 394, 289-294.

Shamir et al. (2005). EXPANDER—an integrative program suite for microarray data analysis. BMC Bioinformatics 6, 232.

Sharova et al. (2008). Primate lentiviral Vpx commandeers DDB1 to counteract a macrophage restriction. PLoS Pathog 4, e1000057.

Smed-Sorensen et al. (2005). Differential susceptibility to human immunodeficiency virus type 1 infection of myeloid and plasmacytoid dendritic cells. J Virol 79, 8861-8869.

Smed-Sorensen et al. (2004). HIV-1-infected dendritic cells up-regulate cell surface markers but fail to produce IL-12 p70 in response to CD40 ligand stimulation. Blood 104, 2810-2817.

Srivastava et al. (2008). Lentiviral Vpx accessory factor targets VprBP/DCAF1 substrate adaptor for cullin 4 E3 ubiquitin ligase to enable macrophage infection. PLoS Pathog 4, e1000059.

Steinman et al. (2006). Dendritic cells: translating innate to adaptive immunity. Curr Top Microbiol Immunol 311, 17-58.

Stetson et al. (2008). Trex1 prevents cell-intrinsic initiation of autoimmunity. Cell 134, 587-598.

Stetson et al. (2006). Type I interferons in host defense. Immunity 25, 373-381.

Sun et al. (2007). Small intestine lamina propria dendritic cells promote de novo generation of Foxp3 T reg cells via retinoic acid. J Exp Med 204, 1775-1785.

Szebeni, J. et al. Induction of alpha interferon by human immunodeficiency virus type 1 in human monocyte-macrophage cultures. *Journal of virology* 65, 6362-6364 (1991).

Takaoka et al. (2007). DAI (DLM-1/ZBP1) is a cytosolic DNA sensor and an activator of innate immune response. Nature 448, 501-505.

Takeda et al. (2005). Toll-like receptors in innate immunity. Int Immunol 17, 1-14.

Takeuchi et al. (2007a). Recognition of viruses by innate immunity. Immunol Rev 220, 214-224.

Takeuchi et al. (2007b). Signaling pathways activated by microorganisms. Curr Opin Cell Biol 19, 185-191.

Takeuchi et al. Innate immunity to virus infection. *Immunological reviews* 227, 75-86 (2009).

Thali, M., Bukovsky, A., Kondo, E., Rosenwirth, B., Walsh, C. T., Sodroski, J. and Gottlinger, H. G. (1994) Nature (London) 372, 363-365.

Turville et al. (2004). Immunodeficiency virus uptake, turnover, and 2-phase transfer in human dendritic cells. Blood 103, 2170-2179.

Unutmaz et al. (1999). Cytokine signals are sufficient for HIV-1 infection of resting human T lymphocytes. J Exp Med 189, 1735-1746.

Veazey et al. (2003). The mucosal immune system and HIV-1 infection. AIDS Rev 5, 245-252.

Woelk, C. H. et al. Interferon gene expression following HIV type 1 infection of monocyte-derived macrophages. *AIDS research and human retroviruses* 20, 1210-1222 (2004).

Wu et al. (2006). Dendritic-cell interactions with HIV: infection and viral dissemination. Nat Rev Immunol 6, 859-868.

Yamashita, M., Perez, O., Hope, T. J., & Emerman, M., Evidence for direct involvement of the capsid protein in HIV infection of nondividing cells. *PLoS pathogens* 3 (10), 1502-1510 (2007).

Yang et al., Engineered lentivector targeting of dendritic cells for in vivo immunization. Nature Biotechnol 26(3), 326-334 (Epub 2008).

Yoo et al., Molecular recognition in the capsid/cyclophilin A complex. *Journal of molecular biology* 269 (5), 780-795 (1997).

Yu et al. (2008). HIV traffics through a specialized, surface-accessible intracellular compartment during trans-infection of T cells by mature dendritic cells. PLoS Pathog 4, e1000134.

Zhang, H. et al., Novel single-cell-level phenotypic assay for residual drug susceptibility and reduced replication capacity of drug-resistant human immunodeficiency virus type 1. *Journal of virology* 78 (4), 1718-1729 (2004).

Zhang et al. (2008). Relief of preintegration inhibition and characterization of additional blocks for HIV replication in primary mouse T cells. PLoS ONE 3, e2035.

Zhou et al. (1996). CD14+ blood monocytes can differentiate into functionally mature CD83+ dendritic cells. Proc Natl Acad Sci USA 93, 2588-2592.

What is claimed is:

1. A method for stimulating or enhancing innate immune response to HIV-1 comprising administering in an immunogenic composition HIV-1 viral particles comprising a Vpx protein and a replication defective HIV-1 vector encoding an HIV-1 Gag polypeptide (SEQ ID NO: 4), wherein the Vpx protein is fused to a Vpr protein in a Vpx-Vpr fusion protein comprising SEQ ID NO: 51 and the Vpr protein of the Vpx-Vpr fusion protein facilitates incorporation of the Vpx-Vpr fusion protein into the HIV-1 viral particles.

2. The method of claim 1, wherein dendritic cells are targeted for cellular uptake or delivery.

3. The method of claim 1, wherein dendritic cells are infected by the HIV-1 viral particles following administration of the immunogenic composition and activated and express one of more of CD86, CD80, CD38, CD83, interferon, and a Type-I interferon response signature gene.

4. The method of claim 1, further comprising assessing adaptive immunity, wherein adaptive immunity activation is detected as an increase in at least one of HIV-specific CD4+ T cells, HIV-specific CD8+ T cells, or naive CD4+ T cells.

5. The method of claim 1, wherein trans-infection of CD4+ T cells is inhibited.

6. The method of claim 1, wherein the Vpx-Vpr fusion protein is encoded by SEQ ID NO: 10.

7. The method of claim 1, wherein the replication defective HIV-1 vector is missing at least one gene or activity essential for HIV-1 replication and/or budding.

8. The method of claim 7, wherein the replication defective HIV-1 vector is an envelope-deficient HIV-1 vector; comprises a PTAP mutant comprising a mutation that inactivates the PTAP motif in p6; or is a vif-deficient, vpr-deficient, vpu-deficient, or nef-deficient HIV-1 vector.

9. The method of claim 1, wherein the replication defective HIV-1 vector is HIVGFP (SEQ ID NO: 14).

10. The method of claim 9, wherein the replication defective HIV-1 vector is HIVGFP (SEQ ID NO: 14), excluding nucleotides 6863-7579 of SEQ ID NO: 14.

11. The method of claim 1, further comprising detecting at least one of dendritic cell activation or suppression of viral replication in T cells, wherein the dendritic cell activation or suppression of viral replication in T cells is positively correlated with stimulation or enhancement of the innate immune response to HIV.

12. The method of claim 1, wherein the immunogenic composition consists essentially of HIV-1 viral particles comprising a Vpx protein and a replication defective HIV-1 vector encoding an HIV-1 Gag polypeptide (SEQ ID NO: 4), wherein the Vpx protein is fused to a Vpr protein in a Vpx-Vpr fusion protein comprising SEQ ID NO: 51 and the Vpr protein of the Vpx-Vpr fusion protein facilitates incorporation of the Vpx-Vpr fusion protein into the HIV-1 viral particles, and a pharmaceutically acceptable carrier.

* * * * *

SEQUENCE LISTING

<160> NUMBER OF SEQ ID NOS: 51

<210> SEQ ID NO 1
<211> LENGTH: 8416
<212> TYPE: DNA
<213> ORGANISM: Artificial Sequence
<220> FEATURE:
<223> OTHER INFORMATION: Synthetic Human Immunodeficiency Virus vector

<400> SEQUENCE: 1

```
tggaagggct aatttggtcc caaaaaagac aagagatcct tgatctgtgg atctaccaca      60
cacaaggcta cttccctgat tggcagaact acacaccagg gccagggatc agatatccac     120
tgacctttgg atggtgcttc aagttagtac cagttgaacc agagcaagta gaagaggcca     180
aataaggaga gaagaacagc ttgttacacc ctatgagcca gcatgggatg gaggacccgg     240
agggagaagt attagtgtgg aagtttgaca gcctcctagc atttcgtcac atggcccgag     300
agctgcatcc ggagtactac aaagactgct gacatcgagc tttctacaag ggactttccg     360
ctggggactt tccagggagg tgtggcctgg gcgggactgg ggagtggcga gccctcagat     420
gctacatata agcagctgct ttttgcctgt actgggtctc tctggttaga ccagatctga     480
gcctgggagc tctctggcta actagggaac ccactgctta agcctcaata agcttgcct      540
tgagtgctca agtagtgtg tgcccgtctg ttgtgtgact ctggtaacta gagatccctc      600
agaccctttt agtcagtgtg gaaaatctct agcagtggcg cccgaacagg gacttgaaag     660
cgaaagtaaa gccagaggag atctctcgac gcaggactcg gcttgctgaa gcgcgcacgg     720
caagaggcga gggcggcga ctggtgagta cgccaaaaat tttgactagc ggaggctaga     780
aggagagaga tgggtgcgag agcgtcggta ttaagcgggg gagaattaga taatgggaa      840
aaaattcggt taaggccagg gggaaagaaa caatataaac taaaacatat agtatgggca     900
agcagggagc tagaacgatt cgcagttaat cctggccttt tagagacatc agaaggctgt     960
agacaaatac tgggacagct acaaccatcc cttcagacag gatcagaaga acttagatca    1020
ttatataata caatagcagt cctctattgt gtgcatcaaa ggatagatgt aaaagacacc    1080
aaggaagcct tagataagat agaggaagag caaaacaaaa gtaagaaaaa ggcacagcaa    1140
gcagcagctg acacaggaaa caacagccag gtcagccaaa attaccctat agtgcagaac    1200
ctccaggggc aaatggtaca tcaggccata tcacctagaa ctttaaatgc atgggtaaaa    1260
gtagtagaag agaaggcttt cagcccagaa gtaataccca tgttttcagc attatcagaa    1320
ggagccaccc cacaagattt aaataccatg ctaaacacag tggggggaca tcaagcagcc    1380
atgcaaatgt taaaagagac catcaatgag gaagctgcag aatgggatag attgcatcca    1440
gtgcatgcag ggcctattgc accaggccag atgagagaac caaggggaag tgacatagca    1500
ggaactacta gtacccttca ggaacaaata ggatggatga cacataatcc acctatccca    1560
gtaggagaaa tctataaaag atggataatc ctgggattaa ataaaatagt aagaatgtat    1620
agccctacca gcattctgga cataagacaa ggaccaaagg aaccctttag agactatgta    1680
gaccgattct ataaaactct aagagccgag caagcttcac aagaggtaaa aaattggatg    1740
acagaaacct tgttggtcca aaatgcgaac ccagattgta agactatttt aaaagcattg    1800
ggaccaggag cgacactaga agaaatgatg acagcatgtc agggagtggg gggacccggc    1860
cataaagcaa gagttttggc tgaagcaatg agccaagtaa caaatccagc taccataatg    1920
atacagaaag gcaattttag gaaccaaaga aagactgtta gtgtttcaa ttgtggcaaa     1980
gaagggcaca tagccaaaaa ttgcagggcc cctaggaaaa agggctgttg gaaatgtgga    2040
```

```
aaggaaggac accaaatgaa agattgtact gagagacagg ctaattttt agggaagatc    2100 tggccttccc acaagggaag gccagggaat tttcttcaga gcagaccaga gccaacagcc    2160
ccaccagaag agagcttcag gtttggggaa gagacaacaa ctccctctca gaagcaggag    2220
ccgatagaca aggaactgta tcctttagct tccctcagat cactctttgg cagcgacccc    2280
tcgtcacaat aaagataggg gggcaattaa aggaagctct attagataca ggagcagatg    2340
atacagtatt agaagaaatg aatttgccag gaagatggaa accaaaaatg ataggggaa    2400 ttggaggttt tatcaaagta agacagtatg atcagatact catagaaatc tgcggacata    2460
aagctatagg tacagtatta gtaggaccta cacctgtcaa cataattgga agaaatctgt    2520
tgactcagat tggctgcact ttaaattttc ccattagtcc tattgagact gtaccagtaa    2580
aattaaagcc aggaatggat ggcccaaaag ttaaacaatg gccattgaca gaagaaaaaa    2640
taaaagcatt agtagaaatt tgtacagaaa tggaaaagga aggaaaaatt tcaaaaattg    2700
ggcctgaaaa tccatacaat actccagtat ttgccataaa gaaaaagac agtactaaat    2760 ggagaaaatt agtagatttc agagaactta ataagagaac tcaagatttc tgggaagttc    2820
aattaggaat accacatcct gcagggttaa aacagaaaaa atcagtaaca gtactggatg    2880
tgggcgatgc atattttca gttcccttag ataaagactt caggaagtat actgcattta    2940
ccatacctag tataaacaat gagacaccag ggattagata tcagtacaat gtgcttccac    3000
agggatggaa aggatcacca gcaatattcc agtgtagcat gacaaaaatc ttagagcctt    3060
ttagaaaaca aaatccagac atagtcatct atcaatacat ggatgatttg tatgtaggat    3120
ctgacttaga aatagggcag catagaacaa aaatagagga actgagacaa catctgttga    3180
ggtggggatt taccacacca gacaaaaaac atcagaaaga acctccattc ctttggatgg    3240
gttatgaact ccatcctgat aaatggacag tacagcctat agtgctgcca gaaaaggaca    3300
gctggactgt caatgacata cagaaattag tgggaaaatt gaattgggca agtcagattt    3360
atgcagggat taaagtaagg caattatgta aacttcttag gggaaccaaa gcactaacag    3420
aagtagtacc actaacagaa gaagcagagc tagaactggc agaaaacagg gagattctaa    3480
aagaaccggt acatggagtg tattatgacc catcaaaaga cttaatagca gaaatacaga    3540
agcaggggca aggccaatgg acatatcaaa tttatcaaga gccatttaaa aatctgaaaa    3600
caggaaaata tgcaagaatg aagggtgccc acactaatga tgtgaaacaa ttaacagagg    3660
cagtacaaaa aatagccaca gaaagcatag taatatgggg aaagactcct aaatttaaat    3720
tacccataca aaaggaaaca tgggaagcat ggtggacaga gtattggcaa gccacctgga    3780
ttcctgagtg ggagtttgtc aatacccctc ccttagtgaa gttatggtac cagttagaga    3840
aagaacccat aataggagca gaaactttct atgtagatgg ggcagccaat agggaaacta    3900
aattaggaaa agcaggatat gtaactgaca gaggaagaca aaaagttgtc ccctaacgg    3960 acacaacaaa tcagaagact gagttacaag caattcatct agctttgcag gattcgggat    4020
tagaagtaaa catagtgaca gactcacaat atgcattggg aatcattcaa gcacaaccag    4080
ataagagtga atcagagtta gtcagtcaaa taatagagca gttaataaaa aaggaaaaag    4140
tctacctggc atgggtacca gcacacaaag gaattggagg aaatgaacaa gtagatgggt    4200
tggtcagtgc tggaatcagg aaagtactat ttttagatgg aatagataag gcccaagaag    4260
aacatgagaa atatcacagt aattggagag caatggctag tgatttaac ctaccacctg    4320 tagtagcaaa agaaatagta gccagctgtg ataaatgtca gctaaaggg gaagccatgc    4380
```

```
atggacaagt agactgtagc ccaggaatat ggcagctaga ttgtacacat ttagaaggaa   4440
aagttatctt ggtagcagtt catgtagcca gtggatatat agaagcagaa gtaattccag   4500
cagagacagg gcaagaaaca gcatacttcc tcttaaaatt agcaggaaga tggccagtaa   4560
aaacagtaca tacagacaat ggcagcaatt tcaccagtac tacagttaag gccgcctgtt   4620
ggtgggcggg gatcaagcag gaatttggca ttccctacaa tccccaaagt caaggagtaa   4680
tagaatctat gaataaagaa ttaaagaaaa ttataggaca ggtaagagat caggctgaac   4740
atcttaagac agcagtacaa atggcagtat tcatccacaa ttttaaaaga aaggggggga   4800
ttggggggta cagtgcaggg gaaagaatag tagacataat agcaacagac atacaaacta   4860
aagaattaca aaaacaaatt acaaaaattc aaaattttcg ggtttattac agggacagca   4920
gagatccagt ttggaaagga ccagcaaagc tcctctggaa aggtgaaggg gcagtagtaa   4980
tacaagataa tagtgacata aaagtagtgc caagaagaaa agcaaagatc atcagggatt   5040
atggaaaaca gatggcaggt gatgattgtg tggcaagtag acaggatgag gattaacaca   5100
tggaaaagat tagtaaaaca ccatatggga ttggaagcca ataagaat taattctgca   5160 acaactgctg tttatccatt tcagaattgg gtgtcgacat agcagaatag gcgttactcg   5220
acagaggaga gcaagaaatg gagccagtag atcctagact agagccctgg aagcatccag   5280
gaagtcagcc taaaactgct tgtaccaatt gctattgtaa aaagtgttgc tttcattgcc   5340
aagtttgttt catgacaaaa gccttaggca tctcctatgg caggaagaag cggagacagc   5400
gacgaagagc tcatcagaac agtcagactc atcaagcttc tctatcaaag cagtaagtag   5460
tacatgggcg cgcccatgtg gcaggaagta ggaaaagcaa tgtatgcccc tcccatcagt   5520
ggacaaatta gatgttcatc aaatattact gggctgctat taacaagaga tggtggtaat   5580
aacaacaatg ggtccgagat cttcagacct ggaggaggcg atatgaggga caattggaga   5640
agtgaattat ataaatataa agtagtaaaa attgaaccat taggagtagc acccaccaag   5700
gcaaagagaa gagtggtgca gagagaaaaa agagcagtgg gaataggagc tttgttcctt   5760
gggttcttgg gagcagcagg aagcactatg ggcgcagcgt caatgacgct gacggtacag   5820
gccagacaat tattgtctga tatagtgcag cagcagaaca atttgctgag ggctattgag   5880
gcgcaacagc atctgttgca actcacagtc tggggcatca aacagctcca ggcaagaatc   5940
ctggctgtgg aaagatacct aaaggatcaa cagctcctgg ggatttgggg ttgctctgga   6000
aaactcattt gcaccactgc tgtgccttgg aatgctagtt ggagtaataa atctctggaa   6060
cagatttgga ataacatgac ctggatggag tgggacagag aaattaacaa ttacacaagc   6120
ttaatacact ccttaattga agaatcgcaa aaccagcaag aaaagaatga acaagaatta   6180
ttggaattag ataaatgggc aagtttgtgg aattggttta acataacaaa ttggctgtgg   6240
tatataaaat tattcataat gatagtagga ggcttggtag gtttaagaat agttttgct   6300 gtactttcta tagtgaatag agttaggcag ggatattcac cattatcgtt tcagacccac   6360
ctcccaatcc cgaggggacc cgacaggccc gaaggaatag aagaagaagg tggagagaga   6420
gacagagaca gatccattcg attagtgaac ggatccttag cacttatctg gacgatctg   6480 cggagcctgt gcctcttcag ctaccaccgc ttgagagact tactcttgat tgtaacgagg   6540
attgtggaac ttctgggacg cagggggtgg gaagccctca atattggtg gaatctccta   6600 caatattgga gtcaggagct aaagaatagt gctgttagct tgctcaatgc cacagccata   6660
gcagtagctg aggggacaga tagggttata gaagtagtac aaggagcttg tagagctatt   6720
cgccacatac ctagaagaat aagacagggc ttggaaagga ttttgctata agatgggtgg   6780
```

-continued

```
cgcggccgca ctcagatctt gagctcaggc ttggattctg cagtcgacgg taccgcgggc     6840
ccgggatcca ccggtcgcca ccatggtgag caagggcgag gagctgttca ccggggtggt     6900
gcccatcctg gtcgagctgg acggcgacgt aaacggccac aagttcagcg tgtccggcga     6960
gggcgagggc gatgccacct acggcaagct gaccctgaag ttcatctgca ccaccggcaa     7020
gctgcccgtg ccctggccca ccctcgtggc caccctgacc tacggcgtgc agtgcttcag     7080
ccgctacccc gaccacatga agcagcacga cttcttcaag tccgccatgc ccgaaggcta     7140
cgtccaggag cgcaccatct tcttcaagga cgacggcaac tacaagaccc gcgccgaggt     7200
gaagttcgag ggcgacaccc tggtgaaccg catcgagctg aagggcatcg acttcaagga     7260
ggacggcaac atcctggggc acaagctgga gtacaactac aacagccaca acgtctatat     7320
catggccgac aagcagaaga acggcatcaa ggtgaacttc aagatccgcc acaacatcga     7380
ggacggcagc gtgcagctcg ccgaccacta ccagcagaac ccccatcg gcgacggccc     7440
cgtgctgctg cccgacaacc actacctgag cacccagtcc gccctgagca agaccccaa     7500
cgagaagcgc gatcacatgg tcctgctgga gttcgtgacc gccgccggga tcactctcgg     7560
catggacgag ctgtacaagt aaagcggtcg cgactcgaga cctagaaaaa catggagcaa     7620
tcacaagtag caatacagca gctaacaatg ctgcttgtgc ctggctagaa gcacaagagg     7680
aggaagaggt gggttttcca gtcacacctc aggtaccttt aagaccaatg acttacaagg     7740
cagctgtaga tcttagccac ttttttaaaag aaaagggggg actggaaggg ctaattcact     7800
cccaaagaag acaagatatc cttgatctgt ggatctacca cacacaaggc tacttccctg     7860
attggcagaa ctacacacca ggcccagggg tcagatatcc actgacccttt ggatggtgct     7920
acaagctagt accagttgag ccagataagg tagaagaggc caataaagga gagaacacca     7980
gcttgttaca ccctgtgagc ctgcatggaa tggatgaccc tgagagagaa gtgttagagt     8040
ggaggtttga cagccgccta gcatttcatc acgtggcccg agagctgcat ccggagtact     8100
tcaagaactg ctgacatcga gcttgctaca agggactttc cgctgggac tttccaggga     8160
ggcgtggcct gggcgggact ggggagtggc gagccctcag atgctgcata taagcagctg     8220
cttttttgcct gtactgggtc tctctggtta gaccagatct gagcctggga gctctctggc     8280
taactaggga acccactgct taagcctcaa taaagcttgc cttgagtgct tcaagtagtg     8340
tgtgcccgtc tgttgtgtga ctctggtaac tagagatccc tcagaccctt ttagtcagtg     8400
tggaaaatct ctagca                                                     8416
```

<210> SEQ ID NO 2
<211> LENGTH: 86
<212> TYPE: PRT
<213> ORGANISM: Human Immunodeficiency Virus
<220> FEATURE:
<223> OTHER INFORMATION: Tat

<400> SEQUENCE: 2

```
Met Glu Pro Val Asp Pro Arg Leu Glu Pro Trp Lys His Pro Gly Ser
 1               5                  10                  15

Gln Pro Lys Thr Ala Cys Thr Asn Cys Tyr Cys Lys Lys Cys Cys Phe
             20                  25                  30

His Cys Gln Val Cys Phe Met Thr Lys Ala Leu Gly Ile Ser Tyr Gly
         35                  40                  45

Arg Lys Lys Arg Arg Gln Arg Arg Arg Ala His Gln Asn Ser Gln Thr
     50                  55                  60
```

His Gln Ala Ser Leu Ser Lys Gln Pro Thr Ser Gln Ser Arg Gly Asp
65                  70                  75                  80

Pro Thr Gly Pro Lys Glu
                85

<210> SEQ ID NO 3
<211> LENGTH: 116
<212> TYPE: PRT
<213> ORGANISM: Human Immunodeficiency Virus
<220> FEATURE:
<223> OTHER INFORMATION: Rev

<400> SEQUENCE: 3

Met Ala Gly Arg Ser Gly Asp Ser Asp Glu Glu Leu Ile Arg Thr Val
1               5                   10                  15

Arg Leu Ile Lys Leu Leu Tyr Gln Ser Asn Pro Pro Asn Pro Glu
            20                  25                  30

Gly Thr Arg Gln Ala Arg Arg Asn Arg Arg Arg Trp Arg Glu Arg
        35                  40                  45

Gln Arg Gln Ile His Ser Ile Ser Glu Arg Ile Leu Ser Thr Tyr Leu
    50                  55                  60

Gly Arg Ser Ala Glu Pro Val Pro Leu Gln Leu Pro Pro Leu Glu Arg
65                  70                  75                  80

Leu Thr Leu Asp Cys Asn Glu Asp Cys Gly Thr Ser Gly Thr Gln Gly
                85                  90                  95

Val Gly Ser Pro Gln Ile Leu Val Glu Ser Pro Thr Ile Leu Glu Ser
            100                 105                 110

Gly Ala Lys Glu
            115

<210> SEQ ID NO 4
<211> LENGTH: 500
<212> TYPE: PRT
<213> ORGANISM: Human Immunodeficiency Virus
<220> FEATURE:
<223> OTHER INFORMATION: gag

<400> SEQUENCE: 4

Met Gly Ala Arg Ala Ser Val Leu Ser Gly Gly Glu Leu Asp Lys Trp
1               5                   10                  15

Glu Lys Ile Arg Leu Arg Pro Gly Gly Lys Lys Gln Tyr Lys Leu Lys
            20                  25                  30

His Ile Val Trp Ala Ser Arg Glu Leu Glu Arg Phe Ala Val Asn Pro
        35                  40                  45

Gly Leu Leu Glu Thr Ser Glu Gly Cys Arg Gln Ile Leu Gly Gln Leu
    50                  55                  60

Gln Pro Ser Leu Gln Thr Gly Ser Glu Glu Leu Arg Ser Leu Tyr Asn
65                  70                  75                  80

Thr Ile Ala Val Leu Tyr Cys Val His Gln Arg Ile Asp Val Lys Asp
                85                  90                  95

Thr Lys Glu Ala Leu Asp Lys Ile Glu Glu Glu Gln Asn Lys Ser Lys
            100                 105                 110

Lys Lys Ala Gln Gln Ala Ala Ala Asp Thr Gly Asn Asn Ser Gln Val
        115                 120                 125

Ser Gln Asn Tyr Pro Ile Val Gln Asn Leu Gln Gly Gln Met Val His
    130                 135                 140

Gln Ala Ile Ser Pro Arg Thr Leu Asn Ala Trp Val Lys Val Val Glu
145                 150                 155                 160

Glu Lys Ala Phe Ser Pro Glu Val Ile Pro Met Phe Ser Ala Leu Ser
            165                 170                 175

Glu Gly Ala Thr Pro Gln Asp Leu Asn Thr Met Leu Asn Thr Val Gly
            180                 185                 190

Gly His Gln Ala Ala Met Gln Met Leu Lys Glu Thr Ile Asn Glu Glu
            195                 200                 205

Ala Ala Glu Trp Asp Arg Leu His Pro Val His Ala Gly Pro Ile Ala
210                 215                 220

Pro Gly Gln Met Arg Glu Pro Arg Gly Ser Asp Ile Ala Gly Thr Thr
225                 230                 235                 240

Ser Thr Leu Gln Glu Gln Ile Gly Trp Met Thr His Asn Pro Pro Ile
            245                 250                 255

Pro Val Gly Glu Ile Tyr Lys Arg Trp Ile Ile Leu Gly Leu Asn Lys
            260                 265                 270

Ile Val Arg Met Tyr Ser Pro Thr Ser Ile Leu Asp Ile Arg Gln Gly
            275                 280                 285

Pro Lys Glu Pro Phe Arg Asp Tyr Val Asp Arg Phe Tyr Lys Thr Leu
            290                 295                 300

Arg Ala Glu Gln Ala Ser Gln Glu Val Lys Asn Trp Met Thr Glu Thr
305                 310                 315                 320

Leu Leu Val Gln Asn Ala Asn Pro Asp Cys Lys Thr Ile Leu Lys Ala
            325                 330                 335

Leu Gly Pro Gly Ala Thr Leu Glu Glu Met Met Thr Ala Cys Gln Gly
            340                 345                 350

Val Gly Gly Pro Gly His Lys Ala Arg Val Leu Ala Glu Ala Met Ser
            355                 360                 365

Gln Val Thr Asn Pro Ala Thr Ile Met Ile Gln Lys Gly Asn Phe Arg
            370                 375                 380

Asn Gln Arg Lys Thr Val Lys Cys Phe Asn Cys Gly Lys Glu Gly His
385                 390                 395                 400

Ile Ala Lys Asn Cys Arg Ala Pro Arg Lys Lys Gly Cys Trp Lys Cys
            405                 410                 415

Gly Lys Glu Gly His Gln Met Lys Asp Cys Thr Glu Arg Gln Ala Asn
            420                 425                 430

Phe Leu Gly Lys Ile Trp Pro Ser His Lys Gly Arg Pro Gly Asn Phe
            435                 440                 445

Leu Gln Ser Arg Pro Glu Pro Thr Ala Pro Pro Glu Glu Ser Phe Arg
            450                 455                 460

Phe Gly Glu Glu Thr Thr Thr Pro Ser Gln Lys Gln Glu Pro Ile Asp
465                 470                 475                 480

Lys Glu Leu Tyr Pro Leu Ala Ser Leu Arg Ser Leu Phe Gly Ser Asp
            485                 490                 495

Pro Ser Ser Gln
            500

<210> SEQ ID NO 5
<211> LENGTH: 1435
<212> TYPE: PRT
<213> ORGANISM: Human Immunodeficiency Virus
<220> FEATURE:
<223> OTHER INFORMATION: gagpol

<400> SEQUENCE: 5

Met Gly Ala Arg Ala Ser Val Leu Ser Gly Gly Glu Leu Asp Lys Trp
1               5                   10                  15

```
Glu Lys Ile Arg Leu Arg Pro Gly Gly Lys Gln Tyr Lys Leu Lys
         20                  25                  30
His Ile Val Trp Ala Ser Arg Glu Leu Glu Arg Phe Ala Val Asn Pro
         35                  40                  45
Gly Leu Leu Glu Thr Ser Glu Gly Cys Arg Gln Ile Leu Gly Gln Leu
50                   55                  60
Gln Pro Ser Leu Gln Thr Gly Ser Glu Glu Leu Arg Ser Leu Tyr Asn
65                   70                  75                  80
Thr Ile Ala Val Leu Tyr Cys Val His Gln Arg Ile Asp Val Lys Asp
                 85                  90                  95
Thr Lys Glu Ala Leu Asp Lys Ile Glu Glu Gln Asn Lys Ser Lys
            100                 105                 110
Lys Lys Ala Gln Gln Ala Ala Ala Asp Thr Gly Asn Asn Ser Gln Val
            115                 120                 125
Ser Gln Asn Tyr Pro Ile Val Gln Asn Leu Gln Gly Gln Met Val His
130                 135                 140
Gln Ala Ile Ser Pro Arg Thr Leu Asn Ala Trp Val Lys Val Val Glu
145                 150                 155                 160
Glu Lys Ala Phe Ser Pro Glu Val Ile Pro Met Phe Ser Ala Leu Ser
                165                 170                 175
Glu Gly Ala Thr Pro Gln Asp Leu Asn Thr Met Leu Asn Thr Val Gly
            180                 185                 190
Gly His Gln Ala Ala Met Gln Met Leu Lys Glu Thr Ile Asn Glu Glu
        195                 200                 205
Ala Ala Glu Trp Asp Arg Leu His Pro Val His Ala Gly Pro Ile Ala
210                 215                 220
Pro Gly Gln Met Arg Glu Pro Arg Gly Ser Asp Ile Ala Gly Thr Thr
225                 230                 235                 240
Ser Thr Leu Gln Glu Gln Ile Gly Trp Met Thr His Asn Pro Pro Ile
                245                 250                 255
Pro Val Gly Glu Ile Tyr Lys Arg Trp Ile Ile Leu Gly Leu Asn Lys
            260                 265                 270
Ile Val Arg Met Tyr Ser Pro Thr Ser Ile Leu Asp Ile Arg Gln Gly
            275                 280                 285
Pro Lys Glu Pro Phe Arg Asp Tyr Val Asp Arg Phe Tyr Lys Thr Leu
        290                 295                 300
Arg Ala Glu Gln Ala Ser Gln Glu Val Lys Asn Trp Met Thr Glu Thr
305                 310                 315                 320
Leu Leu Val Gln Asn Ala Asn Pro Asp Cys Lys Thr Ile Leu Lys Ala
                325                 330                 335
Leu Gly Pro Gly Ala Thr Leu Glu Glu Met Met Thr Ala Cys Gln Gly
            340                 345                 350
Val Gly Gly Pro Gly His Lys Ala Arg Val Leu Ala Glu Ala Met Ser
            355                 360                 365
Gln Val Thr Asn Pro Ala Thr Ile Met Ile Gln Lys Gly Asn Phe Arg
        370                 375                 380
Asn Gln Arg Lys Thr Val Lys Cys Phe Asn Cys Gly Lys Glu Gly His
385                 390                 395                 400
Ile Ala Lys Asn Cys Arg Ala Pro Arg Lys Lys Gly Cys Trp Lys Cys
                405                 410                 415
Gly Lys Glu Gly His Gln Met Lys Asp Cys Thr Glu Arg Gln Ala Asn
            420                 425                 430
```

```
Phe Leu Arg Glu Asp Leu Ala Phe Pro Gln Gly Lys Ala Arg Glu Phe
            435                 440                 445

Ser Ser Glu Gln Thr Arg Ala Asn Ser Pro Thr Arg Arg Glu Leu Gln
450                 455                 460

Val Trp Gly Arg Asp Asn Asn Ser Leu Ser Glu Ala Gly Ala Asp Arg
465                 470                 475                 480

Gln Gly Thr Val Ser Phe Ser Phe Pro Gln Ile Thr Leu Trp Gln Arg
                485                 490                 495

Pro Leu Val Thr Ile Lys Ile Gly Gly Gln Leu Lys Glu Ala Leu Leu
                500                 505                 510

Asp Thr Gly Ala Asp Asp Thr Val Leu Glu Glu Met Asn Leu Pro Gly
            515                 520                 525

Arg Trp Lys Pro Lys Met Ile Gly Gly Ile Gly Gly Phe Ile Lys Val
        530                 535                 540

Arg Gln Tyr Asp Gln Ile Leu Ile Glu Ile Cys Gly His Lys Ala Ile
545                 550                 555                 560

Gly Thr Val Leu Val Gly Pro Thr Pro Val Asn Ile Ile Gly Arg Asn
                565                 570                 575

Leu Leu Thr Gln Ile Gly Cys Thr Leu Asn Phe Pro Ile Ser Pro Ile
            580                 585                 590

Glu Thr Val Pro Val Lys Leu Lys Pro Gly Met Asp Gly Pro Lys Val
        595                 600                 605

Lys Gln Trp Pro Leu Thr Glu Glu Lys Ile Lys Ala Leu Val Glu Ile
    610                 615                 620

Cys Thr Glu Met Glu Lys Glu Gly Lys Ile Ser Lys Ile Gly Pro Glu
625                 630                 635                 640

Asn Pro Tyr Asn Thr Pro Val Phe Ala Ile Lys Lys Lys Asp Ser Thr
                645                 650                 655

Lys Trp Arg Lys Leu Val Asp Phe Arg Glu Leu Asn Lys Arg Thr Gln
            660                 665                 670

Asp Phe Trp Glu Val Gln Leu Gly Ile Pro His Pro Ala Gly Leu Lys
        675                 680                 685

Gln Lys Lys Ser Val Thr Val Leu Asp Val Gly Asp Ala Tyr Phe Ser
    690                 695                 700

Val Pro Leu Asp Lys Asp Phe Arg Lys Tyr Thr Ala Phe Thr Ile Pro
705                 710                 715                 720

Ser Ile Asn Asn Glu Thr Pro Gly Ile Arg Tyr Gln Tyr Asn Val Leu
                725                 730                 735

Pro Gln Gly Trp Lys Gly Ser Pro Ala Ile Phe Gln Cys Ser Met Thr
            740                 745                 750

Lys Ile Leu Glu Pro Phe Arg Lys Gln Asn Pro Asp Ile Val Ile Tyr
        755                 760                 765

Gln Tyr Met Asp Asp Leu Tyr Val Gly Ser Asp Leu Glu Ile Gly Gln
    770                 775                 780

His Arg Thr Lys Ile Glu Glu Leu Arg Gln His Leu Leu Arg Trp Gly
785                 790                 795                 800

Phe Thr Thr Pro Asp Lys Lys His Gln Lys Glu Pro Pro Phe Leu Trp
                805                 810                 815

Met Gly Tyr Glu Leu His Pro Asp Lys Trp Thr Val Gln Pro Ile Val
            820                 825                 830

Leu Pro Glu Lys Asp Ser Trp Thr Val Asn Asp Ile Gln Lys Leu Val
        835                 840                 845

Gly Lys Leu Asn Trp Ala Ser Gln Ile Tyr Ala Gly Ile Lys Val Arg
```

```
            850                 855                 860
Gln Leu Cys Lys Leu Leu Arg Gly Thr Lys Ala Leu Thr Glu Val Val
865                 870                 875                 880

Pro Leu Thr Glu Glu Ala Glu Leu Glu Leu Ala Glu Asn Arg Glu Ile
                885                 890                 895

Leu Lys Glu Pro Val His Gly Val Tyr Tyr Asp Pro Ser Lys Asp Leu
                900                 905                 910

Ile Ala Glu Ile Gln Lys Gln Gly Gln Gly Gln Trp Thr Tyr Gln Ile
                915                 920                 925

Tyr Gln Glu Pro Phe Lys Asn Leu Lys Thr Gly Lys Tyr Ala Arg Met
                930                 935                 940

Lys Gly Ala His Thr Asn Asp Val Lys Gln Leu Thr Glu Ala Val Gln
945                 950                 955                 960

Lys Ile Ala Thr Glu Ser Ile Val Ile Trp Gly Lys Thr Pro Lys Phe
                965                 970                 975

Lys Leu Pro Ile Gln Lys Glu Thr Trp Glu Ala Trp Trp Thr Glu Tyr
                980                 985                 990

Trp Gln Ala Thr Trp Ile Pro Glu Trp Glu Phe Val Asn Thr Pro Pro
                995                 1000                1005

Leu Val Lys Leu Trp Tyr Gln Leu Glu Lys Glu Pro Ile Ile Gly Ala
                1010                1015                1020

Glu Thr Phe Tyr Val Asp Gly Ala Ala Asn Arg Glu Thr Lys Leu Gly
1025                1030                1035                1040

Lys Ala Gly Tyr Val Thr Asp Arg Gly Arg Gln Lys Val Val Pro Leu
                1045                1050                1055

Thr Asp Thr Thr Asn Gln Lys Thr Glu Leu Gln Ala Ile His Leu Ala
                1060                1065                1070

Leu Gln Asp Ser Gly Leu Glu Val Asn Ile Val Thr Asp Ser Gln Tyr
                1075                1080                1085

Ala Leu Gly Ile Ile Gln Ala Gln Pro Asp Lys Ser Glu Ser Glu Leu
                1090                1095                1100

Val Ser Gln Ile Ile Glu Gln Leu Ile Lys Lys Glu Lys Val Tyr Leu
1105                1110                1115                1120

Ala Trp Val Pro Ala His Lys Gly Ile Gly Gly Asn Glu Gln Val Asp
                1125                1130                1135

Gly Leu Val Ser Ala Gly Ile Arg Lys Val Leu Phe Leu Asp Gly Ile
                1140                1145                1150

Asp Lys Ala Gln Glu Glu His Glu Lys Tyr His Ser Asn Trp Arg Ala
                1155                1160                1165

Met Ala Ser Asp Phe Asn Leu Pro Pro Val Val Ala Lys Glu Ile Val
                1170                1175                1180

Ala Ser Cys Asp Lys Cys Gln Leu Lys Gly Glu Ala Met His Gly Gln
1185                1190                1195                1200

Val Asp Cys Ser Pro Gly Ile Trp Gln Leu Asp Cys Thr His Leu Glu
                1205                1210                1215

Gly Lys Val Ile Leu Val Ala Val His Val Ala Ser Gly Tyr Ile Glu
                1220                1225                1230

Ala Glu Val Ile Pro Ala Glu Thr Gly Gln Glu Thr Ala Tyr Phe Leu
                1235                1240                1245

Leu Lys Leu Ala Gly Arg Trp Pro Val Lys Thr Val His Thr Asp Asn
                1250                1255                1260

Gly Ser Asn Phe Thr Ser Thr Val Lys Ala Ala Cys Trp Trp Ala
1265                1270                1275                1280
```

Gly Ile Lys Gln Glu Phe Gly Ile Pro Tyr Asn Pro Gln Ser Gln Gly
            1285                1290                1295

Val Ile Glu Ser Met Asn Lys Glu Leu Lys Lys Ile Ile Gly Gln Val
        1300                1305                1310

Arg Asp Gln Ala Glu His Leu Lys Thr Ala Val Gln Met Ala Val Phe
        1315                1320                1325

Ile His Asn Phe Lys Arg Lys Gly Gly Ile Gly Gly Tyr Ser Ala Gly
        1330                1335                1340

Glu Arg Ile Val Asp Ile Ile Ala Thr Asp Ile Gln Thr Lys Glu Leu
1345                1350                1355                1360

Gln Lys Gln Ile Thr Lys Ile Gln Asn Phe Arg Val Tyr Tyr Arg Asp
            1365                1370                1375

Ser Arg Asp Pro Val Trp Lys Gly Pro Ala Lys Leu Leu Trp Lys Gly
            1380                1385                1390

Glu Gly Ala Val Val Ile Gln Asp Asn Ser Asp Ile Lys Val Val Pro
            1395                1400                1405

Arg Arg Lys Ala Lys Ile Ile Arg Asp Tyr Gly Lys Gln Met Ala Gly
        1410                1415                1420

Asp Asp Cys Val Ala Ser Arg Gln Asp Glu Asp
1425                1430                1435

<210> SEQ ID NO 6
<211> LENGTH: 261
<212> TYPE: DNA
<213> ORGANISM: Human Immunodeficiency Virus
<220> FEATURE:
<223> OTHER INFORMATION: DNA encoding Tat

<400> SEQUENCE: 6
atggagccag tagatcctag actagagccc tggaagcatc caggaagtca gcctaaaact      60
gcttgtacca attgctattg taaaaagtgt tgctttcatt gccaagtttg tttcatgaca     120
aaagccttag gcatctccta tggcaggaag aagcggagac agcgacgaag agctcatcag     180
aacagtcaga ctcatcaagc ttctctatca aagcaaccca cctcccaatc ccgaggggac     240
ccgacaggcc cgaaggaata g                                               261

<210> SEQ ID NO 7
<211> LENGTH: 351
<212> TYPE: DNA
<213> ORGANISM: Human Immunodeficiency Virus
<220> FEATURE:
<223> OTHER INFORMATION: DNA encoding Rev

<400> SEQUENCE: 7
atggcaggaa gaagcggaga cagcgacgaa gagctcatca gaacagtcag actcatcaag      60
cttctctatc aaagcaaccc acctcccaat cccgagggga cccgacaggc ccgaaggaat     120
agaagaagaa ggtggagaga gacagagaca gatccattcg attagtgaac ggatccttag     180
agcacttatc tgggacgatc tgcggagcct gtgcctcttc agctaccacc gcttgagaga     240
cttactcttg attgtaacga ggattgtgga acttctggga cgcagggggt gggaagccct     300
caaatattgg tggaatctcc tacaatattg gagtcaggag ctaaagaata g              351

<210> SEQ ID NO 8
<211> LENGTH: 1503
<212> TYPE: DNA
<213> ORGANISM: Human Immunodeficiency Virus
<220> FEATURE:

<223> OTHER INFORMATION: DNA encoding gag

<400> SEQUENCE: 8

| | |
|---|---|
| atgggtgcga gagcgtcggt attaagcggg ggagaattag ataaatggga aaaaattcgg | 60 |
| ttaaggccag ggggaaagaa acaatataaa ctaaaacata tagtatgggc aagcagggag | 120 |
| ctagaacgat tcgcagttaa tcctggcctt ttagagacat cagaaggctg tagacaaata | 180 |
| ctgggacagc tacaaccatc ccttcagaca ggatcagaag aacttagatc attatataat | 240 |
| acaatagcag tcctctattg tgtgcatcaa aggatagatg taaaagacac caaggaagcc | 300 |
| ttagataaga tagaggaaga gcaaaacaaa agtaagaaaa aggcacagca agcagcagct | 360 |
| gacacaggaa acaacagcca ggtcagccaa aattacccta tagtgcagaa cctccagggg | 420 |
| caaatggtac atcaggccat atcacctaga actttaaatg catgggtaaa agtagtagaa | 480 |
| gagaaggctt tcagcccaga agtaataccc atgttttcag cattatcaga aggagccacc | 540 |
| ccacaagatt taaataccat gctaaacaca gtggggggac atcaagcagc catgcaaatg | 600 |
| ttaaaagaga ccatcaatga ggaagctgca gaatgggata gattgcatcc agtgcatgca | 660 |
| gggcctattg caccaggcca gatgagagaa ccaaggggaa gtgacatagc aggaactact | 720 |
| agtacccttc aggaacaaat aggatggatg acacataatc cacctatccc agtaggagaa | 780 |
| atctataaaa gatggataat cctgggatta aataaaatag taagaatgta tagccctacc | 840 |
| agcattctgg acataagaca aggaccaaag gaacccttta gagactatgt agaccgattc | 900 |
| tataaaactc taagagccga gcaagcttca caagaggtaa aaaattggat gacagaaacc | 960 |
| ttgttggtcc aaaatgcgaa cccagattgt aagactattt taaaagcatt gggaccagga | 1020 |
| gcgacactag aagaaatgat gacagcatgt cagggagtgg ggggacccgg ccataaagca | 1080 |
| agagttttgg ctgaagcaat gagccaagta acaaatccag ctaccataat gatacagaaa | 1140 |
| ggcaatttta ggaaccaaag aaagactgtt aagtgtttca attgtggcaa agaagggcac | 1200 |
| atagccaaaa attgcagggc ccctaggaaa aagggctgtt ggaaatgtgg aaaggaagga | 1260 |
| caccaaatga aagattgtac tgagagacag gctaattttt tagggaagat ctggccttcc | 1320 |
| cacaagggaa ggccagggaa ttttcttcag agcagaccag agccaacagc cccaccagaa | 1380 |
| gagagcttca ggtttgggga gagacaaca actccctctc agaagcagga gccgatagac | 1440 |
| aaggaactgt atcctttagc ttccctcaga tcactctttg gcagcgaccc ctcgtcacaa | 1500 |
| taa | 1503 |

<210> SEQ ID NO 9
<211> LENGTH: 4308
<212> TYPE: DNA
<213> ORGANISM: Human Immunodeficiency Virus
<220> FEATURE:
<223> OTHER INFORMATION: DNA encoding gagpol

<400> SEQUENCE: 9

| | |
|---|---|
| atgggtgcga gagcgtcggt attaagcggg ggagaattag ataaatggga aaaaattcgg | 60 |
| ttaaggccag ggggaaagaa acaatataaa ctaaaacata tagtatgggc aagcagggag | 120 |
| ctagaacgat tcgcagttaa tcctggcctt ttagagacat cagaaggctg tagacaaata | 180 |
| ctgggacagc tacaaccatc ccttcagaca ggatcagaag aacttagatc attatataat | 240 |
| acaatagcag tcctctattg tgtgcatcaa aggatagatg taaaagacac caaggaagcc | 300 |
| ttagataaga tagaggaaga gcaaaacaaa agtaagaaaa aggcacagca agcagcagct | 360 |
| gacacaggaa acaacagcca ggtcagccaa aattacccta tagtgcagaa cctccagggg | 420 |

```
caaatggtac atcaggccat atcacctaga actttaaatg catgggtaaa agtagtagaa    480
gagaaggctt tcagcccaga agtaataccc atgttttcag cattatcaga aggagccacc    540
ccacaagatt taaataccat gctaaacaca gtgggggac atcaagcagc catgcaaatg     600
ttaaaagaga ccatcaatga ggaagctgca gaatgggata gattgcatcc agtgcatgca    660
gggcctattg caccaggcca gatgagagaa ccaaggggaa gtgacatagc aggaactact    720
agtacccttc aggaacaaat aggatggatg acacataatc cacctatccc agtaggagaa    780
atctataaaa gatggataat cctgggatta aataaaatag taagaatgta tagccctacc    840
agcattctgg acataagaca aggaccaaag gaacccttta gagactatgt agaccgattc    900
tataaaactc taagagccga gcaagcttca caagaggtaa aaaattggat gacagaaacc    960
ttgttggtcc aaaatgcgaa cccagattgt aagactattt taaaagcatt gggaccagga   1020
gcgacactag aagaaatgat gacagcatgt cagggagtgg ggggacccgg ccataaagca   1080
agagttttgg ctgaagcaat gagccaagta acaaatccag ctaccataat gatacagaaa   1140
ggcaatttta ggaaccaaag aaagactgtt aagtgtttca attgtggcaa agaagggcac   1200
atagccaaaa attgcagggc ccctaggaaa aagggctgtt ggaaatgtgg aaaggaagga   1260
caccaaatga aagattgtac tgagagacag gctaattttt taagggaaga tctggccttc   1320
ccacaaggga aggccaggga attttcttca gagcagacca gagccaacag ccccaccaga   1380
agagagcttc aggtttgggg aagagacaac aactccctct cagaagcagg agccgataga   1440
caaggaactg tatcctttag cttccctcag atcactcttt ggcagcgacc cctcgtcaca   1500
ataaagatag ggggcaatt aaaggaagct ctattagata caggagcaga tgatacagta    1560
ttagaagaaa tgaatttgcc aggaagatgg aaaccaaaaa tgataggggg aattggaggt   1620
tttatcaaag taagacagta tgatcagata ctcatagaaa tctgcggaca taaagctata   1680
ggtacagtat tagtaggacc tacacctgtc aacataattg gaagaaatct gttgactcag   1740
attggctgca ctttaaattt tcccattagt cctattgaga ctgtaccagt aaaattaaag   1800
ccaggaatgg atggcccaaa agttaaacaa tggccattga cagaagaaaa aataaaagca   1860
ttagtagaaa tttgtacaga aatggaaaag gaaggaaaaa tttcaaaaat tgggcctgaa   1920
aatccataca atactccagt atttgccata aagaaaaaag acagtactaa atggagaaaa   1980
ttagtagatt tcagagaact taataagaga actcaagatt tctgggaagt tcaattagga   2040
ataccacatc ctgcagggtt aaaacagaaa aaatcagtaa cagtactgga tgtgggcgat   2100
gcatattttt cagttccctt agataaagac ttcaggaagt atactgcatt taccatacct   2160
agtataaaca atgagacacc agggattaga tatcagtaca atgtgcttcc acagggatgg   2220
aaaggatcac cagcaatatt ccagtgtagc atgacaaaaa tcttagagcc ttttagaaaa   2280
caaaatccag acatagtcat ctatcaatac atggatgatt tgtatgtagg atctgactta   2340
gaaatagggc agcatagaac aaaaatagag gaactgagac aacatctgtt gaggtgggga   2400
tttaccacac cagacaaaaa acatcagaaa gaacctccat tcctttggat gggttatgaa   2460
ctccatcctg ataaatggac agtacagcct atagtgctgc cagaaaagga cagctggact   2520
gtcaatgaca tacagaaatt agtgggaaaa ttgaattggg caagtcagat ttatgcaggg   2580
attaaagtaa ggcaattatg taaacttctt aggggaacca aagcactaac agaagtagta   2640
ccactaacag aagaagcaga gctagaactg gcagaaaaca gggagattct aaaagaaccg   2700
gtacatggag tgtattatga cccatcaaaa gacttaatag cagaaataca gaagcagggg   2760
```

| | |
|---|---:|
| caaggccaat ggacatatca aatttatcaa gagccattta aaaatctgaa acaggaaaaa | 2820 |
| tatgcaagaa tgaagggtgc ccacactaat gatgtgaaac aattaacaga ggcagtacaa | 2880 |
| aaaatagcca cagaaagcat agtaatatgg ggaaagactc ctaaatttaa attacccata | 2940 |
| caaaaggaaa catgggaagc atggtggaca gagtattggc aagccacctg gattcctgag | 3000 |
| tgggagtttg tcaataccc tcccttagtg aagttatggt accagttaga gaaagaaccc | 3060 |
| ataataggag cagaaacttt ctatgtagat ggggcagcca atagggaaac taaattagga | 3120 |
| aaagcaggat atgtaactga cagaggaaga caaaaagttg tccccctaac ggacacaaca | 3180 |
| aatcagaaga ctgagttaca agcaattcat ctagctttgc aggattcggg attagaagta | 3240 |
| aacatagtga cagactcaca atatgcattg gaatcattc aagcacaacc agataagagt | 3300 |
| gaatcagagt tagtcagtca aataatagag cagttaataa aaaggaaaaa agtctacctg | 3360 |
| gcatgggtac cagcacacaa aggaattgga ggaaatgaac aagtagatgg gttggtcagt | 3420 |
| gctggaatca ggaaagtact attttagat ggaatagata aggcccaaga gaacatgag | 3480 |
| aaatatcaca gtaattggag agcaatggct agtgatttta acctaccacc tgtagtagca | 3540 |
| aaagaaatag tagccagctg tgataaatgt cagctaaaag gggaagccat gcatggacaa | 3600 |
| gtagactgta gcccaggaat atggcagcta gattgtacac atttagaagg aaaagttatc | 3660 |
| ttggtagcag ttcatgtagc cagtggatat atagaagcag aagtaattcc agcagagaca | 3720 |
| gggcaagaaa cagcatactt cctcttaaaa ttagcaggaa gatggccagt aaaaacagta | 3780 |
| catacagaca atggcagcaa tttcaccagt actacagtta aggccgcctg ttggtgggcg | 3840 |
| gggatcaagc aggaatttgg cattccctac aatccccaaa gtcaaggagt aatagaatct | 3900 |
| atgaataaag aattaaagaa aattatagga caggtaagag atcaggctga acatcttaag | 3960 |
| acagcagtac aaatggcagt attcatccac aatttaaaa gaaaggggg gattgggggg | 4020 |
| tacagtgcag gggaagaat agtagacata atagcaacag acatacaaac taaagaatta | 4080 |
| caaaaacaaa ttacaaaaat tcaaaatttt cgggtttatt acagggacag cagagatcca | 4140 |
| gtttggaaag gaccagcaaa gctcctctgg aaaggtgaag gggcagtagt aatacaagat | 4200 |
| aatagtgaca taaagtagt gccaagaaga aaagcaaaga tcatcaggga ttatggaaaa | 4260 |
| cagatggcag gtgatgattg tgtggcaagt agacaggatg aggattaa | 4308 |

<210> SEQ ID NO 10
<211> LENGTH: 663
<212> TYPE: DNA
<213> ORGANISM: Artificial Sequence
<220> FEATURE:
<223> OTHER INFORMATION: DNA encoding synthetic fusion protein
      comprising simian immunodeficiency virus mac251 Vpx and human
      immunodeficiency virus-1 NL4-3 Vpr

<400> SEQUENCE: 10

| | |
|---|---:|
| atgtcagatc ccagggagag aatcccacct ggaaacagtg agaagagac aataggagag | 60 |
| gccttcgaat ggctaaacag aacagtagag gagataaaca gagaggcagt aaaccaccta | 120 |
| ccaagggagc tgattttcca ggtttggcaa aggtcttggg aatactggca tgatgaacaa | 180 |
| gggatgtcac aaagctatgt aaaatacaga tacttgtgtt taatgcaaaa ggctttattt | 240 |
| atgcattgca agaaaggctg tagatgtcta ggggaaggac acggggcagg aggatggaga | 300 |
| ccaggacctc ctcctcctcc ccctccagga ctagcagcga actatgcggc agctgccgcg | 360 |
| gcagctgatc cgagcgaaca agccccagaa gaccaagggc cacagaggga gccatacaat | 420 |
| gaatggacac tagagctttt agaggaactt aagagtgaag ctgttagaca ttttcctagg | 480 |

```
atatggctcc ataacttagg acaacatatc tatgaaactt acggggatac ttgggcagga      540
gtggaagcca taataagaat tctgcaacaa ctgctgttta tccatttcag aattgggtgt      600
cgacatagca aataggcgt tactcgacag aggagagcaa aaatggagc cagtagatcc        660 tag                                                                    663

<210> SEQ ID NO 11
<211> LENGTH: 339
<212> TYPE: DNA
<213> ORGANISM: Artificial Sequence
<220> FEATURE:
<223> OTHER INFORMATION: DNA encoding synthetic protein comprising
      simian immunodeficiency virus mac251 Vpx

<400> SEQUENCE: 11
atgtcagatc ccagggagag aatcccacct ggaaacagtg agaagagac aataggagag        60 gccttcgaat ggctaaacag aacagtagag gagataaaca gagaggcagt aaaccaccta      120
ccaagggagc tgattttcca ggtttggcaa aggtcttggg aatactggca tgatgaacaa      180
gggatgtcac aaagctatgt aaaatacaga tacttgtgtt taatgcaaaa ggctttattt      240
atgcattgca agaaaggctg tagatgtcta ggggaaggac acggggcagg aggatggaga      300
ccaggacctc ctcctcctcc cctccagga ctagcataa                              339

<210> SEQ ID NO 12
<211> LENGTH: 7640
<212> TYPE: DNA
<213> ORGANISM: Artificial Sequence
<220> FEATURE:
<223> OTHER INFORMATION: Synthetic viral vector comprising simian
      immunodeficiency virus VLP and VSV-G

<400> SEQUENCE: 12
gcgttacata acttacggta aatggcccgc ctggctgacc gcccaacgac ccccgcccat       60
tgacgtcaat aatgacgtat gttcccatag taacgccaat agggactttc cattgacgtc      120
aatgggtgga gtatttacgg taaactgccc acttggcagt acatcaagtg tatcatatgc      180
caagtacgcc ccctattgac gtcaatgacg gtaaatggcc cgcctggcat tatgcccagt      240
acatgacctt atgggacttt cctacttggc agtacatcta cgtattagtc atcgctatta      300
ccatggtgat gcggttttgg cagtacatca atgggcgtgg atagcggttt gactcacggg      360
gatttccaag tctccacccc attgacgtca atgggagttt gttttggcac caaaatcaac      420
gggactttcc aaaatgtcgt aacaactccg ccccattgac gcaaatgggc ggtaggcgtg      480
tacggtggga ggtctatata agcagagctc gtttagtgaa ccgtcagatc gcctggagac      540
gccatccacg ctgttttgac ctccatagaa gacaccggga ccgatccagc ctccggtcga      600
ggccgcaagc ttggcctccg gttgcaggta agtgcaacac aaaaaagaaa tagctgtctt      660
gttatccagg aagggataat aagatagagt gggagatggg cgcagaaac tccgtcttgt       720 cagggaagaa agcagatgaa ttagaaaaaa ttaggctacg acccggcgga agaaaaagt       780 acatgttgaa gcatgtagta tgggcagcaa atgaattaga tagatttgga ttagcagaaa      840
gcctgttgga gaacaagaa ggatgtcaaa aaatactttc ggtcttagct ccattagtgc       900
caacaggctc agaaaattta aaaagccttt ataatactgt ctgcgtcatc tggtgcattc      960
acgcagaaga gaaagtgaaa cacactgagg aagcaaaaca gatagtgcag agacacctag     1020
tggtggaaac aggaacagca gaaactatgc caaaaacaag tagaccaaca gcaccatcta     1080
```

```
gcggcagagg aggaaattac ccagtacaac aaataggtgg taactatgtt cacctggcat    1140
taagcccgag aacattaaat gcctgggtaa aattgataga ggaaaagaaa tttggagcag    1200
aagtagtgcc aggatttcag gcactgtcag aaggctgcac cccctatgac attaatcaga    1260
tgttaaattg tgtgggagac catcaagcgg ctatgcagat tatcagagat attataaatg    1320
aggaggctgc agattgggac ttgcagcacc cacaaccagc tccacaacaa ggacagctta    1380
gggagccgtc aggatcagat attgcaggaa caactagttc agtagatgaa caaatccagt    1440
ggatgtacag acaacagaac cccataccag taggcaacat ttacaggaga tggatccaac    1500
tggggttgca aaaatgtgtc agaatgtata acccaacaaa cattctagat gtaaaacaag    1560
ggccaaaaga gccatttcag agctatgtag acaggttcta caaaagctta agagcagaac    1620
aaacagatgc agcagtaaag aattggatga ctcaaacact gctgattcaa aatgctaacc    1680
cagattgcaa gctagtgctg aagggctggg gtgtgaatcc caccctagaa gaaatgctga    1740
cggcttgtca aggagtaggg ggaccaggac agaaggctag attaatggca gaagccctga    1800
aagaggccct cgcaccagtg ccaatcccct ttgcagcagc ccagaagagg ggaccaagaa    1860
agccaattaa gtgttggaat tgtgggaagg agggacactc tgcaaggcaa tgcagagccc    1920
caagaagaca gggatgctgg aaatgtggaa aaatggacca tgttatggcc aaatgcccag    1980
acagacaggc gggtttttta ggccttggtc catggggaaa aagcccccgc aatttcccca    2040
tggctcaagt gcatcagggg ctgacgccaa ctgctccccc agaggaccca gctgtggatc    2100
tgctaaagaa ctacatgcag ttgggcaagc agcagagaga aagcagagag aagccttaca    2160
aggaggtgac agaggatttg ctgcacctca attctctctt tggaggagac cagtagtcac    2220
tgctcatatt gaaggacagc ctgtagaagt attattggat acagggctg atgattctat    2280 tgtaacagga atagagttag gtccacatta taccccaaaa atagtaggag aataggagg    2340 ttttattaat actaaagaat acaaaaatgt aaaaatagaa gttttaggca aaaggattaa    2400
agggacaatc atgacagggg acactccgat taacatttt ggtaggaatt tgctaacagc    2460
tctggggatg tctctaaatc ttcccatagc taaggtagag cctgtaaaag tcaccttaaa    2520
gccaggaaag gttggaccaa aattgaagca gtggccatta tcaaaagaaa agatagttgc    2580
attaagagaa atctgtgaaa agatggaaaa ggatggtcag ttggaggaag ctcccccgac    2640
caatccatac aacaccccca catttgccat aaagaaaaaa gataagaaca aatggagaat    2700
gctgatagat tttagggaac taaataggt cactcaggac tttacagaag tccaattagg    2760
aataccacac cctgcaggac tagcaaaaag gaaaaggatt acagtactgg atataggtga    2820
tgcatatttc tccataccctc tagatgaaga atttaggcag tacactgcct ttactttacc    2880
atcagtaaat aatgcagagc caggaaaacg atacatttat aaggttctgc ctcagggatg    2940
gaaggggtca ccagccatct tccaatacac tatgagacat gtgctagaac ccttcaggaa    3000
ggcaaatcca gatgtgacct tagtccagta tatggatgac atcttaatag ctagtgacag    3060
gacagacctg gaacatgaca gggtagtttt acagctaaag gaactcttaa atagcatagg    3120
gttctctacc ccagaagaga aattccaaaa agatcccca tttcaatgga tggggtacga    3180
attgtggccg acaaaatgga agttgcaaaa gatagagttg ccacaaagag agacctggac    3240
agtgaatgat atacagaagt tagtaggagt attaaattgg gcagctcaaa tttatccagg    3300
tataaaaacc aaacatctct gtaggttaat tagaggaaaa atgactctaa cagaggaagt    3360
tcagtggact gagatggcag aagcagaata tgaggaaaat aagataattc tcagtcagga    3420
acaagaagga tgttattacc aagaaggcaa gccattagaa gccacggtaa taagagtca    3480
```

```
ggacaatcag tggtcttata aaattcacca agaagacaaa atactgaaag taggaaaatt     3540
tgcaaagata aagaatacac ataccaatgg agttagacta ttagcacatg taatacagaa     3600
aataggaaag gaagcaatag tgatctgggg acaggtccca aaattccact taccagttga     3660
gagggatgta tgggaacagt ggtggacaga ctattggcag gtaacctgga taccggagtg     3720
ggattttatc tcaacgccac cactagtaag attagtcttc aatctagtga aggaccctat     3780
agagggagaa gaaacctatt atacagatgg atcatgtaat aaacagtcaa agaagggaa     3840 agcaggatat atcacagata ggggcaaaga caaagtaaaa gtgttagaac agactactaa     3900
tcaacaagca gaattagaag catttctcat ggcattgaca gactcagggc aaagacaaa     3960 tattatagta gattcacaat atgttatggg aataataaca ggatgcccta cagaatcaga     4020
gagcaggcta gttaaccaaa taatagaaga aatgattaaa aagtcagaaa tttatgtagc     4080
atgggtacca gcacacaaag gtataggagg aaaccaagaa atagaccacc tagttagtca     4140
ggggattaga caagttctct tcttggaaaa gatagagcca gcacaagaag aacatgataa     4200
ataccatagt aatgtaaaag aattggtatt caaatttgga ttacccagaa tagtggccag     4260
acagatagta gacacctgtg ataaatgtca tcagaaagga gaagctatac atgggcaggt     4320
aaattcagat ctagggactt ggcaaatgga ctgtacccat ctagaaggaa aaatagtcat     4380
agttgcagta catgtagcta gtggattcat agaagcagaa gtaattccac aagagacagg     4440
aagacagaca gcactatttc tgttaaaatt ggcaggcaga tggcctatta cacatctaca     4500
cacagataat ggtgctaact ttgcctcgca agaagtaaag atggttgcat ggtgggcagg     4560
gatagagcac accttgggg taccatacaa tccacagagt cagggagtag tggaagcaat     4620
gaatcaccac ctgaaaaatc aaatagatag aatcagggaa caagcaaatt cagtagaaac     4680
catagtatta atggcagttc attgcatgaa ttttaaaaga agggaggaa tagggatat     4740 gactccagca gaaagattaa ttaacatgat cactacagaa caagaaatac aatttcaaca     4800
atcaaaaaac tcaaaatttta aaattttcg ggtctattac agagaaggca gagatcaact     4860
gtggaaggga cccggtgagc tattgtggaa aggggaagga gcagtcatct taaaggtagg     4920
gacagacatt aaggtagtac ccagaagaaa ggctaaaatt atcaaagatt atggaggagg     4980
aaaagaggtg gatagcagtt cccacatgga ggataccgga gaggctagag aggtggcata     5040
gcctcataaa atatctgaaa tataaaacta agatctacaa aaaggtttgc tatgtgcccc     5100 atttaaggt cggatgggca tggtggacct gcagcagagt aatcttcccc ctacaggaag     5160
gaagccattt agaagtacaa gggtattggc atttgacacc agaaagaggg tggctcagta     5220
cttatgcagt gaggataacc tggtactcaa ggaacttttg gacagatgta acaccagact     5280
atgcagacat tttactgcat agcacttatt tccttgctt tacagcggga gaagtgagaa     5340
gggccatcag gggagaacaa ctgctgtctt gctgcaagtt cccgagagct cataggtacc     5400
aggtaccaag cctacagtac ttagcactaa agtagtaag cgatgtcaga tcccagggag     5460
agaatcccac ctggaaacag tggagaagag acaataggag aggccttcga atggctaaac     5520
agaacagtag aggagataaa cagagaggca gtaaaccacc taccaaggga gctgattttc     5580
caggtttggc aaaggtcttg ggaatactgg catgatgaac aagggatgtc acaaagctat     5640
gtaaaataca gatacttgtg tttaatgcaa aaggctttat ttatgcattg caagaaaggc     5700
tgtagatgtc tagggaagg acacgggca ggaggatgga gaccaggacc tcctcctcct     5760 cccctccag gactagcata aatggaagaa agacctccag aaaatgaagg cccacaaagg     5820
```

```
gaaccatggg atgaatgggt agtggaggtt ctggaagaat tgaaagaaga agctttaaaa    5880
cattttgatc ctcgcttgct aactgcactt ggtaatcata tctataatag acatggagac    5940
acccttgagg gagcaggaga actcattaga atcctccaac gagcgctctt catgcatttt    6000
agaggcggat gcaaccactc cagaatcggc caacctgggg gaggaaatcc tctctcaact    6060
ataccgccct cttgaggcgt gctataacac atgctattgt aaaaagtgtt gctaccattg    6120
ccagttttgt tttcttaaaa agggattggg gatatgttat gagcagtcac gaaagagaag    6180
aagaactccg aaaaaggcta aggctaatac atcttctgca tcaaacaagt aagtatgcca    6240
ttgcatacgt tgtatccata tcataatatg tacatttata ttggctcatg tccaacatta    6300
ccgccatgtt gacattgatt attgactagt atcaccatga gtgcagaggt ggcagaactg    6360
tatcgattgg agttgggaga ttataaatta gtagagatca ctccgattgg cttggccccc    6420
acagatgtga agaggtacac tactggtggc acctcaagaa ataaagagg ggtctttgtg     6480 ctagggttct tgggttttct cgcaacggca ggttctgcaa tgggcgcggc gtcgttgacg    6540
ctgaccgctc agtcccggac tttattggct gggatagtgc agcaacagca acagctgttg    6600
gacgtggtca agagacaaca agaattgttg cgactgaccg tctgggggaac aaagaacctc    6660 cagactaggg tcactgccat cgagaagtac ttaaggacc aggcgcagct aaatgcttgg     6720
ggatgtgcgt ttagacaagt ctgccacact actgtaccat ggccaaatgc aagtctaaca    6780
ccagactgga caatgatac ttggcaagag tgggagcgaa aggttgactt cttggaggaa     6840
aatataacag ccctcctaga agaggcacaa attcaacaag aagaacat gtatgaatta     6900 caaaagttga atagctggga tgtgtttggc aattggtttg accttgcttc ttggataaag    6960
tatatacaat atggaattta tgtagttgta ggagtaatac tgttaagaat agtgatctat    7020
atagtacaaa tgctagctaa gttaaggcag gggtataggc cagtgttctc ttccccaccc    7080
tcttatttcc agtagactca tacccaacag gacccggcac tgccaaccag agaaggcaaa    7140
gaaggagacg tggagaagg cggtggcaac agctcctggc cttggcagat agaatatatt    7200
catttcctga tccgccaact gatacgcctc ttgacttggc tattcagcaa ctgcagaacc    7260
ttgctatcga gagcatacca gatcctccaa ccaatactcc agaggctctc tgcgacccta    7320
cgaagggttc gagaagtcct caggactgaa ctgacctacc tacaatatgg gtggagctat    7380
ttccatgagg cggtccaagc cggctggaga tctgcgacag aaactcttgc gggcgcgtgg    7440
agagacttat gggagactct taggagaggt ggaagatgga tcctcgcaat ccctagagat    7500
cataatcagc ataccacat ttgtagaggt tttacttgct ttaaaaaacc tcccacacct     7560 cccctgaac ctgaaacata aaatgaatgc aattgttgtt gttaacttgt ttattgcagc     7620
ttataatggt tacaaataaa                                                7640
```

<210> SEQ ID NO 13
<211> LENGTH: 1536
<212> TYPE: DNA
<213> ORGANISM: Artificial Sequence
<220> FEATURE:
<223> OTHER INFORMATION: Synthetic VSV-G

<400> SEQUENCE: 13

```
atgaagtgcc ttttgtactt agccttttta ttcattgggg tgaattgcaa gttcaccata       60 gttttttccac acaaccaaaa aggaaactgg aaaaatgttc cttctaatta ccattattgc     120
ccgtcaagct cagatttaaa ttggcataat gacttaatag gcacagcctt acaagtcaaa      180
atgcccaaga gtcacaaggc tattcaagca gacggttgga tgtgtcatgc ttccaaatgg      240
```

```
gtcactactt gtgatttccg ctggtatgga ccgaagtata taacacattc catccgatcc      300
ttcactccat ctgtagaaca atgcaaggaa agcattgaac aaacgaaaca aggaacttgg      360
ctgaatccag gcttccctcc tcaaagttgt ggatatgcaa ctgtgacgga tgccgaagca      420
gtgattgtcc agtgactcc tcaccatgtg ctggttgatg aatacacagg agaatgggtt       480
gattcacagt tcatcaacgg aaaatgcagc aattacatat gccccactgt ccataactct      540
acaacctggc attctgacta taaggtcaaa gggctatgtg attctaacct catttccatg      600
gacatcacct tcttctcaga ggacggagag ctatcatccc tgggaaagga gggcacaggg      660
ttcagaagta actactttgc ttatgaaact ggaggcaagg cctgcaaaat gcaatactgc      720
aagcattggg gagtcagact cccatcaggt gtctggttcg agatggctga taaggatctc      780
tttgctgcag ccagattccc tgaatgccca aagggtcaa gtatctctgc tccatctcag      840
acctcagtgg atgtaagtct aattcaggac gttgagagga tcttggatta ttccctctgc      900
caagaaacct ggagcaaaat cagagcgggt cttccaatct ctccagtgga tctcagctat      960
cttgctccta aaacccagg aaccggtcct gctttcacca taatcaatgg taccctaaaa       1020
tactttgaga ccagatacat cagagtcgat attgctgctc caatcctctc aagaatggtc      1080
ggaatgatca gtggaactac cacagaaagg gaactgtggg atgactgggc accatatgaa      1140
gacgtggaaa ttggacccaa tggagttctg aggaccagtt caggatataa gtttccttta      1200
tacatgattg acatggtat gttggactcc gatcttcatc ttagctcaaa ggctcaggtg       1260
ttcgaacatc ctcacattca agacgctgct tcgcaacttc ctgatgatga gagtttattt      1320
tttggtgata ctgggctatc caaaaatcca atcgagcttg tagaaggttg gttcagtagt      1380
tggaaaagct ctattgcctc tttttctttt atcataggt taatcattgg actattcttg       1440
gttctccgag ttggtatcca tctttgcatt aaattaaagc acaccaagaa agacagatt      1500 tatacagaca tagagatgaa ccgacttgga aagtga                                1536

<210> SEQ ID NO 14
<211> LENGTH: 8416
<212> TYPE: RNA
<213> ORGANISM: Artificial Sequence
<220> FEATURE:
<223> OTHER INFORMATION: Human Immunodeficiency Virus Vector

<400> SEQUENCE: 14
uggaagggcu aauuuggucc caaaaaagac aagagauccu ugaucugugg aucuaccaca      60
cacaaggcua cuucccugau ggcagaacu acacaccagg gccagggauc agauauccac       120
ugaccuuugg auggugcuuc aaguuaguac caguugaacc agagcaagua gaagaggcca      180
aauaaggaga gaagaacagc uuguuacacc cuaugagcca gcaugggaug gaggacccgg      240
agggagaagu auuagugugg aaguuugaca gccuccuagc auuucgucac auggcccgag      300
agcugcaucc ggaguacuac aaagacugcu gacaucgagc uuucuacaag ggacuuuccg      360
cuggggacuu uccagggagg uguggccugg gcgggacugg ggaguggcga gcccucagau      420
gcuacauaua agcagcugcu uuugccugu acuggglcuc ucugguuaga ccagaucuga      480
gccugggagc ucucuggcua acuagggaac ccacugcuua agccucaaua aagcuugccu      540
ugagugcuca aaguagugug ugcccgucug uugugugacu cugguaacua gagaucccuc      600
agacccuuuu agucagugug gaaaaucucu agcaguggcg cccgaacagg acuugaaag      660 cgaaaguaaa gccagaggag aucucucgac gcaggacucg gcuugcugaa gcgcgcacgg      720
```

```
caagaggcga ggggcggcga cuggugagua cgccaaaaau uuugacuagc ggaggcuaga    780
aggagagaga ugggugcgag agcgucggua uuaagcgggg gagaauuaga uaaaugggaa    840
aaaauucggu uaaggccagg gggaaagaaa caauauaaac uaaaacauau aguaugggca    900
agcagggagc uagaacgauu cgcaguuaau ccuggccuuu uagagacauc agaaggcugu    960
agacaaauac ugggacagcu acaaccaucc cuucagacag gaucagaaga acuuagauca   1020
uuauauaaua caaugcagu ccucuauugu gugcaucaaa ggauagaugu aaaagacacc    1080
aaggaagccu uagauaagau agaggaagag caaaacaaaa guaagaaaaa ggcacagcaa   1140
gcagcagcug acacaggaaa caacagccag gucagccaaa auuacccuau agugcagaac   1200
cuccaggggc aaaugguaca ucaggccaua ucaccuagaa cuuuaaaugc auggguaaaa   1260
guaguagaag agaaggcuuu cagcccagaa guaauaccca uguuuucagc auuaucagaa   1320
ggagccaccc cacaagauuu aaauaccaug cuaaacacag ugggggggaca ucaagcagcc   1380
augcaaaugu uaaaagagac caucaaugag gaagcugcag aauggGauag auugcaucca   1440
gugcaugcag ggccuauugc accaggccag augagagaac caaggggaag ugacauagca   1500
ggaacuacua guacccuuca ggaacaaaua ggauggauga cacauaaucc accuaucccca   1560
guaggagaaa ucuauaaaag auggauaauc cuggauuaa uaaaauagu aagaaugua    1620
agcccuacca gcauucugga cauaagacaa ggaccaaagg aacccuuuag acuaugua     1680
gaccgauucu auaaaacucu aagagccgag caagcuucac aagagguaaa aaauggaug   1740
acagaaaccu uguuggucca aaaugcgaac ccagauugua agacuauuuu aaaagcauug   1800
ggaccaggag cgacacuaga agaaugaug acagcaugcc agggagugg gggacccggc    1860
cauaaagcaa gaguuuggc ugaagcaaug agccaaguaa caaauccagc uaccauaaug    1920
auacagaaag gcaauuuuag gaaccaaaga aagacuguua aguguucaa uuguggcaaa   1980
gaagggcaca uagccaaaaa uugcagggcc ccuaggaaaa agggcuguug aaaugugga    2040
aaggaaggac accaaaugaa agauuguacu gagagacagg cuaauuuuuu agggaagauc   2100
uggccuuccc acaagggaag gccagggaau uucuucaga gcagaccaga gccaacagcc   2160
ccaccgaaag agagcuucag guuugggaa gagacaacaa ucccucuca gaagcaggag    2220
ccgauagaca aggaacugua uccuuuagcu ucccucagau cacucuuugg cagcgacccc   2280
ucgucacaau aaagauaggg gggcaauuaa aggaagcucu auuagauaca ggagcagaug   2340
auacaguauu agaagaaaug aauuugccag gaagauggaa accaaaaaug auaggggaa   2400
uuggagguuu uaucaaagua agacagauaug aucagauacu cauagaaauc ugcggacaua   2460
aagcuauagg uacaguauua guaggaccua caccugucaa cauaauugga agaaaucugu   2520
ugacucagau uggcugcacu uuaaauuuuc ccauuagucc uauugagacu guaccaguaa   2580
aauuaaagcc aggaauggau ggcccaaaag uuaaacaaug gccauugaca gaagaaaaa    2640
uaaaagcauu aguagaaauu uugacagaaa uggaaaagga aggaaaaauu ucaaaaauug   2700
ggccugaaaa uccauacaau acuccaguau uugccauaaa gaaaaagac aguacuaaau    2760
ggagaaaauu aguagauuuc agagaacuua auaagagaac ucaagauuuc ugggaaguuc   2820
aauuaggaau accacauccu gcagguuaa acagaaaaa aucaguaaca guacuggaug     2880
ugggcgaugc auauuuuuca guucccuuag auaaagacuu caggaaguau acugcauuua   2940
ccauaccuag uauaaacaau gagacaccag ggauuagaua ucagucaauu gugcuuccac   3000
agggauggaa aggaucacca gcaauauucc agugcagcau gacaaaaauc uuagagccuu   3060
uuagaaaaca aaauccagac auagucaucu aucaauacau ggaugauuug uauguaggau   3120
```

```
cugacuuaga aauagggcag cauagaacaa aaauagagga acugagacaa caucuguuga    3180 ggugggggauu uaccacacca gacaaaaaac aucagaaaga accuccauuc cuuuggaugg    3240
guuaugaacu ccauccugau aaauggacag uacagccuau agugcugcca gaaaaggaca    3300
gcuggacugu caaugacaua cagaaauuag ugggaaaauu gaauuggggca agucagauuu    3360 augcagggau uaaaguaagg caauuaugua aacuucuuag gggaaccaaa gcacuaacag    3420
aaguaguacc acuaacagaa gaagcagagc uagaacuggc agaaaacagg gagauucuaa    3480
aagaaccggu acauggagug uauuaugacc caucaaaaga cuuaauagca gaaauacaga    3540
agcaggggca aggccaaugg acauaucaaa uuuaucaaga gccauuuaaa aaucugaaaa    3600
caggaaaaua ugcaagaaug aagggugccc acacuaauga ugugaaacaa uuaacagagg    3660
caguacaaaa aauagccaca gaaagcauag uaauauggggg aaagacuccu aaauuuaaau    3720
uacccauaca aaaggaaaca ugggaagcau gguggacaga guauuggcaa gccaccugga    3780
uuccugagug ggaguuuguc aaucccccuc ccuuagugaa guuaugguac caguuagaga    3840
aagaacccau aauaggagca gaaacuuucu auguagaugg ggcagccaau agggaaacua    3900
aauuaggaaa agcaggauau guaacugaca gaggaagaca aaaaguuguc ccccuaacgg    3960
acacaacaaa ucagaagacu gaguuacaag caauucaucu agcuuugcag gauucgggau    4020
uagaaguaaa cauagugaca gacucacaau augcauggg aaucauucaa gcacaaccag    4080
auaagaguga aucagaguua gucagucaaa uaauagagca guuaauaaaa aaggaaaaag    4140
ucuaccuggc augguaccag cacacaaaagg gaauuggagg aaaugaacaa guagaugggu    4200
uggucagugc uggaaucagg aaaguacuau uuuuagaugg aauagauaag gcccaagaag    4260
aacaugagaa auaucacagu aauuggagag caauggcuag ugauuuuaac cuaccaccug    4320
uaguagcaaa agaaauagua gccagcugug auaaaugucu gcuaaaggg aagccaugc    4380 auggacaagu agacuguagc ccaggaauau ggcagcuaga uuguacacau uuagaaggaa    4440
aaguuaucuu gguagcaguu caugaugcca guggauauau agaagcagaa guauuccag    4500 cagagacagg gcaagaaaca gcauacuucc ucuuaaaauu agcaggaaga uggccaguaa    4560
aaacaguaca uacagacaau ggcagcaauu ucaccaguac uacaguuaag gccgccuguu    4620
ggugggcggg gaucaagcag gaauuuggca uucccuacaa uccccaaagu caaggaguaa    4680
uagaaucuau gaauaaagaa uuaagaaaa uuauaggaca gguaagagau caggcugaac    4740
aucuuaagac agcaguacaa auggcaguau ucauccacaa uuuuaaaaga aagggggga    4800 uuggggggua cagugcaggg gaaagaauag uagacauaau agcaacagac auacaaacua    4860
aagaauuaca aaaacaaauu acaaaauuc aaaauuucg gguuuauuac agggacagca    4920
gagauccagu uggaaagga ccagcaaagc uccucuggaa aggugaaggg gcaguaguaa    4980
uacaagauaa uagugacaua aaaguagugc caagaagaaa agcaaagauc aucagggauu    5040
auggaaaaca gauggcaggu gaugauugu uggcaaguag acaggaugag gauuaacaca    5100
uggaaaagau uaguaaaaca ccauaugga uuggaagcca uaauaagaau uaauucugca    5160
acaacugcug uuuauccauu ucagaauugg gugucgacau agcagaauag gcguuacucg    5220
acagaggaga gcaagaaaug gagccaguag auccuagacu agagcccugg aagcauccag    5280
gaagucagcc uaaaacugcu guaccaauu gcuauguaa aaaguguugc uuucauugcc    5340
aaguuuguuu caugacaaaa gccuuaggca ucuccuaugg caggaagaag cggagacagc    5400
gacgaagagc ucaucagaac agucagacuc aucaagcuuc ucuaucaaag caguaaguag    5460
```

```
uacaugggcg cgcccaugug gcaggaagua ggaaaagcaa uguaugcccc ucccaucagu    5520
ggacaaauua gauguucauc aaauauuacu gggcugcuau uaacaagaga uggugguaau    5580
aacaacaaug gguccgagau cuucagaccu ggaggaggcg auaugaggga caauuggaga    5640
agugaauuau auaaauauaa aguaguaaaa auugaaccau uaggaguagc acccaccaag    5700
gcaaagagaa gaguggugca gagagaaaaa agagcagugg gaauaggagc uuuguuccuu    5760
ggguucuugg gagcagcagg aagcacuaug gcgcgcgcgu caaugacgcu gacgguacag    5820
gccagacaau uauugucuga uauagugcag cagcagaaca auuugcugag ggcuauugag    5880
gcgcaacagc aucguugca acucacaguc uggggcauca aacagcucca ggcaagaauc    5940
cuggcugugg aaagauaccu aaaggaucaa cagcccugg ggauugggg uugcucugga    6000
aaacucauuu gcaccacugc ugugccuugg aaugcuaguu ggaguaauaa ucucuggaa    6060
cagauuugga auaacaugac cuggauggag ugggacagaa aaauuaacaa uuacacaagc    6120
uuaauacacu ccuuaauuga gaaucgcaa aaccagcaag aaaagaauga acaagaauua    6180
uuggaauuag auaaaugggc aaguuugugg aauugguuua acauaacaaa uuggcugugg    6240
uauauaaaau uauucauaau gauaguagga ggcuugguag guuuaagaau aguuuuugcu    6300
guacuuucua uagugaauag aguuaggcag ggauauucac cauuaucguu ucagacccac    6360
cucccaaucc cgaggggacc cgacaggccc gaaggaauag aagaagaagg uggagagaga    6420
gacagagaca gauccauucg auuagugaac ggauccuuag cacuuaucug ggacgaucug    6480
cggagccugu gccucuucag cuaccaccgc uugagagacu acucuugau uguaacgagg    6540
auuguggaac uucggacgg caggggugug gaagcccuca aauauggug gaaucuccua    6600
caauauugga gucaggagcu aaagaauagu gcuguuagcu ugcucaaugc cacagccaua    6660
gcaguagcug aggggacaga uaggguuaua gaaguaguac aaggagcuug uagagcuauu    6720
cgccacauac cuagaagaau aagacagggc uuggaaagga uuugcuauua gaugggugg    6780
cgcgccgca cucagaucuu gagcucagc uuggauucug cagucgacgg uaccgcgggc    6840
ccgggaucca ccggucgcca ccauggugag caagggcgag gagcuguuca ccggggugu    6900
gcccauccug gucgagcugg acggcgacgu aaacggccac aaguucagcg ugccggcga    6960
gggcgagggc gaugccaccu acggcaagcu gacccugaag uucaucugca ccaccggcaa    7020
gcugcccgug cccuggccca cccucgugc cacccugacc uacggcgugc agugcuucag    7080
ccgcuacccc gaccacauga agcagcacga cuucuucaag uccgccaugc ccgaaggcua    7140
cguccaggag cgcaccaucu ucuucaagga cgacggcaac uacaagaccc gcgccgaggu    7200
gaaguucgag ggcgacaccc ugguggaccg caucgagcug aagggcaucg acuucaagga    7260
ggacggcaac auccuggggc acaagcugga guacaacuac aacagccaca acgucuauau    7320
caugccgac aagcagaaga acggcaucaa ggugaacuuc aagauccgcc acaacaucga    7380
ggacggcagc gucagcucg ccgaccacua ccagcagaac ccccaucg cgacggccc    7440
cgucugcug cccgacaacc acuaccgag cacccagucc gcccgagca agacccaa    7500
cgagaagcgc gaucacaugg uccugcugga guucgugacc gccgccggga ucacucucgg    7560
caugacgag cuguacaagu aaagcggucg cgacucgaga ccuagaaaaa cauggagcaa    7620
ucacaaguag caauacagca gcuaacaaug cugcuugugc cuggcuagaa gcacaagagg    7680
aggaagaggu gggguuucca gucacacccc agguaccuuu aagaccaaug acuuacaagg    7740
cagcuguaga ucuuagccac uuuuuaaaag aaaagggggg acuggaaggg cuaauucacu    7800
cccaaagaag acaagauauc cuugaucugu ggaucuacca cacacaaggc uacuucccug    7860
```

```
auuggcagaa cuacacacca gggccagggg ucagauaucc acugaccuuu ggauggugcu   7920
acaagcuagu accaguugag ccagauaagg uagaagaggc caauaaagga gagaacacca   7980
gcuuguuaca cccugugagc cugcauggaa uggaugaccc ugagagagaa guguuagagu   8040
ggagguuuga cagccgccua gcauuucauc acguggcccg agagcugcau ccggaguacu   8100
ucaagaacug cugacaucga gcuugcuaca aggacuuuc cgcugggac uuccaggga      8160 ggcguggccu gggcgggacu ggggaguggc gagcccucag augcugcaua uaagcagcug   8220
cuuuuugccu guacuggguc ucucugguua gaccagaucu gagccuggga gcucucuggc   8280
uaacuaggga acccacugcu uaagccucaa uaaagcuugc cuugagugcu ucaaguaug    8340 ugugcccguc uguuguguga cucugguaac uagagauccc ucagacccuu uuagucagug   8400
uggaaaaucu cuagca                                                  8416
```

<210> SEQ ID NO 15
<211> LENGTH: 25
<212> TYPE: PRT
<213> ORGANISM: Human Immunodeficiency Virus

<400> SEQUENCE: 15

Asp Arg Leu His Pro Val His Ala Gly Pro Ile Ala Pro Gly Gln Met
1               5                   10                  15

Arg Glu Pro Arg Gly Ser Asp Ile Ala
            20                  25

<210> SEQ ID NO 16
<211> LENGTH: 25
<212> TYPE: PRT
<213> ORGANISM: Human Immunodeficiency Virus

<400> SEQUENCE: 16

Asp Arg Val His Pro Val His Ala Gly Pro Ile Ala Pro Gly Gln Met
1               5                   10                  15

Arg Glu Pro Arg Gly Ser Asp Ile Ala
            20                  25

<210> SEQ ID NO 17
<211> LENGTH: 13
<212> TYPE: PRT
<213> ORGANISM: Artificial Sequence
<220> FEATURE:
<223> OTHER INFORMATION: Synthetic linker in pIRE2EGFP vector

<400> SEQUENCE: 17

Ala Asn Tyr Ala Ala Ala Ala Ala Ala Ala Asp Pro Ser
1               5                   10

<210> SEQ ID NO 18
<211> LENGTH: 19
<212> TYPE: DNA
<213> ORGANISM: Artificial Sequence
<220> FEATURE:
<223> OTHER INFORMATION: Synthetic partial mir30 sequence

<400> SEQUENCE: 18
ctgtgaagcc acagatggg                                                  19

<210> SEQ ID NO 19
<211> LENGTH: 20
<212> TYPE: DNA
<213> ORGANISM: Artificial Sequence

```
<220> FEATURE:
<223> OTHER INFORMATION: Synthetic oligonucleotide

<400> SEQUENCE: 19
ggacttcgag caagagatgg                                                    20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20
agcactgtgt tggcgtacag                                                    20

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
tggcattcaa ggagtacctc                                                    20

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
ttgtagcaat gatctcaaca cg                                                 22

<210> SEQ ID NO 23
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 23
caaccatgag tacaaatggt g                                                  21

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24
ctcacatttg cttggttgtc                                                    20

<210> SEQ ID NO 25
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 25
aggtctcttc agcatttatt gg                                                 22
```

```
<210> SEQ ID NO 26
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 26
tattgttctc actcatggtt gc                                              22

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27
tactccgtga agtctaggga                                                 20

<210> SEQ ID NO 28
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 28
taatatggta gactgtcaca gagc                                            24

<210> SEQ ID NO 29
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 29
aactgtggta tagcatatgt gg                                              22

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 30
ctctcaattg caccagtttc c                                               21

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31
gtctcctttg agctgtttgc                                                 20

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide
```

```
<400> SEQUENCE: 32
cgtatgcttt aggatgaagt tctc                                              24

<210> SEQ ID NO 33
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 33
cccttcattg tagatctgat tacc                                              24

<210> SEQ ID NO 34
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 34
tgcaggtcca cagtattctc                                                   20

<210> SEQ ID NO 35
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 35
ctgcctggat ggccagtcac ac                                                22

<210> SEQ ID NO 36
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 36
cattgtagat ctgattacct tc                                                22

<210> SEQ ID NO 37
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 37
gccacacata ctgggcagtg ag                                                22

<210> SEQ ID NO 38
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 38
gcctcagggc cttggtagaa at                                                22

<210> SEQ ID NO 39
```

```
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 39
tacccaggaa gacattctgg at                                               22

<210> SEQ ID NO 40
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 40
ctggcatctt gtccatggca aa                                               22

<210> SEQ ID NO 41
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 41
ggttcctgct ttcacagaat ta                                               22

<210> SEQ ID NO 42
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 42
tgtggtgttt ggcaaagtga aa                                               22

<210> SEQ ID NO 43
<211> LENGTH: 35
<212> TYPE: PRT
<213> ORGANISM: Artificial Sequence
<220> FEATURE:
<223> OTHER INFORMATION: Synthetic fusion peptide

<400> SEQUENCE: 43

Gly Arg Lys Lys Arg Arg Gln Arg Arg Asp Arg Leu His Pro Val
 1               5                  10                  15

His Ala Gly Pro Ile Ala Pro Gly Gln Met Arg Glu Pro Arg Gly Ser
            20                  25                  30

Asp Ile Ala
        35

<210> SEQ ID NO 44
<211> LENGTH: 9
<212> TYPE: PRT
<213> ORGANISM: Artificial Sequence
<220> FEATURE:
<223> OTHER INFORMATION: Synthetic Tat intracellular targeting sequence

<400> SEQUENCE: 44

Arg Lys Lys Arg Arg Gln Arg Arg Arg
 1               5
```

```
<210> SEQ ID NO 45
<211> LENGTH: 35
<212> TYPE: PRT
<213> ORGANISM: Artificial Sequence
<220> FEATURE:
<223> OTHER INFORMATION: Synthetic Human Immunodeficiency Virus
      cyclophilin A binding peptide derivative

<400> SEQUENCE: 45

Gly Arg Lys Lys Arg Arg Gln Arg Arg Arg Asp Arg Leu His Pro Val
1               5                   10                  15

His Ala Gly Pro Ile Glu Pro Gly Gln Met Arg Glu Pro Arg Gly Ser
            20                  25                  30

Asp

-continued

<210> SEQ ID NO 50
<211> LENGTH: 112
<212> TYPE: PRT
<213> ORGANISM: Artificial Sequence
<220> FEATURE:
<223> OTHER INFORMATION: Synthetic protein comprising simian
      immunodeficiency virus mac251 Vpx

<400> SEQUENCE: 50

Met Ser Asp Pro Arg Glu Arg Ile Pro Pro Gly Asn Ser Gly Glu Glu
1               5                   10                  15

Thr Ile Gly Glu Ala Phe Glu Trp Leu Asn Arg Thr Val Glu Glu Ile
            20                  25                  30

Asn Arg Glu Ala Val Asn His Leu Pro Arg Glu Leu Ile Phe Gln Val
        35                  40                  45

Trp Gln Arg Ser Trp Glu Tyr Trp His Asp Glu Gln Gly Met Ser Gln
    50                  55                  60

Ser Tyr Val Lys Tyr Arg Tyr Leu Cys Leu Met Gln Lys Ala Leu Phe
65                  70                  75                  80

Met His Cys Lys Lys Gly Cys Arg Cys Leu Gly Glu Gly His Gly Ala
                85                  90                  95

Gly Gly Trp Arg Pro Gly Pro Pro Pro Pro Pro Gly Leu Ala
            100                 105                 110

<210> SEQ ID NO 51
<211> LENGTH: 220
<212> TYPE: PRT
<213> ORGANISM: Artificial Sequence
<220> FEATURE:
<223> OTHER INFORMATION: synthetic fusion protein comprising simian
      immunodeficiency virus mac251 Vpx and human
      immunodeficiency virus-1 NL4-3 Vpr

<400> SEQUENCE: 51

Met Ser Asp Pro Arg Glu Arg Ile Pro Pro Gly Asn Ser Gly Glu Glu
1               5                   10                  15

Thr Ile Gly Glu Ala Phe Glu Trp Leu Asn Arg Thr Val Glu Glu Ile
            20                  25                  30

Asn Arg Glu Ala Val Asn His Leu Pro Arg Glu Leu Ile Phe Gln Val
        35                  40                  45

Trp Gln Arg Ser Trp Glu Tyr Trp His Asp Glu Gln Gly Met Ser Gln
    50                  55                  60

Ser Tyr Val Lys Tyr Arg Tyr Leu Cys Leu Met Gln Lys Ala Leu Phe
65                  70                  75                  80

Met His Cys Lys Lys Gly Cys Arg Cys Leu Gly Glu Gly His Gly Ala
                85                  90                  95

Gly Gly Trp Arg Pro Gly Pro Pro Pro Pro Pro Gly Leu Ala
            100                 105                 110

Ala Asn Tyr Ala Ala Ala Ala Ala Ala Asp Pro Ser Glu Gln Ala
        115                 120                 125

Pro Glu Asp Gln Gly Pro Gln Arg Glu Pro Tyr Asn Glu Trp Thr Leu
    130                 135                 140

Glu Leu Leu Glu Glu Leu Lys Ser Glu Ala Val Arg His Phe Pro Arg
145                 150                 155                 160

Ile Trp Leu His Asn Leu Gly Gln His Ile Tyr Glu Thr Tyr Gly Asp
                165                 170                 175

Thr Trp Ala Gly Val Glu Ala Ile Ile Arg Ile Leu Gln Gln Leu Leu
            180                 185                 190

-continued

```
Phe Ile His Phe Arg Ile Gly Cys Arg His Ser Arg Ile Gly Val Thr
        195                 200                 205
Arg Gln Arg Arg Ala Arg Asn Gly Ala Ser Arg Ser
    210                 215                 220
```